(12) United States Patent
Wu et al.

(10) Patent No.: US 11,572,372 B2
(45) Date of Patent: Feb. 7, 2023

(54) ANTI-HBV TETRAHYDROISOXAZOLO[4,3-C] PYRIDINE COMPOUNDS

(71) Applicants: CHIA TAI TIANQING PHARMACEUTICAL GROUP CO., LTD., Lianyungang (CN); MEDSHINE DISCOVERY INC., Jiangsu (CN)

(72) Inventors: Lifang Wu, Shanghai (CN); Fei Sun, Shanghai (CN); Jinhua Du, Shanghai (CN); Charles Z. Ding, Shanghai (CN); Shuhui Chen, Shanghai (CN); Xiquan Zhang, Lianyungang (CN); Hongjiang Xu, Lianyungang (CN); Ling Yang, Lianyungang (CN)

(73) Assignee: Medshine Discovery Inc., Jiangsu (CN)

( * ) Notice: Subject to any disclaimer, the term of this patent is extended or adjusted under 35 U.S.C. 154(b) by 9 days.

(21) Appl. No.: 16/764,129

(22) PCT Filed: Nov. 16, 2018

(86) PCT No.: PCT/CN2018/115857
§ 371 (c)(1),
(2) Date: May 14, 2020

(87) PCT Pub. No.: WO2019/096241
PCT Pub. Date: May 23, 2019

(65) Prior Publication Data
US 2020/0377517 A1    Dec. 3, 2020

(30) Foreign Application Priority Data

Nov. 16, 2017 (CN) .......................... 201711138922.9
Apr. 16, 2018 (CN) .......................... 201810339723.2

(51) Int. Cl.
*C07D 498/04* (2006.01)
*A61P 31/20* (2006.01)

(52) U.S. Cl.
CPC ............ *C07D 498/04* (2013.01); *A61P 31/20* (2018.01)

(58) Field of Classification Search
None
See application file for complete search history.

(56) References Cited

FOREIGN PATENT DOCUMENTS

| WO | 2016/109689 A2 | 7/2016 | | |
|----|----|----|----|----|
| WO | 2016/113273 A1 | 7/2016 | | |
| WO | 2019/097479 A1 | 5/2019 | | |
| WO | WO 2019/097479 | * | 5/2019 | ........... C07D 498/04 |
| WO | 2019/126622 A1 | 6/2019 | | |

OTHER PUBLICATIONS

Of CAS RN 1900259-60-0 (entered into STN on Apr. 29, 2016) (Year: 2016).*
Extended European Search Report in EP 18879872.2, dated Apr. 9, 2021, 7 pages.
International Search Report in PCT/CN2018/115857, dated Feb. 19, 2019, 3 pages.

* cited by examiner

*Primary Examiner* — Craig D Ricci
(74) *Attorney, Agent, or Firm* — Kilpatrick Townsend & Stockton LLP

(57) ABSTRACT

Disclosed are a class of anti-HBV tetrahydroisoxazolo[4,3-c]pyridine compounds and pharmaceutically acceptable salts thereof or isomers thereof, the compounds being represented by the formula (I).

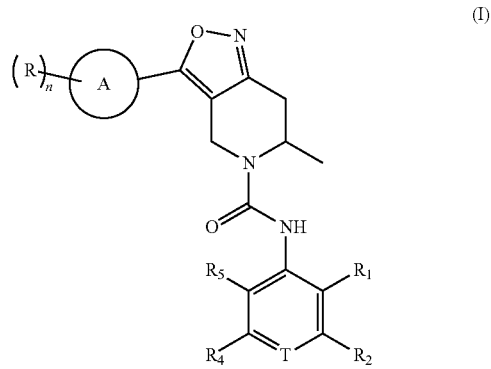

19 Claims, 2 Drawing Sheets

ANTI-HBV TETRAHYDROISOXAZOLO[4,3-C] PYRIDINE COMPOUNDS

CROSS REFERENCE TO RELATED APPLICATIONS

The present application is a U.S. National Stage Application of PCT/CN2018/115857, International Filing Date Nov. 16, 2018, which claims two priorities of Chinese patent application No. CN201711138922.9 filed on Nov. 16, 2017 and Chinese Patent Application No. CN201810339723.2 filed on Apr. 16, 2018, which are incorporated herein by reference in their entireties.

TECHNICAL FIELD

The present invention relates to the field of pharmaceuticals, and particularly to a novel class of anti-HBV tetrahydroisoxazolo[4, 3-c]pyridine compounds, preparation processes thereof, and use thereof in the manufacture of a medicament for the treatment of hepatitis B.

BACKGROUND

According to WHO statistics, there are currently about 240 million people worldwide infected with HBV (hepatitis B virus), which directly or indirectly causes about 680,000 deaths each year. China is a big country with hepatitis B infection which has an infected population of more than 70 million. Chronic infection with HBV can lead to malignant diseases such as liver failure, cirrhosis and liver cancer. (*World Health Organization, Hepatitis B: World Health Organization Fact Sheet* (2016).)

Currently, conventional drugs approved for the treatment of chronic hepatitis B are only nucleoside (acid) compounds and interferon. Nucleoside (acid) drugs, such as lamivudine, entecavir, tenofovir (ester), etc., can inhibit HBV DNA replication, but these drugs cannot eliminate cccDNA, and rebound thereof often occurs after drug withdrawal. Patients need long-term medication, and some patients are prone to drug resistance. Interferon drugs can partially activate the patient's immune system and inhibit hepatitis B virus through the body's autoimmunity action, but these drugs have significant side effects and patients are not well tolerated. More seriously, there are significant differences in the response rates of different populations to interferon treatment, but the overall response rate is low (usually less than 30%) (*Nat. Rev. Gastro. Hepat.* 8 (2011), 275-284).

In HBV-infected patients, stable covalently closed circular DNA, i.e., cccDNA, is formed within the hepatocyte nucleus of host as a template for HBV's continuous replication. All subgenomic RNA (sgRNA) and pregenomic RNA (pgRNA) are formed by transcription of cccDNA. After exiting from the nucleus, sgRNA is translated into protein X and three other envelope proteins, and pgRNA is translated into core protein and viral polymerase. PgRNA self-assembles with the core protein under the action of the polymerase to form Nucleocapsid-encapsulated RNA. In the nucleocapsid, pgRNA is reverse-transcribed into a negative strand of DNA, and thereby a positive strand of DNA is further synthesized to form rcDNA. On one hand, nucleocapsid-encapsulated rcDNA shells and enters into the nucleus to further amplify the cccDNA, and on the other hand, it recombines with the envelope protein and releases cells through the endoplasmic reticulum to form new HBV. In the replication cycle of HBV, synthesis of nucleocapsid is a key step in HBV genome replication process, and synthesis of viral DNA can only occur specifically within nucleocapsid. The assembly of the nucleocapsid is an evolutionary constraint process that limits the diversity of HBV, and it is very sensitive to even subtle molecular disturbances. For the development of new therapies against different HBV genotypes and drug-resistant strains, the targets that act on the synthesis and degradation processes of the nucleocapsid will be very promising. Some nucleocapsid-related anti-HBV compounds have been reported. Several related compounds such as NVR 3-778 (WO 2015109130A1), JNJ-56136379, and GLS-4 JHS are in clinical research stage.

SUMMARY

In one aspect, the present invention provides a compound of Formula (I), a pharmaceutically acceptable salt or an isomer thereof,

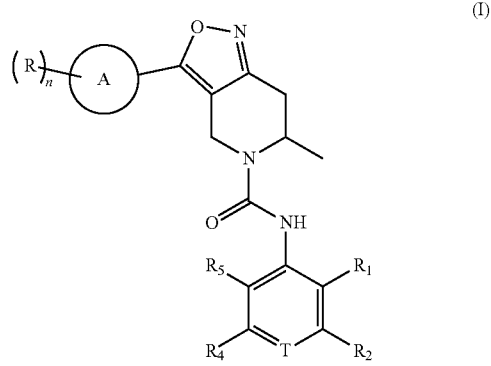

wherein ring A is 6- to 12-membered aryl or 5- to 6-membered heteroaryl;

each R is independently F; Cl; Br; I; —CN; —OH; —NR$^a$R$^b$; —S(=O)$_2$NR$^a$R$^b$; —S(=O)$_2$R$^c$; —C(=O)OR$^d$; $C_{1-6}$ alkoxy; or $C_{1-6}$ alkyl optionally substituted with 1, 2 or 3 substituents independently selected from the group consisting of F, Cl, Br, I, —OH, —OCH$_3$, —NH$_2$ and —CN;

n is 0, 1, 2 or 3;

T is N or CR$_3$;

R$_1$ and R$_5$ are each independently H; F; Cl; Br; I; —CN; —OH; —NR$^a$R$^b$; $C_{1-3}$ alkoxy; or $C_{1-3}$ alkyl optionally substituted with 1, 2 or 3 substituents independently selected from the group consisting of F, Cl, Br, I, —OH, —NH$_2$, —CN and —NO$_2$;

R$_2$ and R$_4$ are each independently H; F; Cl; Br; I; —CN; —OH; —NR$^a$R$^b$; $C_{1-6}$ alkoxy; or $C_{1-6}$ alkyl optionally substituted with 1, 2 or 3 substituents independently selected from the group consisting of F, Cl, Br, I, —OH, —NH$_2$, —CN and —NO$_2$;

R$_3$ is F, Br or —CN;

R$^a$, R$^b$, R$^c$ and R$^d$ are each independently H or $C_{1-6}$ alkyl;

the 5- to 6-membered heteroaryl contains 1, 2 or 3 heteroatoms or heteroatom groups independently selected from the group consisting of —O—, —S—, N and —NH—.

In some embodiments of the present invention, each R is independently F; Cl; Br; I; —CN; —OH; —NR$^a$R$^b$; —S(=O)$_2$NR$^a$R$^b$; —S(=O)$_2$R$^c$; —C(=O)OR$^d$; $C_{1-6}$ alkoxy; or $C_{1-6}$ alkyl optionally substituted with 1, 2, or 3 substituents independently selected from the group consisting of F, Cl, Br, I, —OH, —NH$_2$ and —CN; and other variables are as defined in the present invention.

In some embodiments of the present invention, the above-mentioned ring A is phenyl or 5- to 6-membered heteroaryl, and other variables are as defined in the present invention.

In some embodiments of the present invention, the above-mentioned ring A is phenyl, thiazolyl, isothiazolyl, pyrazolyl, pyrrolyl, pyrazinyl, pyrimidinyl, or pyridyl, and other variables are as defined in the present invention.

In some embodiments of the present invention, the above-mentioned $R^a$, $R^b$, $R^c$ and $R^d$ are each independently H, —$CH_3$, —$CH_2CH_3$, —$CH_2CH_2CH_3$ or —$CH_2(CH_3)_2$, and other variables are as defined in the present invention.

In some embodiments of the present invention, each R described above is independently F, Cl, Br, I, —CN, —OH, —$OCH_3$, —$OCH_2CH_3$, —$NH_2$, —$N(CH_3)_2$, —$S(=O)_2NH_2$, —$S(=O)_2CH_3$, —$C(=O)OCH_3$, —$C(=O)OCH_2CH_3$, —$CH_3$, —$CH_2CH_3$, $CF_3$ or —$CH_2OH$, and other variables are as defined in the present invention.

In some embodiments of the present invention, each R described above is independently F, Cl, Br, I, —CN, $C_{1-3}$ alkoxy or $C_{1-3}$ alkyl, and other variables are as defined in the present invention.

In some embodiments of the present invention, each R described above is independently F, Cl, —CN, or methoxy, and other variables are as defined in the present invention.

In some embodiments of the present invention, the above-mentioned n is 0, 1 or 2, and other variables are as defined in the present invention.

In some embodiments of the present invention, the above-mentioned $R_1$ and $R_5$ are each independently H, F, Cl, Br, I, —CN, —OH, —$OCH_3$, —$NH_2$, —$CH_3$, —CHF, —$CHF_2$ or —$CF_3$, and other variables are as defined in the present invention.

In some embodiments of the present invention, the above-mentioned $R_1$ and $R_5$ are each independently H, and other variables are as defined in the present invention.

In some embodiments of the present invention, the above-mentioned $R_2$ and $R_4$ are each independently H; F; Cl; Br; I; —CN; —OH; —$NH_2$; $C_{1-3}$ alkoxy; or $C_{1-3}$ alkyl optionally substituted with 1, 2, or 3 substituents independently selected from the group consisting of F, Cl, Br, and I; and other variables are as defined in the present invention.

In some embodiments of the present invention, the above-mentioned $R_2$ and $R_4$ are each independently H; F; Cl; —CN; or methyl optionally substituted with 2 (fluorine) F atoms; and other variables are as defined in the present invention.

In some embodiments of the present invention, the above-mentioned $R_2$ and $R_4$ are each independently H, F, Cl, Br, I, —CN, —OH, —$OCH_3$, —$OCH_2CH_3$, —$NH_2$, —$CH_3$, —$CH_2CH_3$, —CHF, —$CHF_2$ or —$CF_3$, and other variables are as defined in the present invention.

In some embodiments of the present invention, the above structural unit

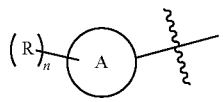

is

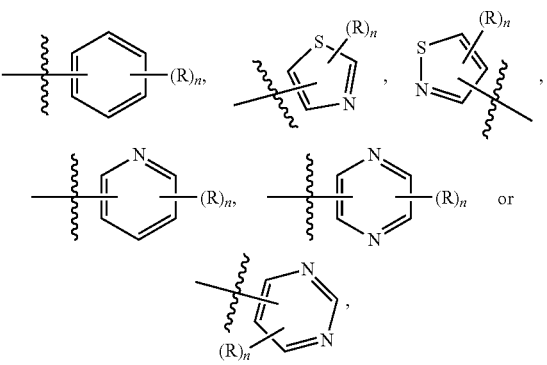

R, n and other variables are as defined in the present invention; in some embodiments of the present invention, the above-mentioned structural unit

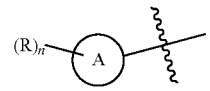

is

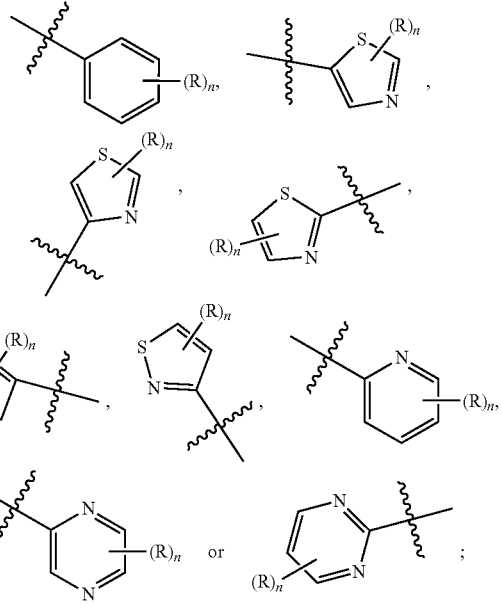

R, n and other variables are as defined in the present invention.

In some embodiments of the present invention, the above structural unit

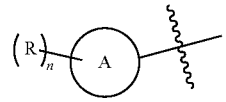

is
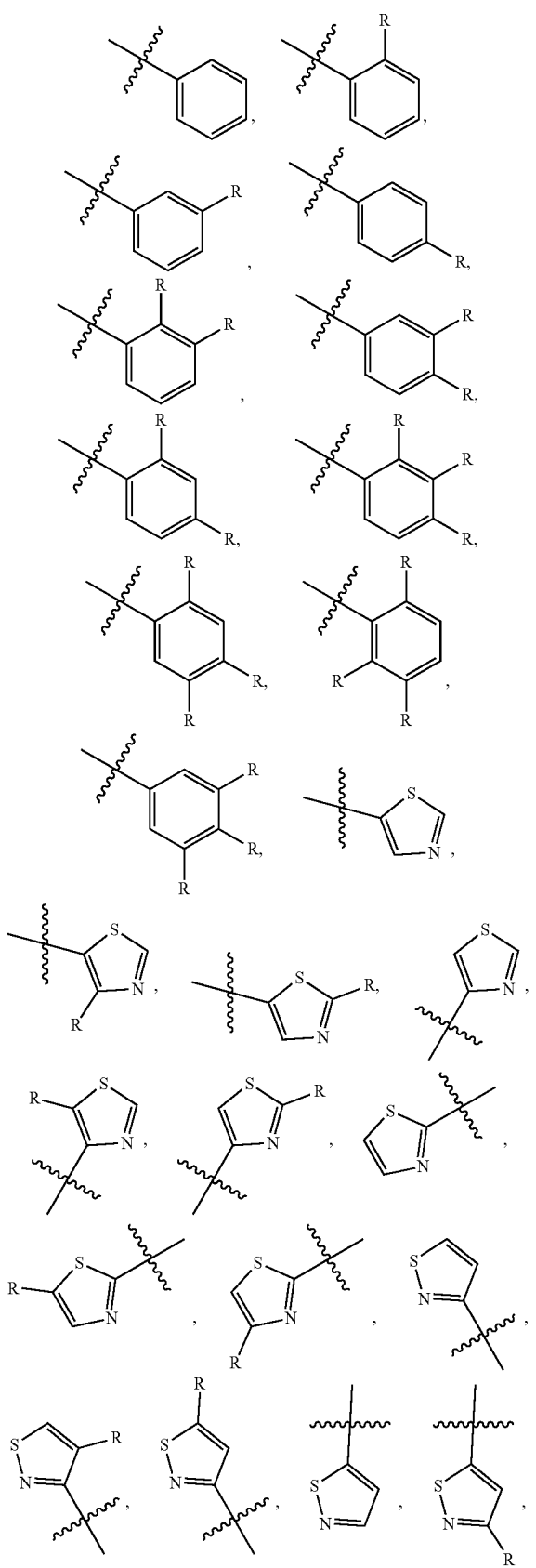
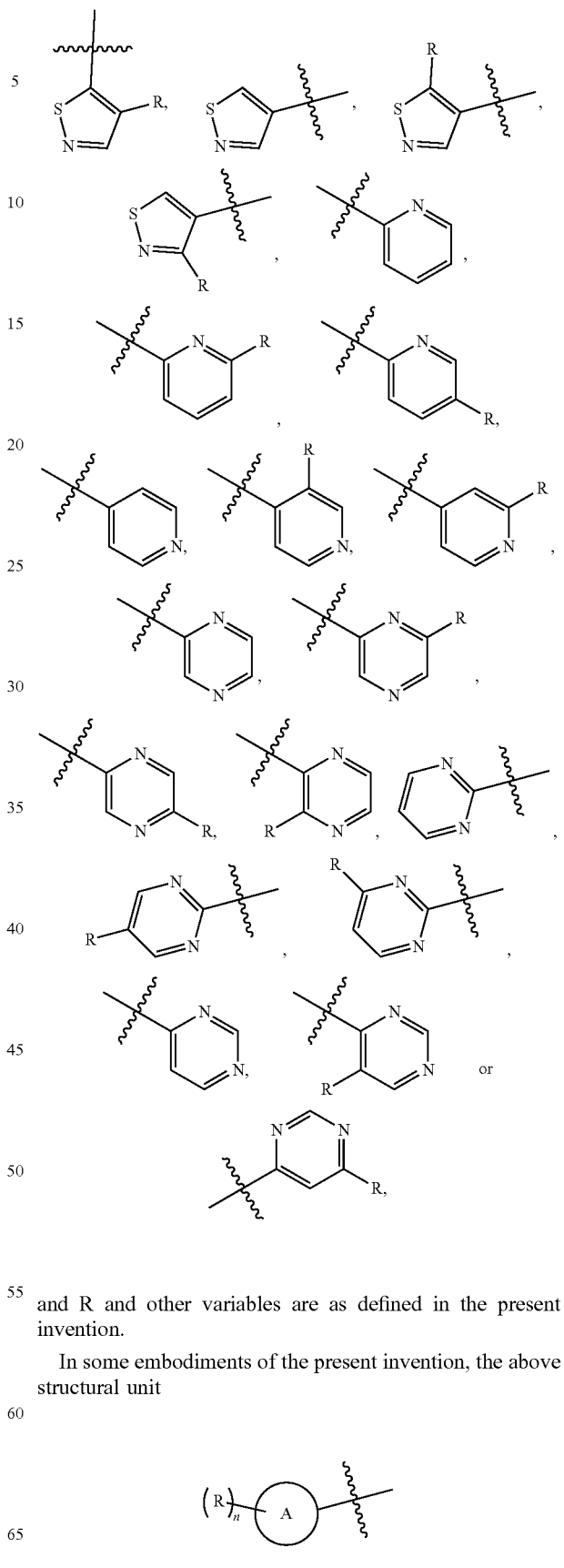
and R and other variables are as defined in the present invention.
In some embodiments of the present invention, the above structural unit
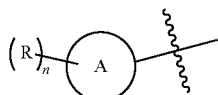

is
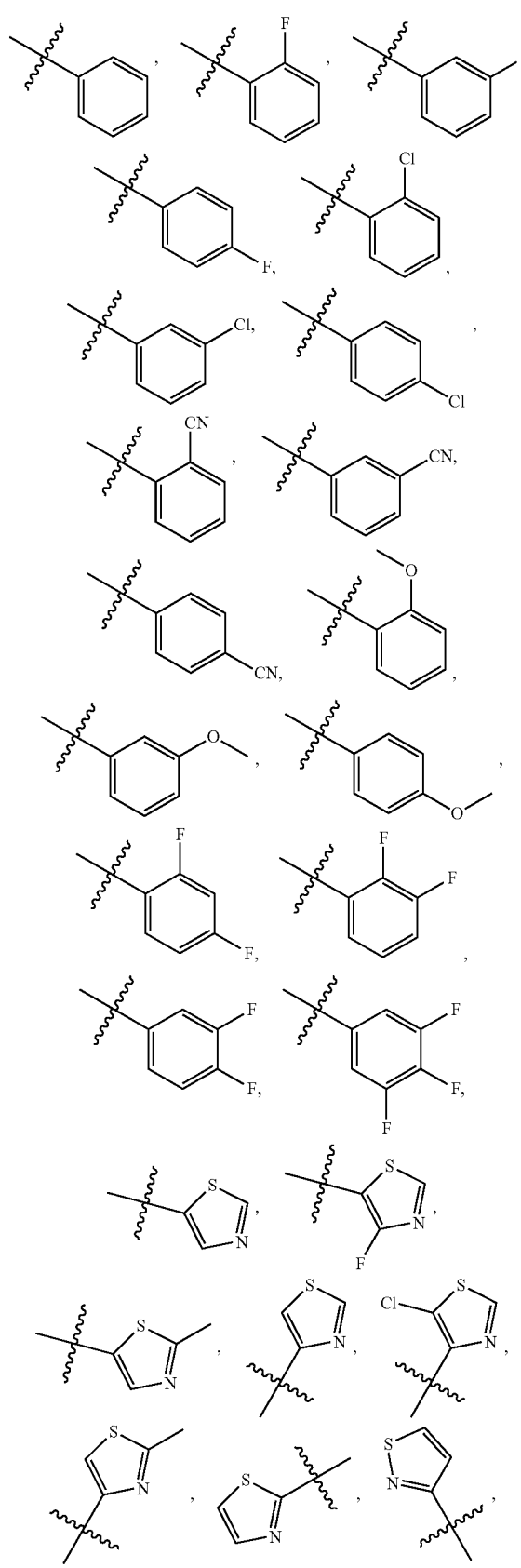
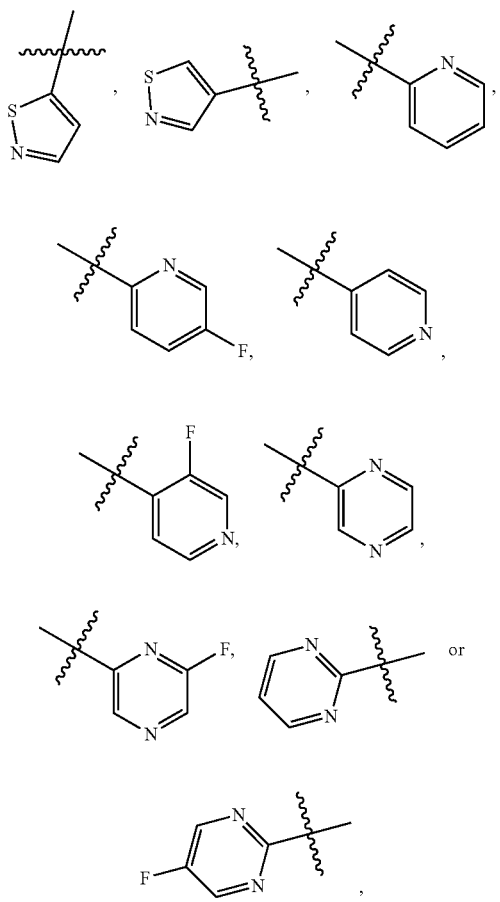
and other variables are as defined in the present invention.
In some embodiments of the present invention, the above structural unit
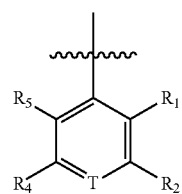
is
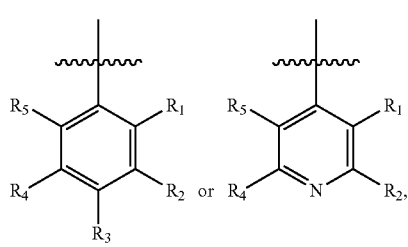
and $R_1$, $R_2$, $R_3$, $R_4$, $R_5$ and other variables are as defined in the present invention.

In some embodiments of the present invention, the above structural unit

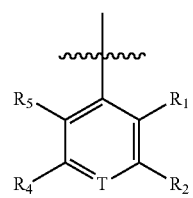

is

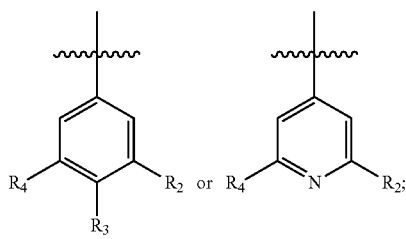

and R$_2$, R$_3$, R$_4$ and other variables are as defined in the present invention.

In some embodiments of the present invention, the above structural unit

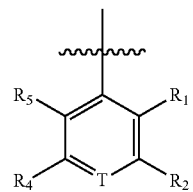

is

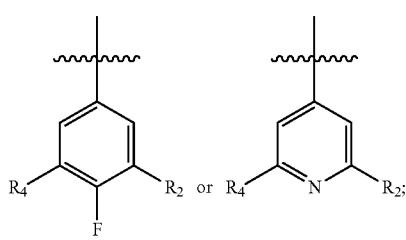

and R$_2$, R$_4$ and other variables are as defined in the present invention.

In some embodiments of the present invention, the above structural unit

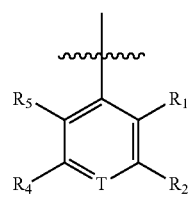

is

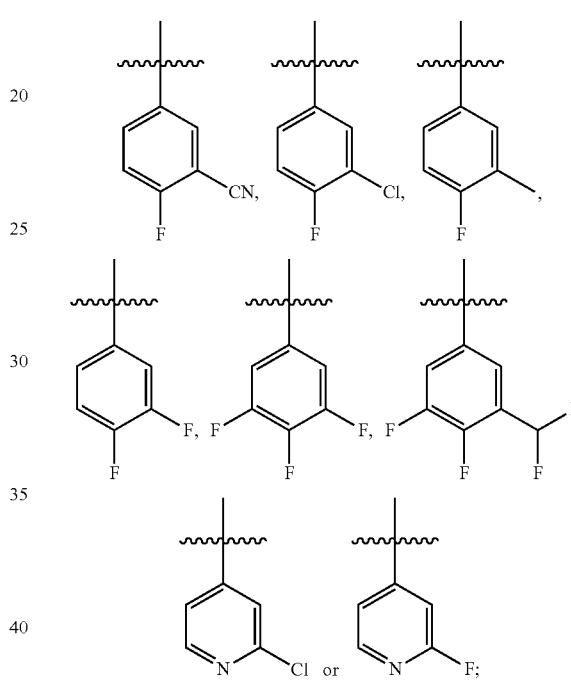

and other variables are as defined in the present invention.

In some embodiments of the present invention, the above compound, the pharmaceutically acceptable salt or isomer thereof has a structure of Formula (I-1):

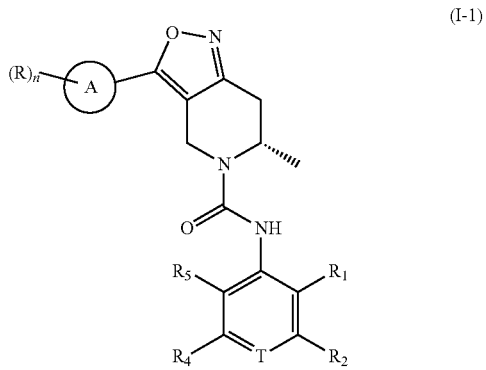

(I-1)

wherein, ring A, $R_1$, $R_2$, $R_4$, $R_5$, R, n, T and the structural unit

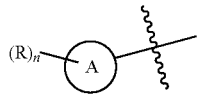

are as defined in the present invention.

In some embodiments of the present invention, the above compound, the pharmaceutically acceptable salt or isomer thereof has a structure represented by Formula (II-a) or Formula (III-a):

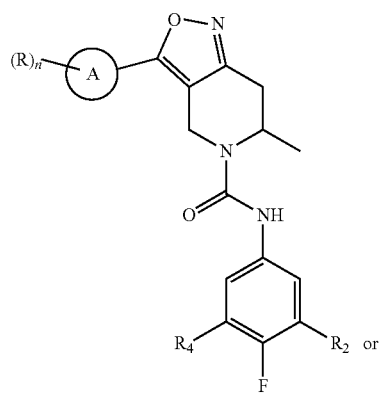

(II-a)

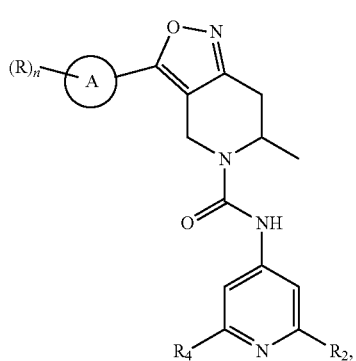

(III-a)

wherein ring A, $R_2$, $R_4$, R, n and the structural unit

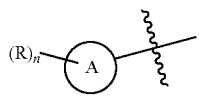

are as defined in the present invention.

In some embodiments of the present invention, the above compound, the pharmaceutically acceptable salt or isomer thereof has a structure represented by Formula (II-a-1) or Formula (III-a-1):

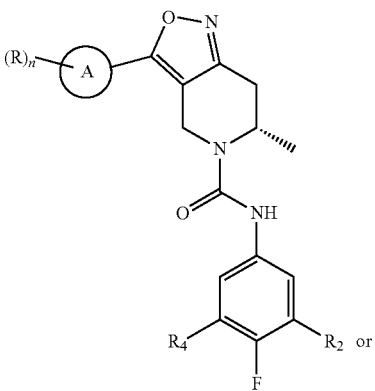

(II-a-1)

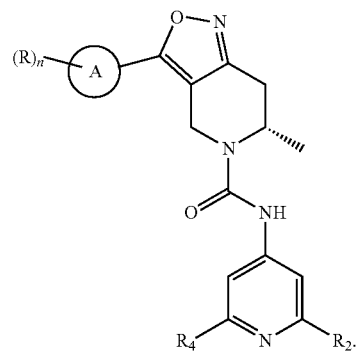

(III-a-1)

Wherein, ring A, $R_2$, $R_4$, R, n and the structural unit

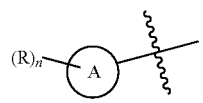

are as defined in the present invention.

In some embodiments of the present invention, the above compound, the pharmaceutically acceptable salt or isomer thereof has a structure represented by Formula (II-b), (II-c), (III-b), or (III-c):

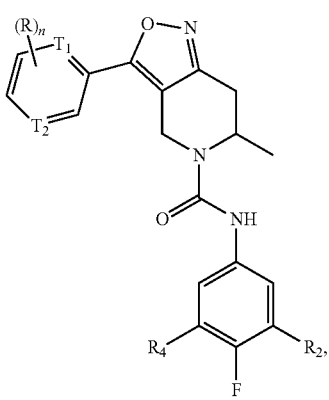

(II-b)

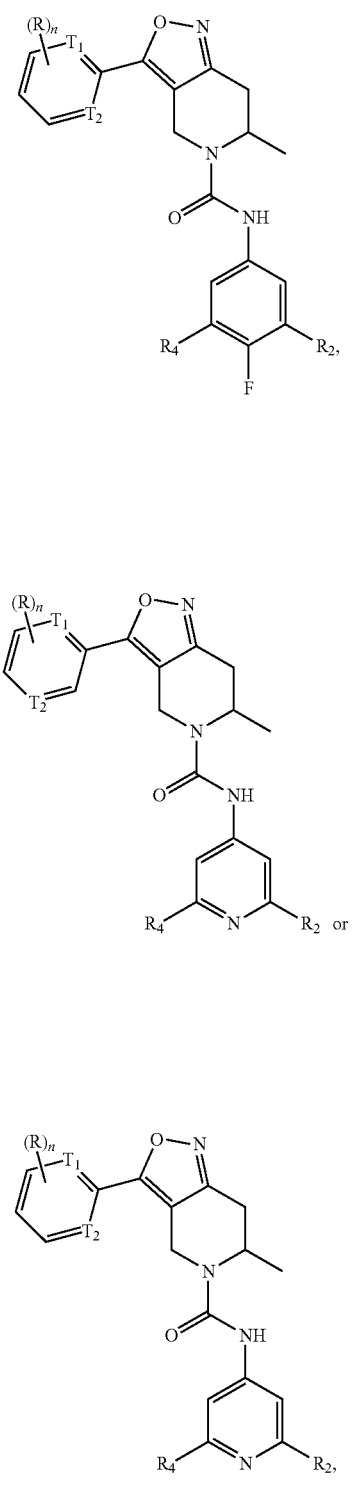

(II-c)

(III-b)

(III-c)

wherein, $T_1$ and $T_2$ are each independently N or CH; and $R_2$, $R_4$, R and n are as defined in the present invention.

In some embodiments of the present invention, the above compound, the pharmaceutically acceptable salt or isomer thereof has a structure represented by Formula (II-b-1), (II-c-1), (III-b-1), or (III-c-1):

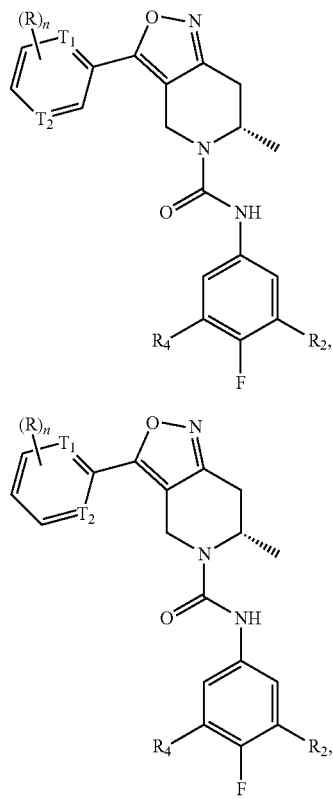

(II-b-1)

(II-c-1)

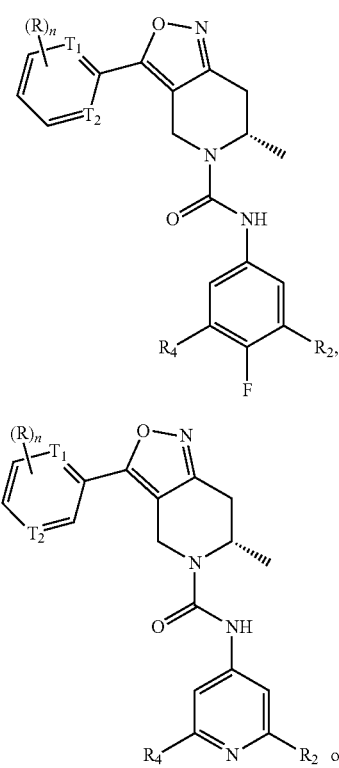

(III-b-1)

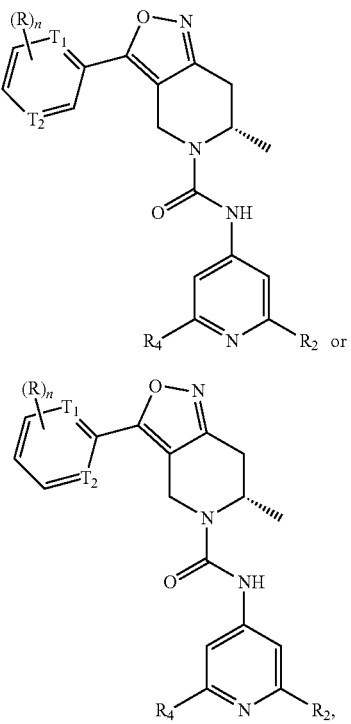

(III-c-1)

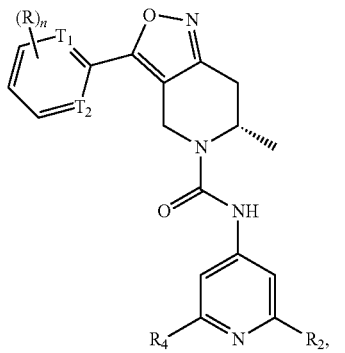

wherein, $T_1$ and $T_2$ are each independently N or CH; $R_2$, $R_4$, R and n are as defined in the present invention.

In some embodiments of the present invention, the above compound, the pharmaceutically acceptable salt or isomer thereof has a structure represented by Formula (II-d), (II-e), (II-f), (II-k), (III-d), (III-e), (III-f), or (III-k):

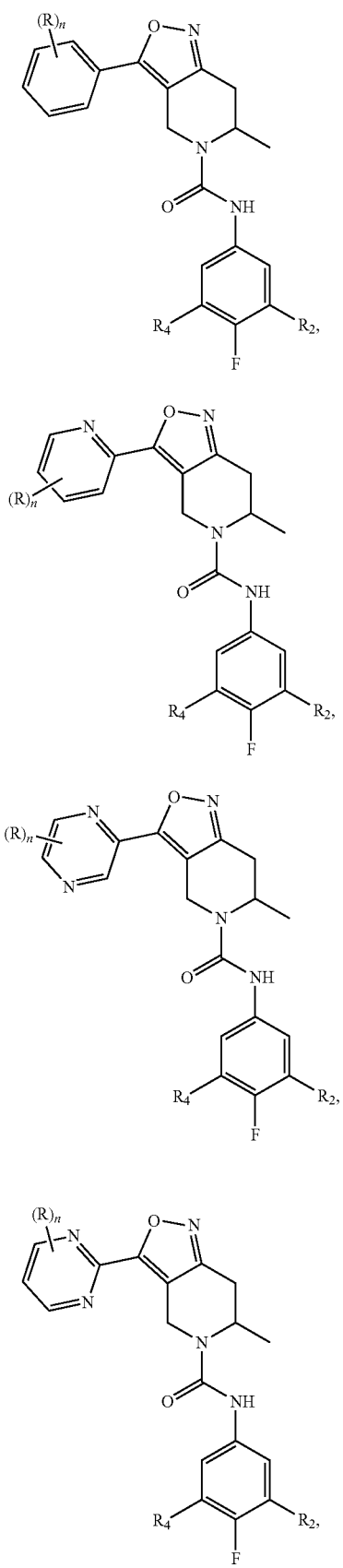
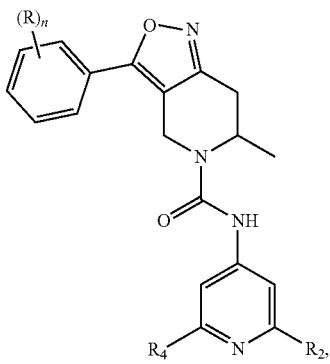
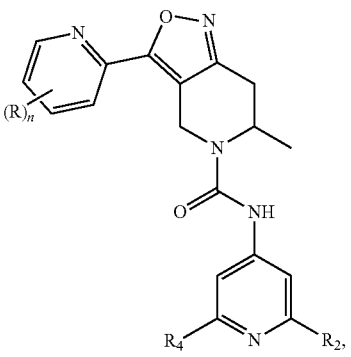
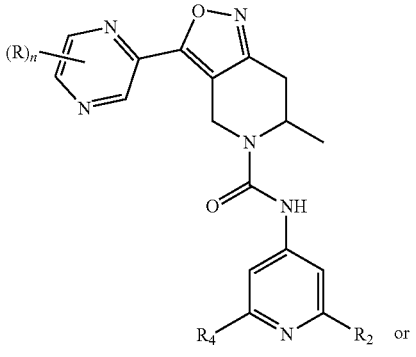
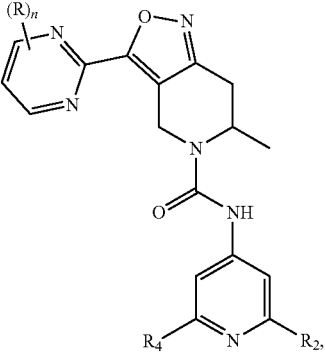
wherein $R_2$, $R_4$, R and n are as defined in the present invention.
In some embodiments of the present invention, the above compound, the pharmaceutically acceptable salt or isomer thereof has a structure represented by Formula (II-d-1), (II-e-1), (II-f-1), (II-k-1), (III-d-1), (III-e-1), (III-f-1), or (III-k-1):

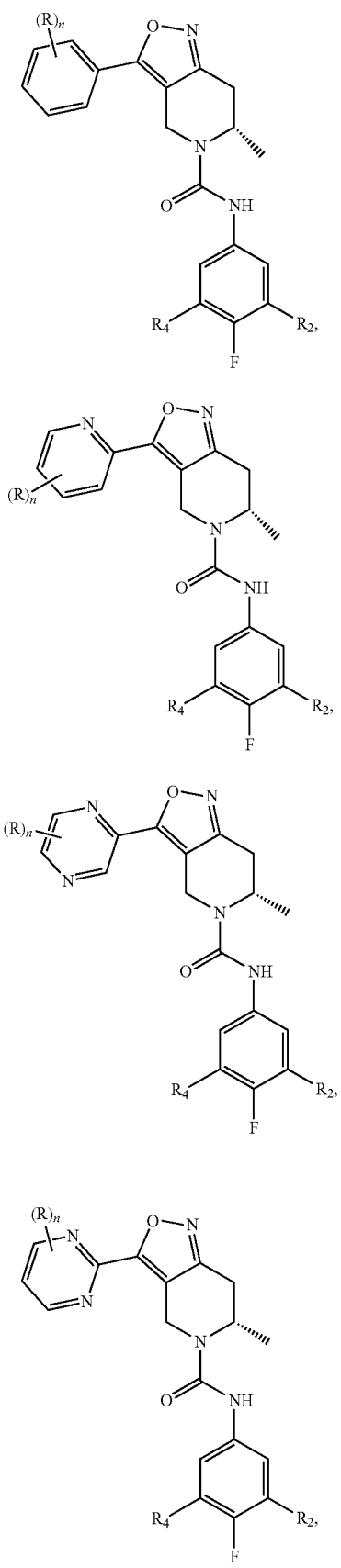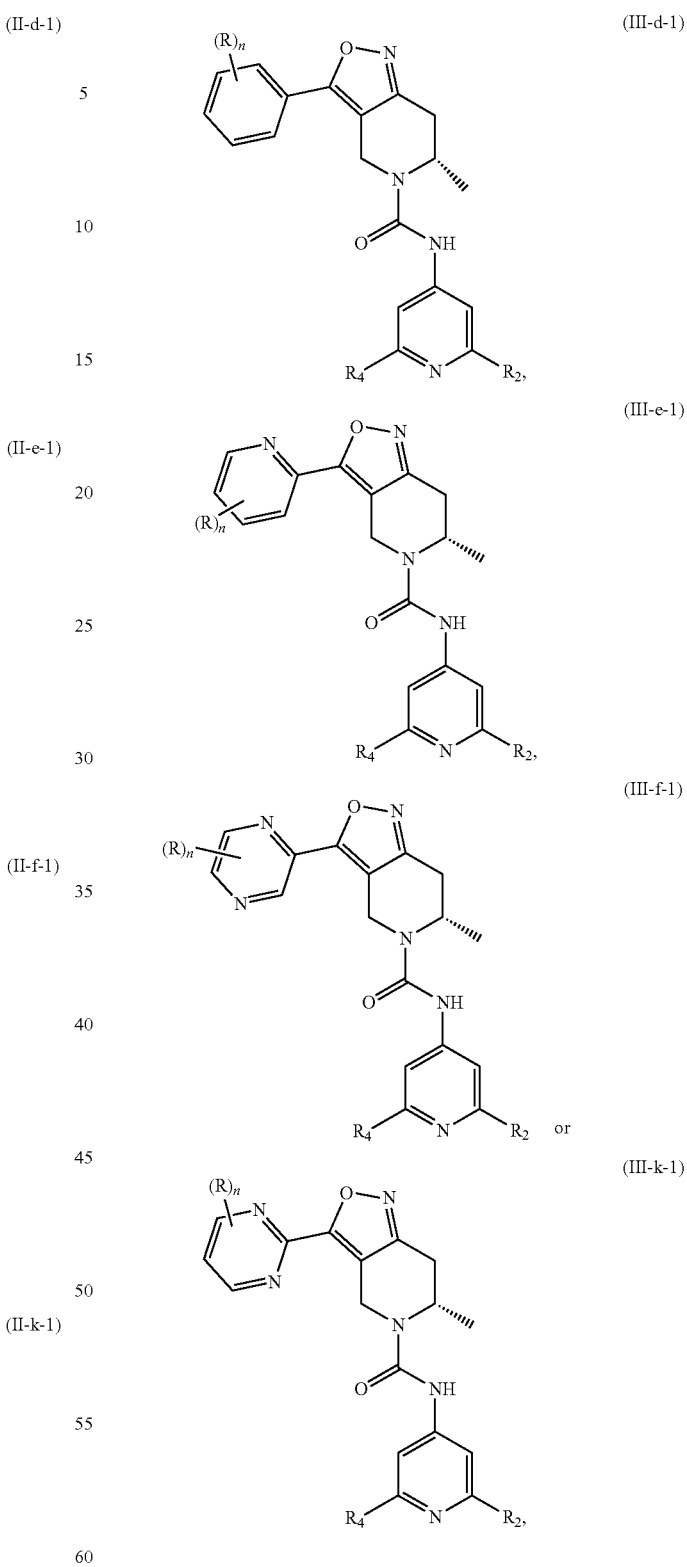
wherein, $R_2$, $R_4$, R and n are as defined in the present invention.
In some embodiments of the present invention, the above compound, the pharmaceutically acceptable salt or isomer thereof has a structure represented by Formula (II-m) or (III-m):

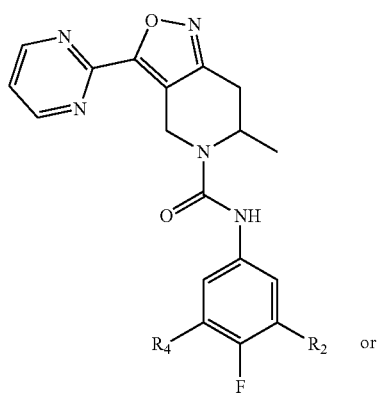
(II-m)

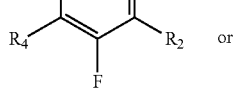 or

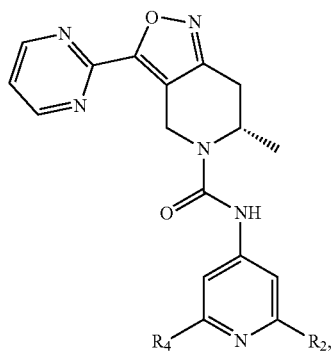
(III-m-1)

wherein, $R_2$ and $R_4$ are as defined in the present invention.

In some embodiments of the present invention, the above compound, the pharmaceutically acceptable salt or isomer thereof has a structure represented by Formulae (II-g) to (II-i) or Formulae (III-g) to (III-i):

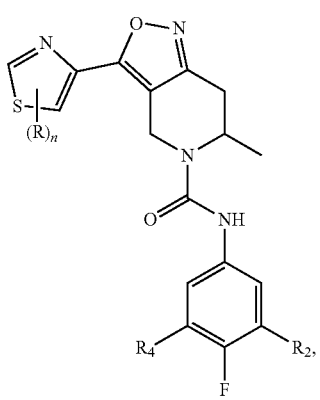
(II-g)

(III-m)

wherein, $R_2$ and $R_4$ are as defined in the present invention.

In some embodiments of the present invention, the above compound, the pharmaceutically acceptable salt or isomer thereof has a structure represented by Formula (II-m-1) or (III-m-1):

(II-m-1)

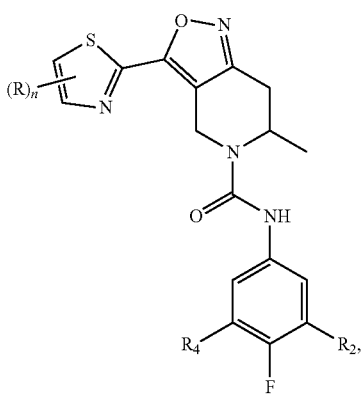
(II-h)

or

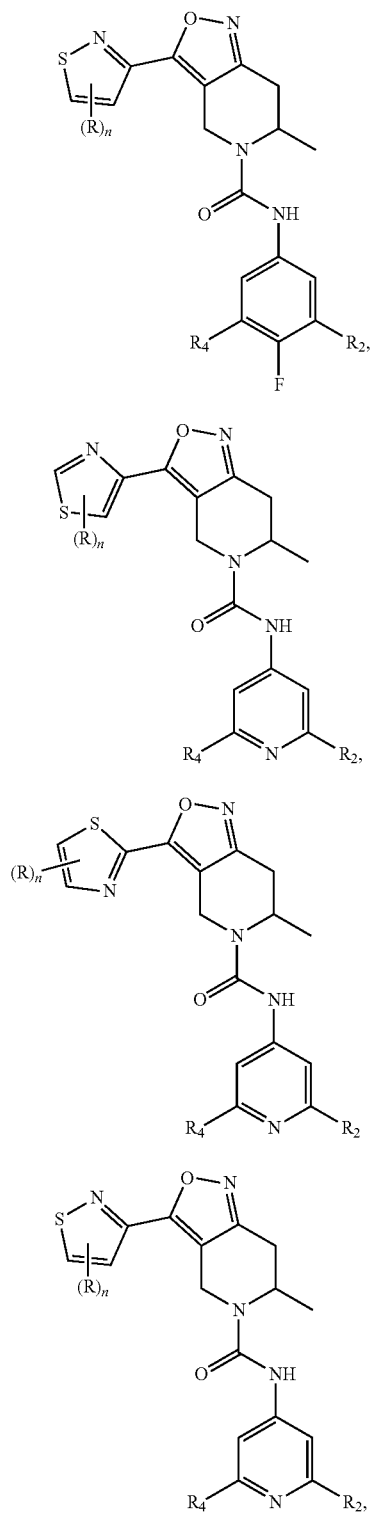
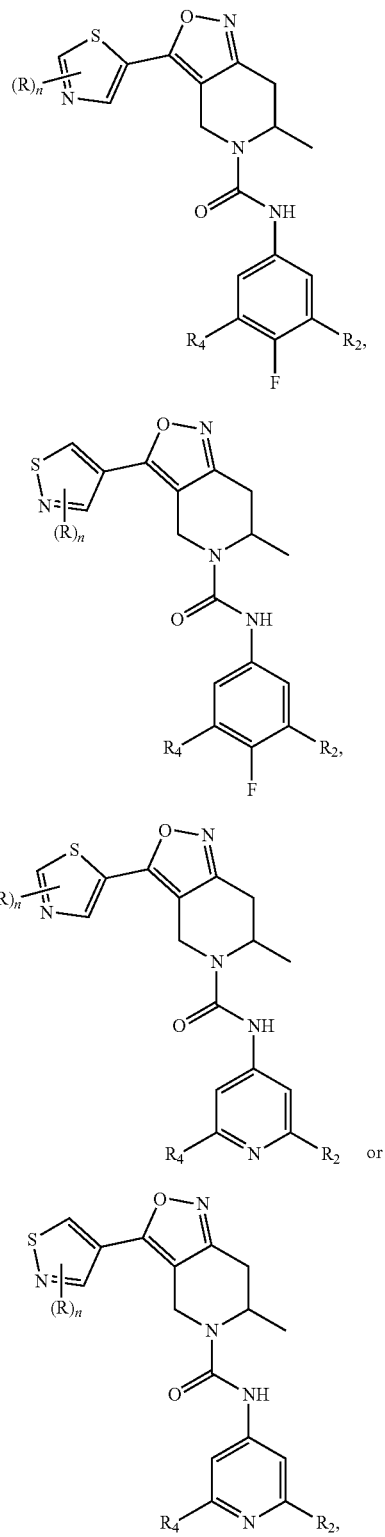

wherein, $R_2$, $R_4$, R and n are as defined in the present invention.

In some embodiments of the present invention, the above compound, the pharmaceutically acceptable salt or isomer thereof has a structure represented by Formulae (II-j) to (II-n) or Formulae (III-j) to (III-n):

wherein $R_2$, $R_4$, R and n are as defined in the present invention.

In some embodiments of the present invention, the above compound, the pharmaceutically acceptable salt or isomer thereof has a structure represented by Formulae (II-g-1) to (II-i-1) or Formulae (III-g-1) to (III-i-1):

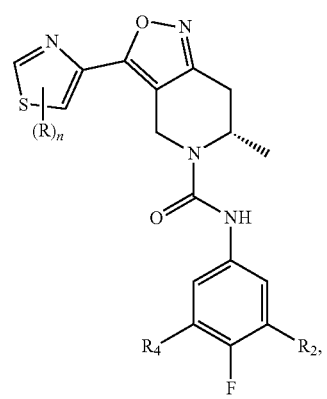
(II-g-1)
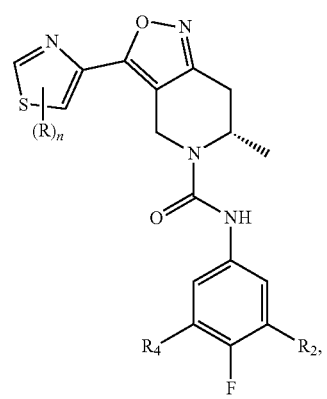
(II-h-1)
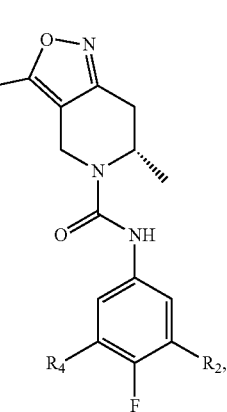
(II-i-1)
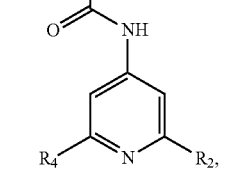
(III-g-1)
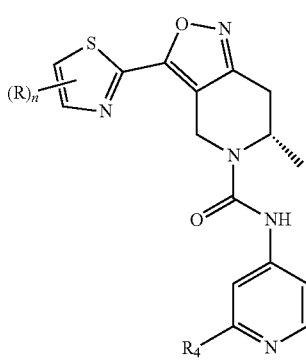
(III-h-1)
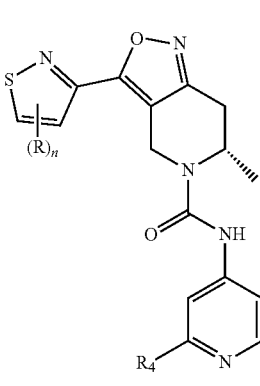
(III-i-1)
wherein, $R_2$, $R_4$, R and n are as defined in the present invention.
In some embodiments of the present invention, the above compound, the pharmaceutically acceptable salt or isomer thereof has a structure represented by Formulae (II-j-1) to (II-n-1) or Formulae (III-j-1) to (III-n-1):
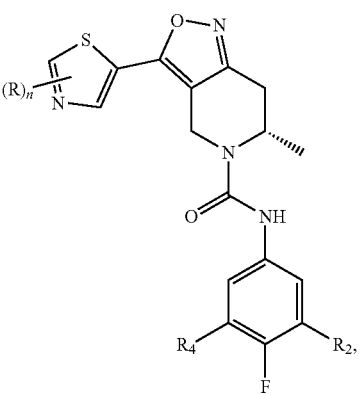
(II-j-1)

(II-n-1)
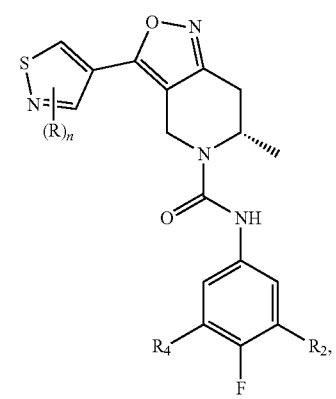
(III-j-1)
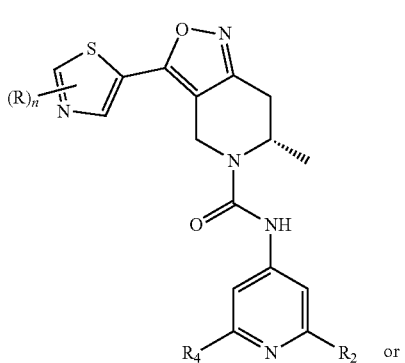
or
(III-n-1)
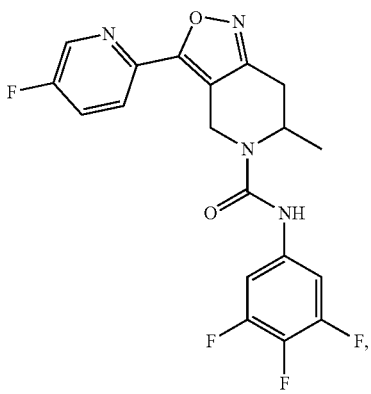
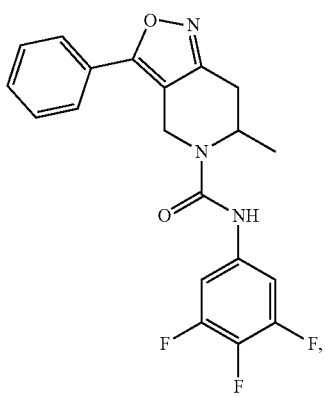
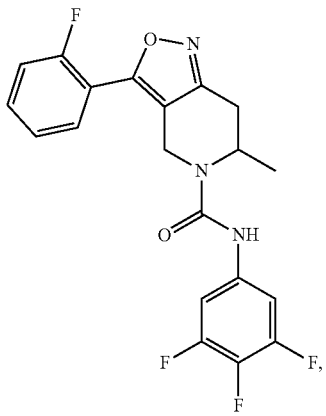
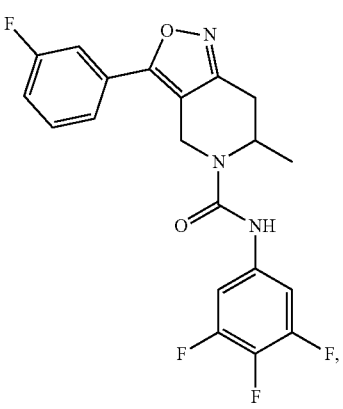
wherein, $R_2$, $R_4$, R and n are as defined in the present invention.
In some embodiments of the present invention, the above compound, the pharmaceutically acceptable salt or isomer thereof is selected from the group consisting of:

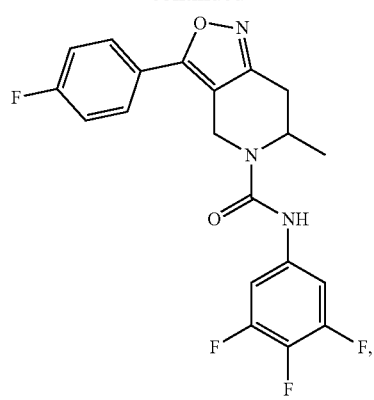
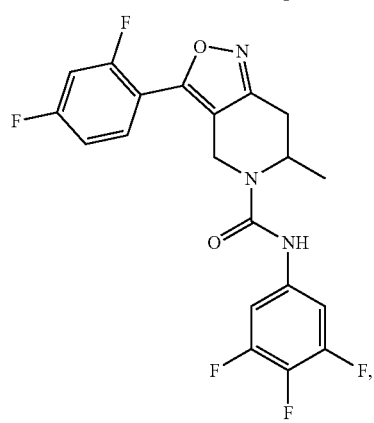
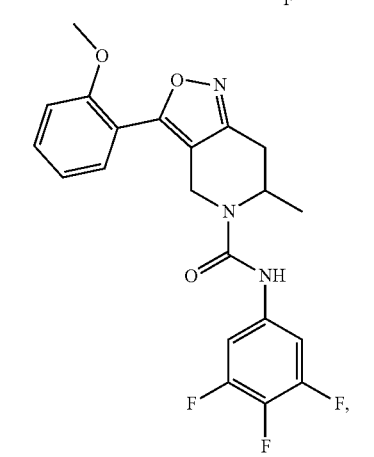
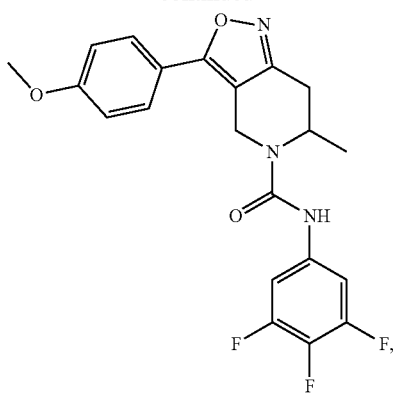

-continued
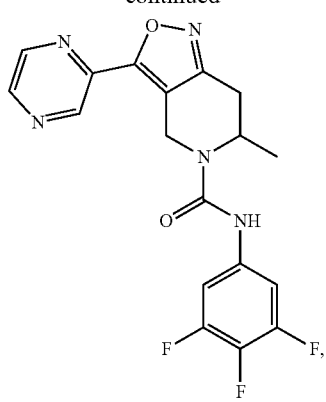
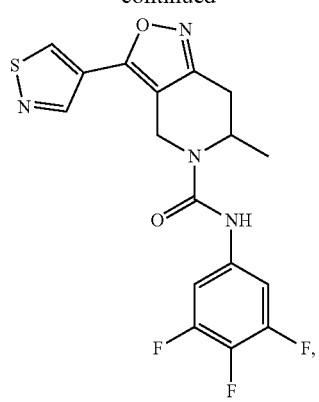
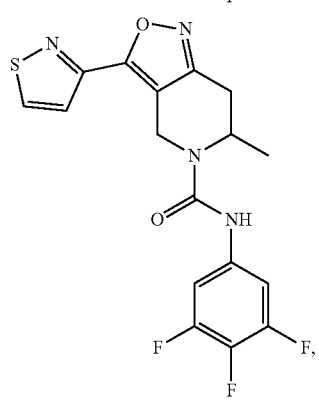
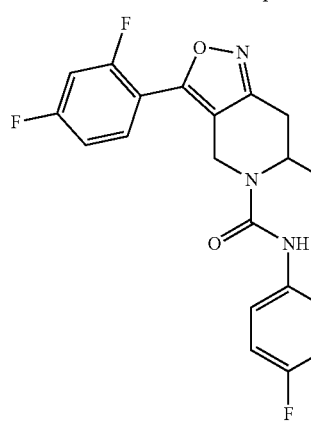
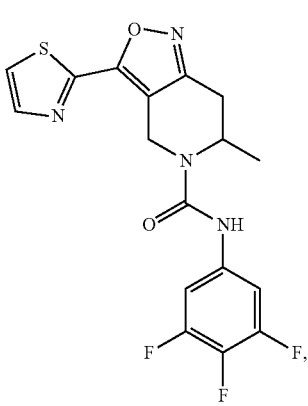
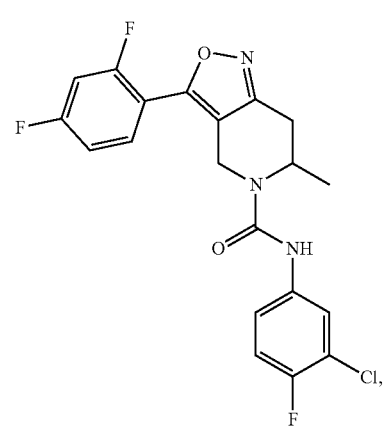

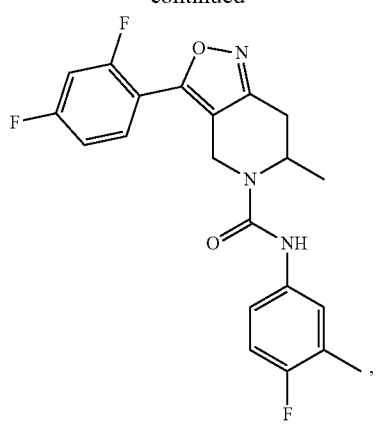
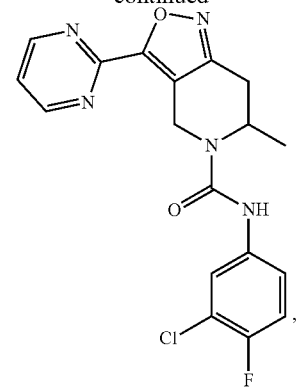
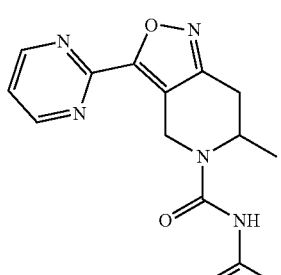
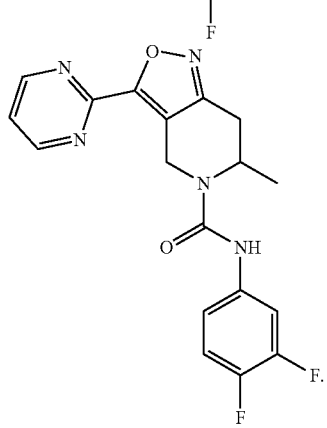
In some embodiments of the present invention, the above compound, the pharmaceutically acceptable salt or isomer thereof is selected from the group consisting of:
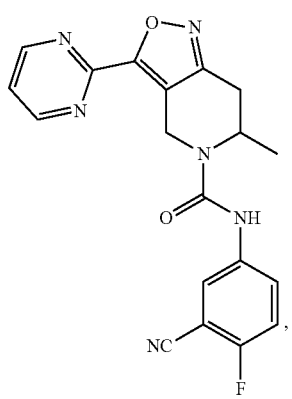
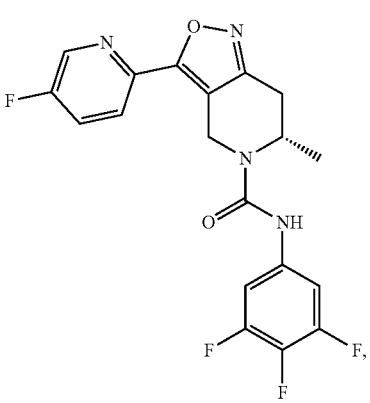

33
-continued
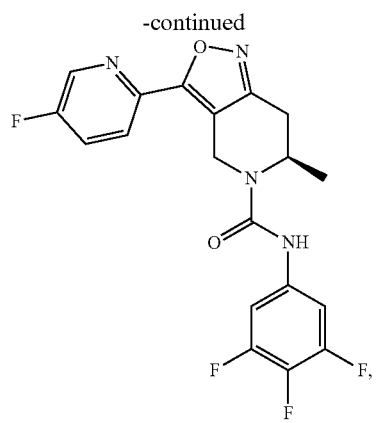
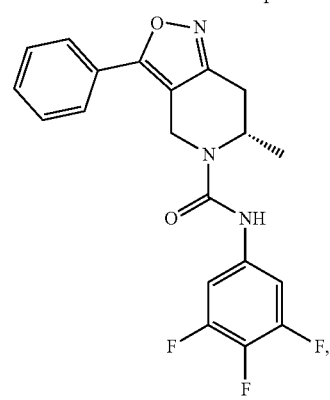
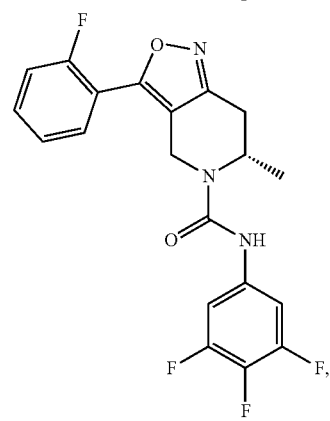
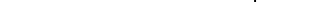
34
-continued
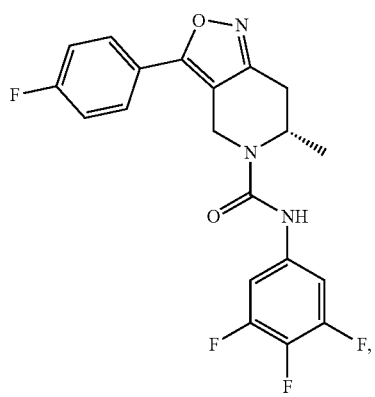
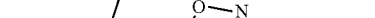
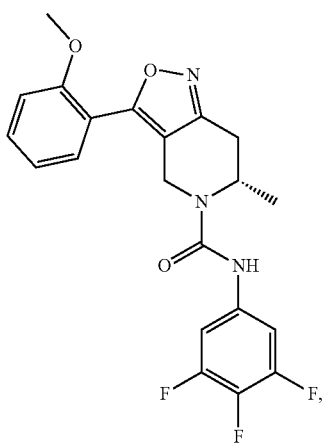

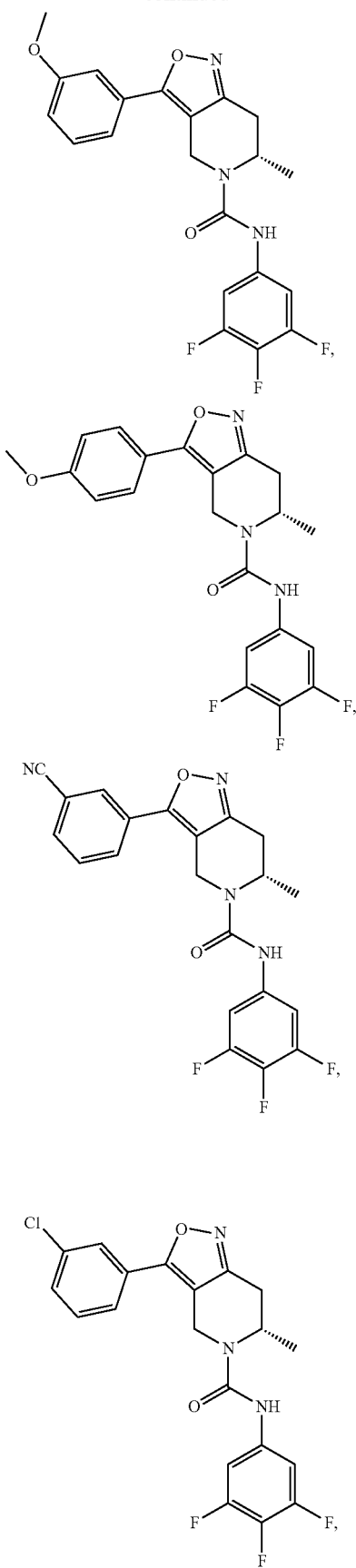

37
-continued
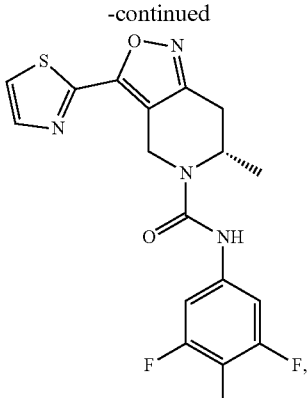
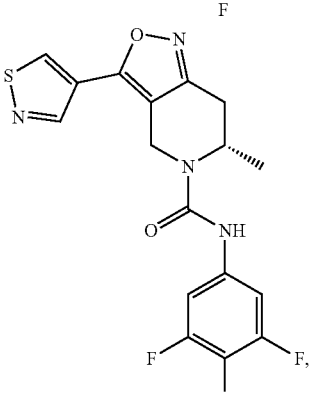
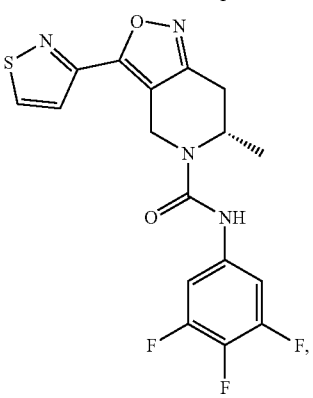
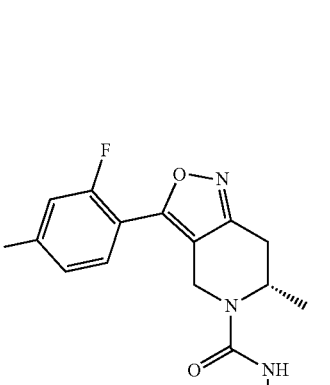
38
-continued
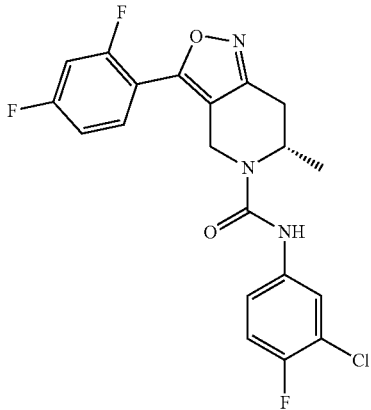
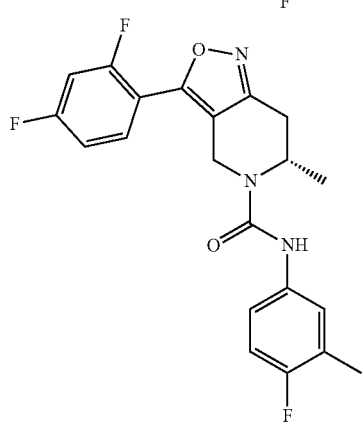
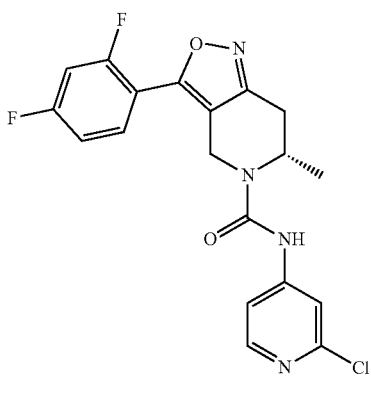
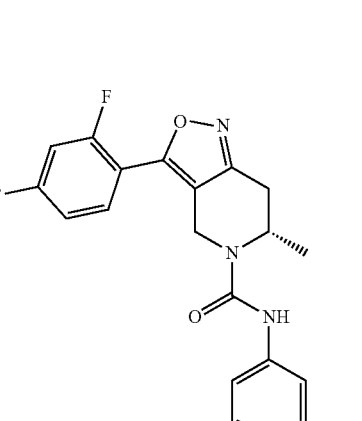

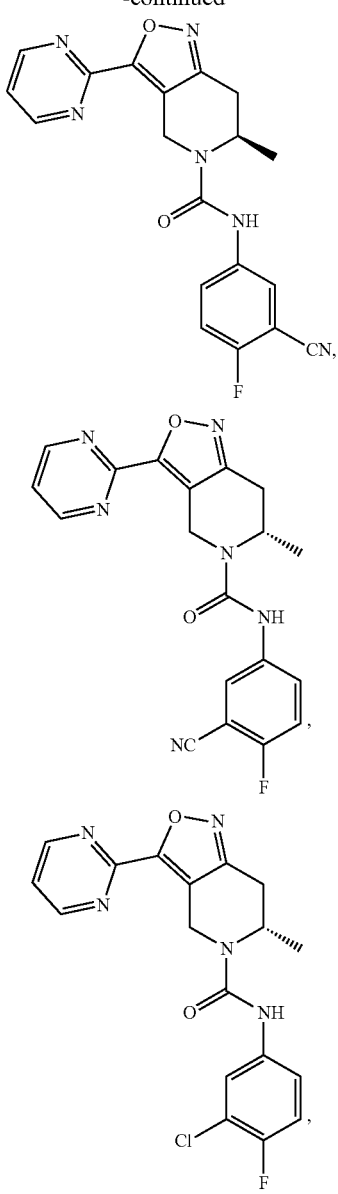

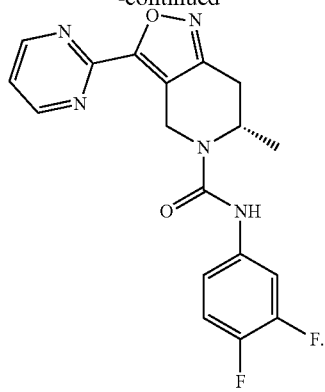

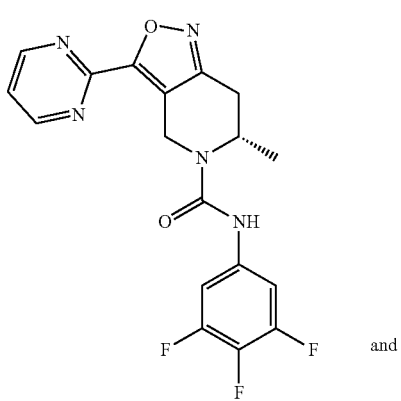

and

Other embodiments of the present invention are obtained by arbitrary combinations of the above variables.

In another aspect, the present invention also provides a pharmaceutical composition comprising a therapeutically effective amount of the above compound, a pharmaceutically acceptable salt or an isomer thereof as an active ingredient, and a pharmaceutically acceptable carrier.

In a further aspect, the present invention also provides use of the above compound, a pharmaceutically acceptable salt or an isomer thereof, or the above pharmaceutical composition thereof in the manufacture of an anti-hepatitis B medicament.

In still another aspect, the present invention also provides use of the above compounds, pharmaceutically acceptable salt or an isomer thereof, or the above pharmaceutical compositions thereof in the prevention or treatment of hepatitis B.

In yet another aspect, the present invention also provides a method for treating or preventing hepatitis B, comprising administering to a mammal, preferably a human, in need of such treatment or prevention a therapeutically effective amount of the above compound, a pharmaceutically acceptable salt or an isomer thereof, or the above pharmaceutical composition thereof.

In another aspect, the present invention also provides the above compound, a pharmaceutically acceptable salt or an isomer thereof, or the above pharmaceutical composition thereof for use in the treatment or prevention of hepatitis B.

The present invention relates to a new class of HBV inhibitors, the parent core structure of which is distinguished from the prior art. The compounds of the present invention exhibit an inhibitory activity against HBV DNA replication.

Definition and Description

Unless stated otherwise, the following terms and phrases used herein is intended to have the following meanings. A specific term or phrase shall not be considered unclear or indefinite when it is not specially defined. It should be understood in the generic sense. A trade name used herein refers to a corresponding product or an active ingredient thereof.

The term "pharmaceutically acceptable" used herein refers to a compound, material, composition and/or dosage form that is applicable to the contact with human and animal tissues without an excessive toxicity, irritation, allergic reaction or other problems or complications within the scope of reliable medical judgment, and are commensurate with an acceptable benefits/risk ratio.

The term "pharmaceutically acceptable salt" refers to a salt of the compound of the present invention, which is prepared by the compound with specific substituents discovered by the inventors and a relatively non-toxic acid or base. When the compound of the present invention contains a relatively acidic functional group, a base addition salt can be obtained by contacting the compound with a sufficient amount of a base in a pure solution or suitable inert solvent. When the compound of the present invention contains a relatively basic functional group, an acid addition salt can be obtained by contacting the compound with a sufficient amount of an acid in a pure solution or suitable inert solvent. Some specific compounds of the present invention contain basic and acidic functional groups so as to be able to be converted to any base addition salts or acid addition salts.

The pharmaceutically acceptable salt of the present invention can be synthesized from a parent compound containing an acidic or basic group by a conventional chemical method. Generally, the preparation method of the salt comprises: reacting these compounds in the forms of free acids or bases with a stoichiometric amount of suitable bases or acids in water or an organic solvent or the mixture of water and an organic solvent.

The compound of the present invention may exist as specific geometric or stereoisomeric isomers. The present invention contemplates that all of these compounds, including cis- and trans-isomers, (−)- and (+)-enantiomers, (R)- and (S)-enantiomers, diastereomers, (D)-isomers, (Z)-isomers, as well as racemic mixtures and other mixtures, such as enantiomer- or diastereoisomer-enriched mixtures, all of these mixtures are included within the scope of the present invention. Other asymmetric carbon atoms may exist in substituents such as alkyl. All of these isomers and their mixtures are included within the scope of the present invention.

Unless otherwise specified, the term "enantiomer" or "optical isomer" refers to stereoisomers that are mirror images of each other.

Unless otherwise specified, the term "diastereomer" refers to stereoisomers in which the molecules have two or more chiral centers and are not mirror images of one another.

Unless otherwise specified, "(+)" represents dextrorotation, "(−)" represents levorotation, and "(±)" represents racemization.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wavy line ( ) represents a wedged solid bond ( ) or a wedged dashed bond ( ), or a wavy line ( ) represents a straight solid bond ( ) or a straight dashed bond ( ).

Unless otherwise indicated, the term "enriched in one isomer", "isomer enriched", "enriched in one enantiomer" or "enantiomeric enriched" refers to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise indicated, the term "excess of isomer" or "excess of enantiomer" refers to the difference between the relative percentages of the two isomers or two enantiomers. For example, wherein, the content of one of the isomers or enantiomers is 90%, and the other one is 10%, then the excess of the isomer or enantiomer (ee value) is 80%.

Optically active (R)- and (S)-isomers and (D)- and (L)-isomers can be prepared by chiral synthesis or chiral reagents or other conventional techniques. If an enantiomer of a compound of the present invention is wanted, it can be prepared by asymmetric synthesis or the derivatization action with chiral auxiliaries, in which the resulting diastereomer mixtures are isolated, and the auxiliary groups are cleaved to provide the desired pure enantiomer. Alternatively, when a molecule contains a basic functional group (such as amino) or an acidic functional group (such as carboxyl), the molecule is reacted with an appropriate optical active acid or base to form a diastereomer salt, the diastereomer is resoluted by conventional methods known in the art, and then pure enantiomers can be obtained. In addition, the separation of enantiomers and diastereomers is usually realized by chromatographic method, and the chromatography method employs a chiral stationary phase, and optionally is combined with the chemical derivatization method (e.g. a carbamate is generated from an amine).

The compound of the present invention may comprise unnatural proportion of atomic isotopes at one or more atoms that constitute the compound. For example, the compound can be labeled by a radioactive isotope, such as tritium ($^3H$), iodine-125($^{125}I$) or C-14($^{14}C$). For another example, hydrogen can be replaced by heavy hydrogen to form a deuterated drug, and the bond formed from deuterium and carbon is stronger than the bond formed from common hydrogen and carbon. Compared with undeuterated drugs, deuterated drugs have the advantages of reducing toxic and side effects, increasing drug stability, enhancing efficacy, and prolonging the biological half-life of drugs. All the variants composed by isotopes of the compound of the present invention, whether radioactive or not, are included within the scope of the present invention.

The term "a pharmaceutically acceptable carrier" refers to any formulation or carrier medium which is capable of delivering an effective amount of the active substance disclosed in the present invention, does not interfere with the biological activity of the active substance, and has no toxic side-effects on a host or patient. Representative carriers include water, oil, vegetables and minerals, cream base, lotion matrix, ointment matrix, etc. These matrixes include suspensions, viscosity increasers, transdermal promoters, etc. Their formulations are well known to the artisan in the cosmetic or topical drug field.

The term "excipient" usually refers to a carrier, diluent and/or medium required for the preparation of an effective pharmaceutical composition.

The term "comprise" and English variants thereof (such as comprises or comprising) should be understood as open and non-exclusive meanings, i.e. "including but not limited to".

The term "treating" or "treatment" means that the compound or formulation of the present application is administrated to prevent, ameliorate or eliminate diseases, or one or more symptoms associated with said diseases, and comprises:

(i) preventing the occurrence of a disease or condition in mammals, particularly when such mammals are susceptible to the disease or the condition, but have not yet been diagnosed as suffering from said disease or condition;

(ii) inhibiting a disease or condition, i.e., suppressing the development of the disease or condition;

(iii) alleviating a disease or condition, i.e., causing the regression of the disease or condition.

For a drug or pharmacological active agent, the term "effective amount" or "therapeutically effective amount" refers to a sufficient amount of a drug or formulation that can achieve desired effects but is non-toxic. For the oral formulation of the present invention, "an effective amount" of one active substance in the composition refers to the amount required to achieve a desired effect in combination with another active substance in the composition. The determination of an effective amount varies among individuals, depending on the age and general condition of a subject, as well as the specific active substance. An appropriate effective amount in individual cases can be determined by the person skilled in the art according to conventional tests.

The term "active ingredient", "therapeutic agent", "active substance" or "active agent" refers to a chemical entity, which can effectively treat a target disorder, disease or condition.

"Optional" or "optionally" means that the subsequent event or condition may occur but not requisite, that the term includes the instance in which the event or condition occurs and the instance in which the event or condition does not occur.

The term "substituted" refers to any one or more hydrogen atoms on a specific atom are substituted with a substituent, including deuterium and variants of hydrogen, as long as the valence state of the specific atom is normal and the substituted compound is stable. When the substituent is a oxygen (i.e. =O), it means that two hydrogen atoms are substituted. The substitution of a oxygen does not occur in an aryl. The term "optionally substituted" means that it may be substituted or unsubstituted, and unless otherwise specified, the type and number of substituents can be arbitrary on the chemically realizable basis.

Cm-n herein means that this moiety has an integer number of carbon atoms in a given range. For example, "$C_{1-6}$" means that the group may have 1 carbon atom, 2 carbon atoms, 3 carbon atoms, 4 carbon atoms, 5 carbon atoms or 6 carbon atoms. For example, $C_{1-3}$ means that the group may have 1 carbon atom, 2 carbon atoms, or 3 carbon atoms.

When any variable (e.g. R) occurs more than one time in the composition or structure of a compound, the definition in each occurrence is independent. Therefore, for example, if a group is substituted by 0-2 of R, the group may optionally be substituted by at most two R, and R in each case has an independent option. In addition, the combination of substituents and/or their variants is allowed only if such a combination will lead to a stable compound.

When a substituent is absent, it means that the substituent is not present. For example, when X in A-X is absent, it means that the structure is actually A.

When the atom through which an enumerated substituent is linked to the group to be substituted is not designated, such substituent can be bonded through any atom thereof. For example, pyridyl as a substituent can be linked to the group to be substituted through any carbon atom on the pyridine ring. When an enumerated linking group does not indicate its linking direction, the linking direction is arbitrary. For example, the linking group L in

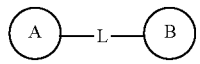

is -M-W—, then -M-W— can link ring A and ring B to form

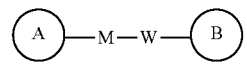

in the direction same as left-to-right reading order, and form

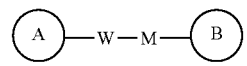

in the direction contrary to left-to-right reading order. The combination of the linking groups, substituents and/or their variants is allowed only if such a combination will lead to a stable compound.

Unless otherwise specified, the term "hetero" represents a heteroatom or a heteroatom group (i.e. a group containing a heteroatom), including atoms except for carbon (C) and hydrogen (H) and groups containing these heteroatoms, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and optionally substituted —C(=O)N(H)—, —N(H)—, —C(=NH)—, —S(=O)$_2$N(H)— or —S(=O)N(H)—.

Unless otherwise specified, the number of the atoms in the ring is usually defined as the of number of the member of the ring, for example, "5- to 7-membered ring" is a ring looped with 5 to 7 atoms.

Unless otherwise specified, the "ring" represents substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a linked ring, a spiro ring, a fused ring or a bridged ring. Unless otherwise specified, the ring optionally contains 1-3 of heteroatoms. Therefore, "5- to 7-membered ring" includes, for example, phenyl, pyridinyl and piperidinyl; on the other hand, the term "5- to 7-membered heterocycloalkyl" includes pyridyl and piperidinyl, but does not include phenyl. The term "ring" also includes a ring system containing at least one ring, wherein each "ring" independently meets the above definition.

Unless otherwise specified, the term "hydrocarbyl" refers to a functional group containing only two kinds of atoms, carbon and hydrogen, the term "hydrocarbyl" or its specific terms (such as alkyl, alkenyl, alkynyl, aryl, etc.) themself or as a part of another substituent represent a linear, branched or cyclic hydrocarbon group or a combination thereof, which may be completely saturated (such as alkyl), or mono- or poly-unsaturated (such as alkenyl, alkynyl and aryl), may be monosubstituted or multi substituted, may be monovalent (e.g., methyl), divalent (e.g., methylene) or multivalent (e.g., methine), may include bivalent or multivalent atomic groups, and have a specified number of carbon atoms (for example, $C_1$-$C_{12}$ represents 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$, and $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes but not limited to aliphatic hydrocarbyl and aromatic hydrocarbyl. The aliphatic hydrocarbyl includes linear and cyclic aliphatic hydrocarbyl, and specifically includes but not limited to alkyl, alkenyl and alkynyl. The aromatic hydrocarbyl includes but not limited to 6- to 12-membered aromatic hydrocarbyl, such as phenyl, naphthyl and the like. In some embodiments, the term "hydrocarbyl" represents a linear or branched atomic group or a combination thereof, which may be completely saturated, or mono- or poly-unsaturated, and may include divalent and polyvalent groups. Examples of saturated hydrocarbon groups include but not limited to homologues or isomers of methyl, ethyl, n-propyl, isopropyl, n-butyl, tert-butyl, iso-butyl, sec-butyl, isobutyl, cyclohexyl, (cyclohexyl)methyl, cyclopropyl methyl, and n-amyl, n-hexyl, n-heptyl, n-octyl and the like. Unsaturated hydrocarbyl has one or more double bonds or triple bonds, and its examples include but not limited to vinyl, 2-propenyl, butenyl, crotyl, 2-isopentenyl, 2-butadienyl, 2,4-pentadienyl, 3-(1,4-pentadienyl), acetenyl, 1- and 3-propinyl, 3-butynyl, and the like, and higher homologs and isomers.

Unless otherwise specified, the term "alkyl" refers to a straight or branched saturated hydrocarbyl, which may be monosubstituted (e.g., —$CH_2F$) or multi substituted (e.g., —$CF_3$), and may be monovalent (e.g., methyl), divalent (e.g., methylene) or multivalent (e.g., methine). Examples of alkyl include methyl (Me), ethyl (Et), propyl (e.g., n-propyl and isopropyl), butyl (e.g., n-butyl, isobutyl, s-butyl, and t-butyl), pentyl (e.g., n-pentyl, isopentyl, and neopentyl), and the like.

Unless otherwise specified, the term "halo" or "halogen" per se or as the part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Unless otherwise specified, Examples of haloalkyl include, but are not limited to, trifluoromethyl, trichloromethyl, pentafluoroethyl and pentachloroethyl.

The term "alkoxy" refers to an alkyl group as defined above with the indicated number of carbon atoms attached through an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but are not limited to methoxy, ethoxy, n-propoxy, isopropoxy, n-butoxy, sec-butoxy, tert-butoxy, n-pentyl oxy and k-pentoxy.

Unless otherwise specified, the term "aryl" represents a polyunsaturated aromatic hydrocarbon substituent, which may be monosubstituted or multi-substituted, and may be monovalent, divalent or multivalent. It may be monocyclic or polycyclic (for example, 1-3 rings; wherein at least one ring is aromatic). They are fused together or connected covalently. For example, the term "heteroaryl" refers to an aryl (or ring) containing 1, 2, 3 or 4 heteroatoms, or the number of heteroatoms of any numerical range formed by 1, 2, 3 or 4. In an exemplary embodiment, the heteroatom is selected from the group consisting of B, N, O, and S, wherein the nitrogen and sulfur atoms are optionally oxidized, and the nitrogen atoms are optionally quaternized. The heteroaryl may be connected to the rest part of the molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, isothiazolyl, furanyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring systems is selected from the acceptable substituents described below.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate groups, such as mesylate, tosylate, p-bromobenzene sulfonate, p-tosylate; acyl oxy, such as acetoxy, trifluoroacetoxy and so on.

The term "protecting group" includes but not limited to "amino protecting groups", "hydroxyl protecting groups", and "mercapto protecting groups". The term "amino protecting groups" refers to a protecting group that is suitable for preventing side reactions from occurring at the nitrogen atom of an amino group. A representative amino protecting group includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenylmethyl (Tr), 1,1-bis-(4'-methoxyphenyl)methyl; silyl, such as trimethylsilyl (TMS) and tert-butyldimethylsilyl (TBS). The term "hydroxyl protecting groups" refers to a protecting group that is suitable for preventing side reactions of a hydroxyl group. A representative hydroxyl protecting group includes but not limited to: alkyl, such as methyl, ethyl, and tert-butyl; acyl, such as alkanoyl (such as acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The compound of the present invention can be prepared through many synthetic methods which are well-known to the person skilled in the art, including the specific embodiments listed below, embodiments obtained by combining the specific embodiments with other chemical synthetic methods and the equivalent alternative methods which are well-known to the person skilled in the art. The preferred embodiments include but not limited to the examples of the present invention.

The solvents used in the present application are commercially available.

The following abbreviations are used in the present application: DMF represents N, N-dimethylformamide; $Na_2CO_3$ represents sodium carbonate; $K_2CO_3$ represents potassium carbonate; $Cs_2CO_3$ represents cesium carbonate; CuI represents cuprous iodide; MeI represents iodomethane; EtOAc represents ethyl acetate; EA represents ethyl acetate; THF represents tetrahydrofuran; LiHMDS represents lithium hexamethyldisilylamide; MeOH represents methanol; DCM represents dichloromethane; DMSO represents dimethyl sulfoxide; PE represents petroleum ether; EtOH represents ethanol; IPA represents isopropanol; $CH_3CN$ represents acetonitrile; MTBE represents methyl tert-butyl ether; TEA represents trifluoroacetic acid; $NH_3.H_2O$ represents aqueous ammonia; TEA represents triethylamine; DIPEA represents N,N-diisopropylethylamine; $Boc_2O$ represents di-tert-butyl dicarbonate; Boc represents a tert-butoxycarbonyl group which is a protecting group for amino; $NH_2OH$ HCl represents the hydrochloride salt of hydroxylamine; $Pd(PPh_2)Cl_2$ represents bis(triphenylphosphine)palladium chloride; DMP represents Dess-Martin reagent; PIFA represents bis (trifluoroacetoxy)iodobenzene; EDTA represents ethylenediaminetetraacetic acid disodium; LCMS represents liquid-mass spectrometry chromatography; HPLC represents liquid chromatography; SFC represents supercritical fluid chromatography; PO represents intragastric administration; IV represents intravenous administration; QD represents administration once a day; BID represents administration twice a day; MPK represents mg/kg; $T_{1/2}$ represents half-life; Vdss represents steady-state apparent volume of distribution; CL represents clearance rate; $AUC_{0-24h}$ represents the area under the plasma concentration-time curve from 0 to 24 hours after administration; $C_{max}$ represents the maximum plasma concentration; $T_{max}$ represents the time after dosing at which the maximum plasma concentration is observed.

DETAIL DESCRIPTION OF THE PREFERRED EMBODIMENTS

Figure 1:
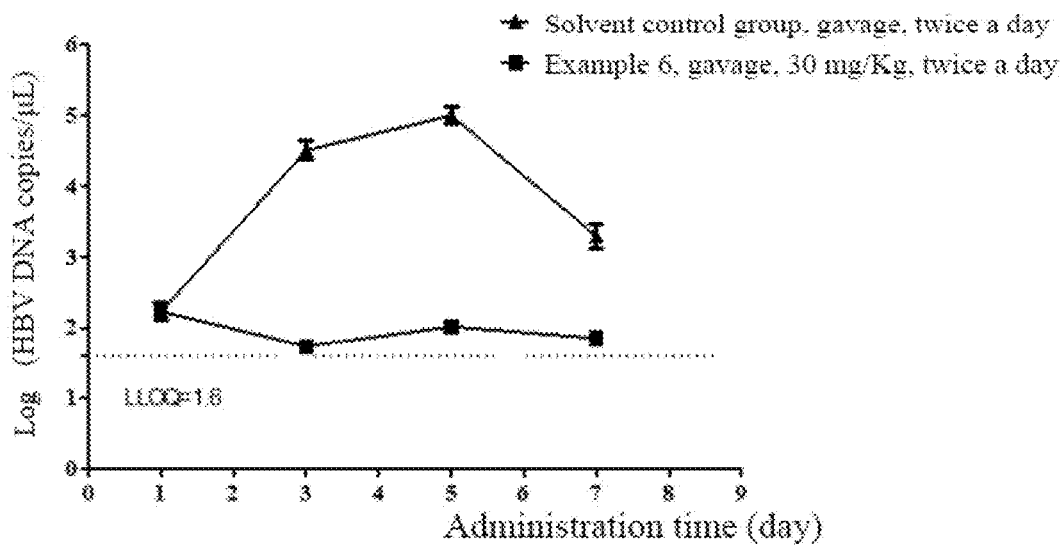
FIG. 1 is a graph showing changes in Log (HBV DNA copy number) per unit volume of plasma from mice in each test group after administration with the compound of Example 6 for 1 to 7 days.

The present invention will be described below in detail with reference to the examples, but the present invention is not limited thereto. While the present invention has been described in detail and the specific embodiments thereof are disclosed herein, it will be apparent to those skilled in the art that various changes and modifications to the specific embodiments in the present invention can be made without departing from the spirit and scope of the present invention.

Preparation of Intermediates

Intermediate A-1

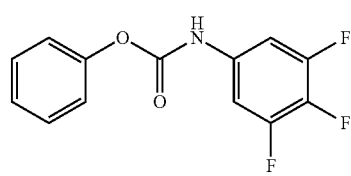

Intermediate A-1 was Prepared by the Following Method:

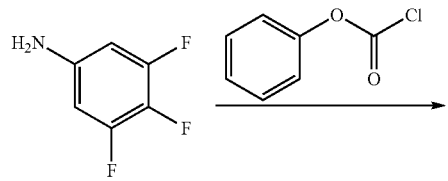

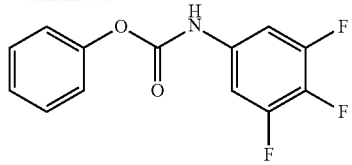

A-1

To a solution of 3,4,5-trifluoroaniline (50.00 g) and pyridine (29.58 g, 30.18 mL) in dichloromethane (300 mL) was slowly added drop wise phenyl chloroformate (58.54 g, 46.83 mL) at 0° C. The reaction mixture was stirred at 25° C. for 3 hours, and then thereto was added 250 mL of water to quench the reaction, and a white precipitate was precipitated out. The precipitate was filtered and then dried under reduced pressure to afford the intermediate A-1.

$^1$H NMR (400 MHz, CDCl$_3$) δ: 7.46-7.39 (m, 2H), 7.32-7.27 (m, 1H), 7.21-7.11 (m, 4H), 4.82 (br. s., 1H); MS(ESI) m/z: 268 [M+H$^+$].

Intermediate A-2

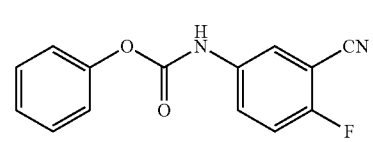

The preparation of intermediate A-2 can be carried out with reference to the preparation method of intermediate A-1, except that 3,4,5-trifluoroaniline was replaced with 3-cyano-4-fluoroaniline.

$^1$H NMR (400 MHz, CDCl$_3$) δ: 7.85-7.74 (m, 1H), 7.67 (dd, J=3.8, 8.3 Hz, 1H), 7.46-7.41 (m, 2H), 7.31-7.18 (m, 5H); MS(ESI) m/z: 257 [M+H$^+$].

Intermediate A-3

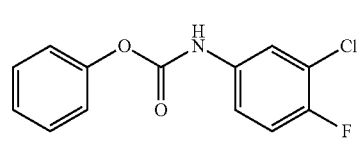

The preparation of intermediate A-3 can be carried out with reference to the preparation method of intermediate A-1, except that 3,4,5-trifluoroaniline was replaced with 3-chloro-4-fluoroaniline.

$^1$H NMR (400 MHz, CDCl$_3$) δ: 7.64 (d, J=4.3 Hz, 1H), 7.51-7.38 (m, 3H), 7.32-7.29 (m, 1H), 7.22-7.10 (m, 3H), 6.95 (br. s., 1H); MS(ESI) m/z: 266 [M+H$^+$].

Intermediate A-4

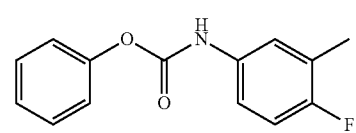

The preparation of intermediate A-4 can be carried out with reference to the preparation method of intermediate A-1, except that 3,4,5-trifluoroaniline was replaced with 3-methyl-4-fluoroaniline.

$^1$H NMR (400 MHz, CDCl$_3$) δ: 7.49-7.33 (m, 3H), 7.28-7.15 (m, 4H), 7.03-6.93 (m, 1H), 6.96 (br.s., 1H), 2.29 (s, 3H). MS(ESI) m/z: 246 [M+H$^+$].

Intermediate A-5

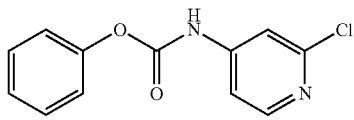

The preparation of intermediate A-5 can be carried out with reference to the preparation method of intermediate A-1, except that 3,4,5-trifluoroaniline was replaced with 2-chloro-4-aminopyridine.

$^1$H NMR (400 MHz, CDCl$_3$) δ: 8.19 (d, J=5.6 Hz, 1H), 7.46 (d, J=1.6 Hz, 2H), 7.38-7.31 (m, 2H), 7.25-7.20 (m, 2H), 7.10 (d, J=7.7 Hz, 2H). MS(ESI) m/z: 249 [M+H$^+$].

Intermediate A-6

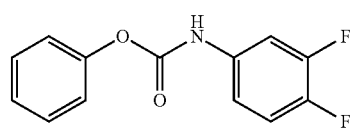

The preparation of intermediate A-6 can be carried out with reference to the preparation method of intermediate A-1, except that 3,4,5-trifluoroaniline was replaced with 3,4-difluoroaniline.

$^1$H NMR (400 MHz, CDCl$_3$) δ: 7.55-7.47 (m, 1H), 7.45-7.40 (m, 2H), 7.32-7.26 (m, 2H), 7.21-7.20 (m, 1H), 7.17-7.01 (m, 3H). MS(ESI) m/z: 250 [M+H$^+$].

Example 1

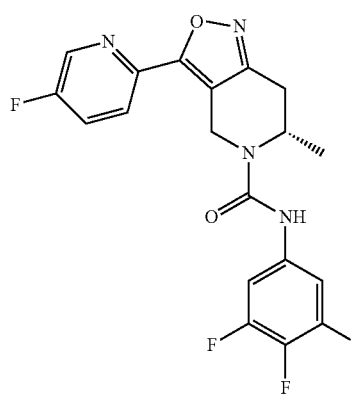

Preparation of Example 1

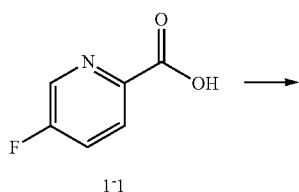

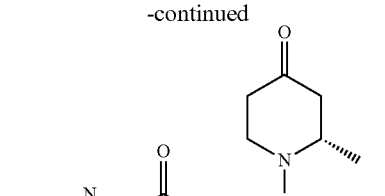

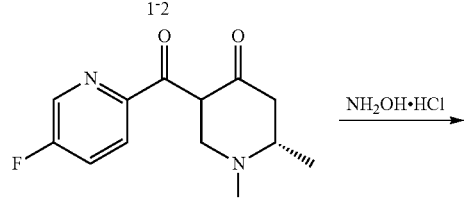

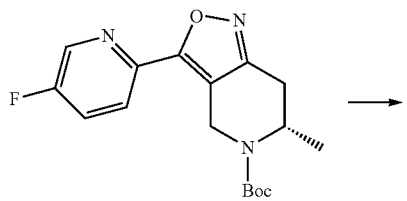

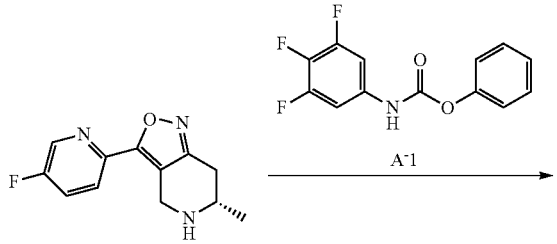

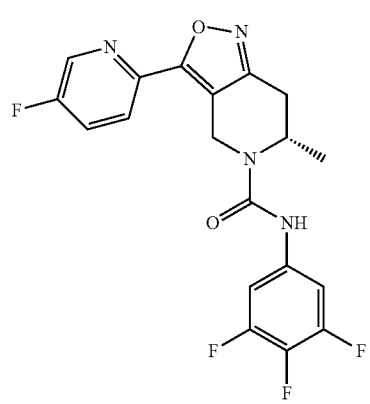 [SMILES: C[C@H]1Cc2noc(-c3ccc(F)cn3)c2CN1C(=O)Nc1cc(F)c(F)c(F)c1]

Example 1

Step A: Synthesis of Compound 1-2

To a solution of Compound 1-1 (3.00 g) in dichloromethane (30 mL) was added oxalyl chloride (5.40 g, 42.52 mol) at 0° C., and then 1 to 2 drops of N,N-dimethylformamide was added. The reaction mixture was naturally warmed to room temperature, and continuously stirred for 14 hours. Then the resulting mixture was concentrated under reduced pressure to afford a crude product of compound 1-2.

Step B: Synthesis of Compound 1-3

N-Boc-(S)-2-methyl-4-piperidinone (0.50 g) was dissolved in diethyl ether (8 mL) at −70° C. under nitrogen gas protection, and then thereto was added lithium hexamethyldisilazide (2.34 mL, 1 mol/L). The reaction mixture was stirred at −70° C. for 0.5 h, and then to the system was added dropwise a solution of Compound 1-2 (374.04 mg) in diethyl ether (2 mL). The resulting reaction mixture was naturally warmed to room temperature and continuously stirred for 3 hours. The reaction solution was then poured into 1 mol/L hydrochloric acid (40 mL) and extracted with ethyl acetate (25 mL×2). The combined organic phase was washed with a saturated saline solution (40 mL), dried over anhydrous sodium sulfate and filtered, and then the filtrate was concentrated under reduced pressure to afford a crude product of compound 1-3.

Step C: Synthesis of Compound 1-4

To 2.5 mL of ethanol were added sequentially compound 1-3 (300.00 mg, crude), hydroxylamine hydrochloride (334.69 mg) and pyridine (2.5 mL) under stirring. The reaction mixture was gradually warmed to 100° C. and stirred at this temperature for 1 hour. After natural cooling, the mixture was distilled under reduced pressure, and the residue was diluted with ethyl acetate (30 mL), and then washed sequentially with 1 mol/L hydrochloric acid (20 mL) and a saturated saline solution (20 mL). The organic phase was dried over anhydrous sodium sulfate and filtered, and then the filtrate was concentrated under reduced pressure. The residue was separated by preparative TLC plate (developer: petroleum ether:ethyl acetate=2:1) to afford compound 1-4.

$^1$H NMR (400 MHz, CDCl$_3$) δ: 8.63-8.48 (m, 1H), 7.92 (dd, J=4.2, 8.6 Hz, 1H), 7.60-7.45 (m, 1H), 5.96-4.79 (m, 1H), 4.58-4.21 (m, 1H), 3.29-3.05 (m, 1H), 3.02-2.72 (m, 2H), 1.59-1.35 (m, 12H). MS(ESI) m/z: 334 [M+H$^+$].

Step D: Synthesis of Compound 1-5

To a solution of hydrochloric acid in 1,4-dioxane (4 mol/L, 5 mL) was added compound 1-4 (93.00 mg) at room temperature. The reaction mixture was stirred at room temperature for 0.5 h, and then distilled under reduced pressure to afford a crude product of compound 1-5 (hydrochloride salt), which was used directly in the next step.

MS(ESI) m/z: 234 [M+H+].

Step E: Synthesis of Example 1

Compound 1-5 (hydrochloride salt, 75.00 mg) was dissolved in 2 mL of N, N-dimethylformamide at room temperature, and then thereto were sequentially added N,N-diisopropylethylamine (107.82 mg) and intermediate A-1 (74.31 mg). The reaction mixture was stirred at 70° C. for 1 hour, and then slowly poured into 30 mL of water and then extracted with ethyl acetate (20 mL of ×2). The combined organic phase was washed with a saturated saline solution (30 mL), dried over anhydrous sodium sulfate and filtered, and the filtrate was concentrated under reduced pressure. The residue was purified by preparative high performance liquid chromatography (separation column: Phenomenex Synergi C18, 150×30 mm×4 μm, mobile phase: [water (0.225% trifluoroacetic acid)-acetonitrile]; B %: 50%-80%, 10.5 min) to afford Example 1.

$^1$HNMR (400 MHz, CD$_3$OD) δ: 8.63 (d, J=2.8 Hz, 1H), 8.00-7.96 (m, 1H), 7.78-7.75 (m, 1H), 7.34-7.14 (m, 2H), 5.29 (d, J=17.5 Hz, 1H), 4.95 (quin, J=6.4 Hz, 1H), 4.50 (d, J=17.4 Hz, 1H), 3.06 (dd, J=5.7, 16.4 Hz, 1H), 2.87 (dd, J=1.2, 16.3 Hz, 1H), 1.22 (d, J=7.0 Hz, 3H).

MS(ESI) m/z: 407 [M+H$^+$].

Example 2

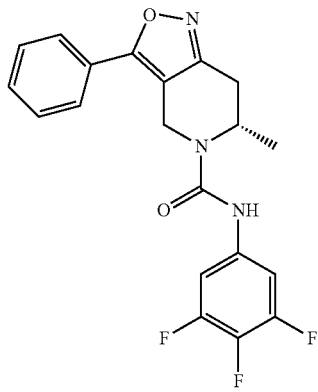 [SMILES: C[C@H]1Cc2noc(-c3ccccc3)c2CN1C(=O)Nc1cc(F)c(F)c(F)c1]

The preparation of Example 2 can be carried out with reference to the preparation procedures A to E of Example 1, except that 5-fluoropyridine-2-carboxylic acid was replaced with benzoic acid. The crude product was separated by preparative SEC (SEC separation method: separation column: DAICEL CHIRALPAK AS-H (dimension: 250 mm×30 mm, particle size: 5 μm); mobile phase: [0.1% NH$_3$.H$_2$O, EtOH]; B %: 30%-30%, 7.8 min) to afford Example 2.

$^1$HNMR (400 MHz, CD$_3$OD) δ: 7.86-7.77 (m, 2H), 7.69-7.48 (m, 3H), 7.36-7.21 (m, 2H), 5.21 (d, J=15.94 Hz, 1H), 4.65-4.47 (m, 2H), 3.17-3.02 (m, 1H), 2.90 (dd, J=1.44, 16.38 Hz, 1H), 1.27 (d, J=6.90 Hz, 3H). MS(ESI) m/z: 388 [M+H$^+$].

Example 3

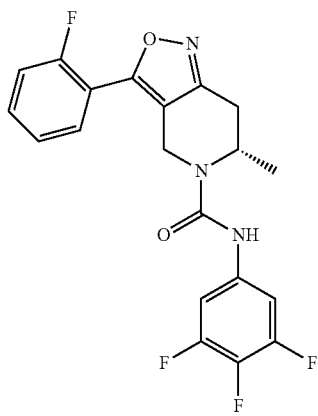 [SMILES: C[C@H]1Cc2noc(-c3ccccc3F)c2CN1C(=O)Nc1cc(F)c(F)c(F)c1]

The preparation of Example 3 can be carried out with reference to the preparation procedures A to E of Example 1, except that 5-fluoropyridine-2-carboxylic acid was replaced with 2-fluorobenzoic acid. The crude product was separated by preparative SEC (SEC separation method: separation column: DAICEL CHIRALPAK AD (dimension: 250 mm×30 mm, particle size: 10 μm; mobile phase: [0.1% NH$_3$H$_2$O, MeOH]; B %: 20%-20%, 4.0 min) to afford Example 3.

¹H NMR (400 MHz, CD₃OD) δ: 7.81 (dt, J=1.63, 7.53 Hz, 1H), 7.67-7.54 (m, 1H), 7.43-7.20 (m, 4H), 5.10 (d, J=16.69 Hz, 1H), 4.92-4.78 (m, 1H), 4.38 (d, J=16.81 Hz, 1H), 3.10 (dd, J=5.90, 16.56 Hz, 1H), 2.91 (d, J=16.31 Hz, 1H), 1.29 (d, J=6.90 Hz, 3H).
MS(ESI) m/z: 406 [M+H⁺].

Example 4

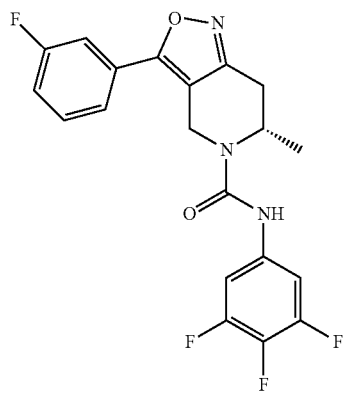 [SMILES: C[C@H]1Cc2noc(-c3cccc(F)c3)c2CN1C(=O)Nc1cc(F)c(F)c(F)c1]

The preparation of Example 4 can be carried out with reference to the preparation procedures A to E of Example 1, except that 5-fluoropyridine-2-carboxylic acid was replaced with 3-fluorobenzoic acid. The crude product was separated by preparative SEC (SEC separation method: separation column: DAICEL CHIRALPAK AS (dimension: 250 mm×50 mm, particle size: 10 μm); mobile phase: [0.1% NH₃.H₂O, IPA]; B %: 50%-50%, 1.9 min) to afford Example 4.

¹H NMR (400 MHz, CD₃OD) δ: 7.62-7.56 (m, 2H), 7.52 (dd, J=1.3, 8.7 Hz, 1H), 7.31-7.21 (m, 3H), 5.16 (d, J=16.1 Hz, 1H), 4.99 (quin, J=6.3 Hz, 1H), 4.49 (d, J=16.1 Hz, 1H), 3.09-3.00 (m, 1H), 2.92-2.83 (m, 1H), 1.23 (d, J=6.8 Hz, 3H). MS(ESI) m/z: 406 [M+H⁺].

Example 5

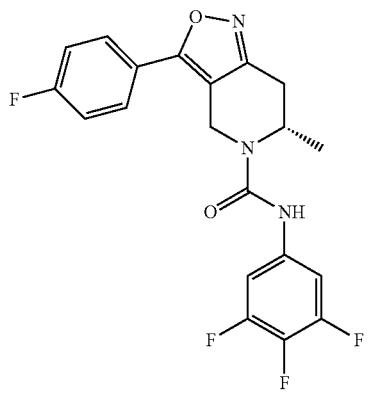 [SMILES: C[C@H]1Cc2noc(-c3ccc(F)cc3)c2CN1C(=O)Nc1cc(F)c(F)c(F)c1]

The preparation of Example 5 can be carried out with reference to the preparation procedures A to E of Example 1, except that 5-fluoropyridine-2-carboxylic acid was replaced with 4-fluorobenzoic acid. The crude product was separated by preparative SEC (SEC separation method: separation column: DAICEL CHIRALPAK AS-H (dimension: 250 mm×30 mm, particle size: 5 μm); mobile phase: [0.1% NH₃.H₂O, EtOH]; B %: 30%-30%, 4.2 min) to afford Example 5.

¹H NMR (400 MHz, CD₃OD) δ: 7.90-7.80 (m, 2H), 7.42-7.23 (m, 4H), 5.24-5.14 (m, 1H), 5.01 (quin, J=6.3 Hz, 1H), 4.50 (d, J=16.1 Hz, 1H), 3.08 (dd, J=5.8, 16.3 Hz, 1H), 2.89 (dd, j=1.2, 16.4 Hz, 1H), 1.26 (d, J=6.9 Hz, 3H).
MS(ESI) m/z: 406 [M+H⁺].

Example 6

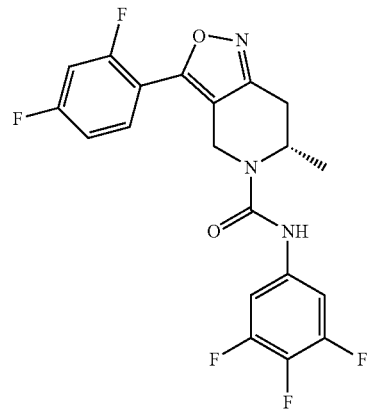 [SMILES: C[C@H]1Cc2noc(-c3ccc(F)cc3F)c2CN1C(=O)Nc1cc(F)c(F)c(F)c1]

The preparation of Example 6 can be carried out with reference to the preparation procedures A to E of Example 1, except that 5-fluoropyridine-2-carboxylic acid was replaced with 2,4-difluorobenzoic acid. The crude product was separated by preparative SFC (SFC separation method: separation column: DAICEL CHIRALPAK AS (dimension: 250 mm×30 mm, particle size: 10 μm); mobile phase: [0.1% NH₃.H₂O, IPA]; B %: 30%-30%, 9 min) to afford Example 6.

¹H NMR (400 MHz, CD₃OD) δ: 7.86-7.75 (m, 1H), 7.26-7.14 (m, 4H), 5.05 (d, J=16.4 Hz, 1H), 4.93 (quin, J=6.4 Hz, 1H), 4.38-4.27 (m, 1H), 3.06 (dd, J=5.9, 16.4 Hz, 1H), 2.91-2.82 (m, 1H), 1.25 (d, J=6.9 Hz, 3H). MS(ESI) m/z: 424 [M+H⁺].

Example 7

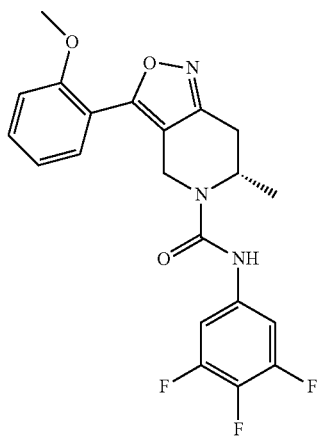 [SMILES: COc1ccccc1-c1onc2c1CN(C(=O)Nc1cc(F)c(F)c(F)c1)[C@@H](C)C2]

The preparation of Example 7 can be carried out with reference to the preparation procedures A to E of Example 1, except that 5-fluoropyridine-2-carboxylic acid was replaced with 2-methoxybenzoic acid. The crude product was separated by preparative SFC (SFC separation method: separation column: DAICEL CHIRALPAK AD (dimension: 250 mm×30 mm, particle size: 10 μm); mobile phase: [0.1% NH$_3$.H$_2$O, MeOH]; B %: 30%-30%, 2.5 min) to afford Example 7.

$^1$H NMR (400 MHz, CD$_3$OD) δ: 7.60 (dd, J=1.6, 7.6 Hz, 1H), 7.53-7.45 (m, 1H), 7.25-7.12 (m, 3H), 7.07 (t, J=7.5 Hz, 1H), 4.99 (d, J=16.6 Hz, 1H), 4.94-4.88 (m, 1H), 4.24 (d, J=16.6 Hz, 1H), 3.94 (s, 3H), 3.04 (dd, J=5.9, 16.4 Hz, 1H), 2.83 (dd, J=1.0, 16.3 Hz, 1H), 1.26 (d, J=6.8 Hz, 3H). MS(ESI) m/z: 418 [M+H$^+$].

Example 8

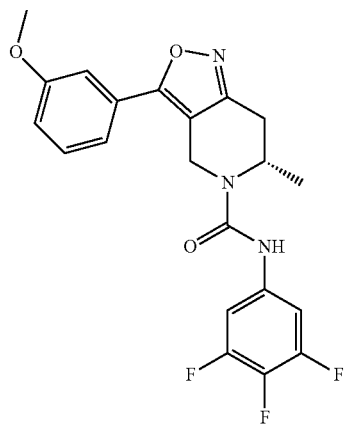 [SMILES: COc1cccc(-c2onc3c2CN(C(=O)Nc2cc(F)c(F)c(F)c2)[C@@H](C)C3)c1]

The preparation of Example 8 can be carried out with reference to the preparation procedures A to E of Example 1, except that 5-fluoropyridine-2-carboxylic acid was replaced with 3-methoxybenzoic acid. The crude product was separated by preparative SFC (SFC separation method: separation column: DAICEL CHIRALPAK AD (dimension: 250 mm×30 mm, particle size: 10 μm); mobile phase: [0.1% NH$_3$.H$_2$O, EtOH]; B %: 30%-30%, 3.0 min) to afford Example 8.

$^1$H NMR (400 MHz, CD$_3$OD): δ 7.51-7.43 (m, 1H), 7.34-7.23 (m, 4H), 7.07 (dd, J=2.1, 8.2 Hz, 1H), 5.15 (d, J=16.1 Hz, 1H), 4.97 (quin, J=6.4 Hz, 1H), 4.47 (d, J=16.0 Hz, 1H), 3.88 (s, 3H), 3.05 (dd, J=5.7, 16.3 Hz, 1H), 2.86 (dd, 7=1.1, 16.3 Hz, 1H), 1.24 (d, J=6.8 Hz, 3H). MS(ESI) m/z: 418 [M+H$^+$].

Example 9

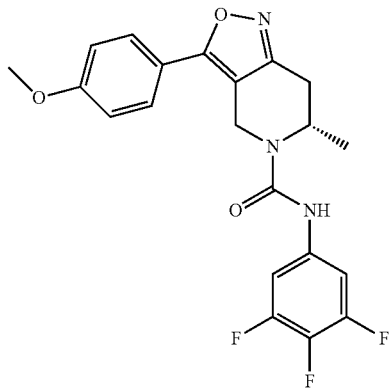 [SMILES: COc1ccc(-c2onc3c2CN(C(=O)Nc2cc(F)c(F)c(F)c2)[C@@H](C)C3)cc1]

The preparation of Example 9 can be carried out with reference to the preparation procedures A to E of Example 1, except that 5-fluoropyridine-2-carboxylic acid was replaced with 4-methoxybenzoic acid. The crude product was separated by preparative SFC (SFC separation method: separation column: DAICEL CHIRALCEL OD (dimension: 250 mm×50 mm, particle size: 10 μm); mobile phase: [0.1% NH$_3$.H$_2$O, IPA]; B %: 30%-30%, 4.2 min) to afford Example 9.

$^1$H NMR (400 MHz, CD$_3$OD) δ: 7.75 (d, J=8.9 Hz, 2H), 7.33-7.25 (m, 2H), 7.14 (d, J=9.0 Hz, 2H), 5.16 (d, J=15.8 Hz, 1H), 5.05-4.97 (m, 1H), 4.48 (d, J=15.9 Hz, 1H), 3.90 (s, 3H), 3.06 (dd, J=5.6, 16.4 Hz, 1H), 2.87 (d, J=16.3 Hz, 1H), 1.26 (d, J=6.9 Hz, 3H).

MS(ESI) m/z: 418 [M+H$^+$].

Example 10

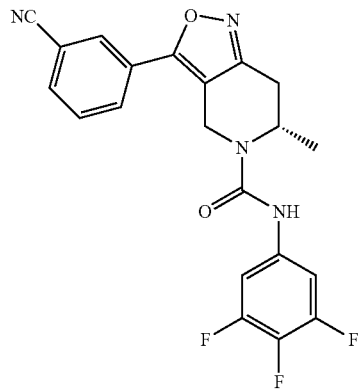 [SMILES: C[C@H]1Cc2noc(-c3cccc(C#N)c3)c2CN1C(=O)Nc1cc(F)c(F)c(F)c1]

The preparation of Example 10 can be carried out with reference to the preparation procedures A to E of Example 1, except that 5-fluoropyridine-2-carboxylic acid was replaced with 3-cyanobenzoic acid. The crude product was separated by preparative SFC (SFC separation method: separation column: DAICEL CHIRALPAK AD (dimension: 250 mm×30 mm, particle size: 10 μm); mobile phase: [0.1% NH$_3$.H$_2$O, IPA]; B %: 30%-30%, 3.1 min) to afford Example 10.

$^1$H NMR (400 MHz, CD$_3$OD) δ: 8.17-8.06 (m, 2H), 7.88 (d, J=7.8 Hz, 1H), 7.81-7.72 (m, 1H), 7.33-7.22 (m, 2H), 5.23 (d, J=16.3 Hz, 1H), 5.08-4.96 (m, 1H), 4.62-4.58 (m, 1H), 3.09 (dd, J=5.7, 16.4 Hz, 1H), 2.91 (dd, J=1.3, 16.3 Hz, 1H), 1.26 (d, J=6.9 Hz, 3H).
MS(ESI) m/z: 413 [M+H$^+$].

Example 11

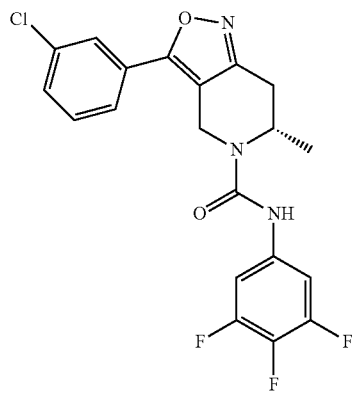 [SMILES: C[C@H]1Cc2noc(-c3cccc(Cl)c3)c2CN1C(=O)Nc1cc(F)c(F)c(F)c1]

The preparation of Example 11 can be carried out with reference to the preparation procedures A to E of Example 1, except that 5-fluoropyridine-2-carboxylic acid was replaced with 3-chlorobenzoic acid. The crude product was separated by preparative SFC (SFC separation method: separation column: DAICEL CHIRALPAK AS-H (dimension: 250 mm×30 mm, particle size: 5 μm); mobile phase: [0.1% NH$_3$.H$_2$O, MeOH]; B %: 35%-35%, 5 min) to afford Example 11.
$^1$HNMR (400 MHz, CD$_3$OD) δ: 7.71-7.55 (m, 2H), 7.51-7.38 (m, 2H), 7.16 (dd, J=6.3, 10.3 Hz, 2H), 5.08 (d, J=16.0 Hz, 1H), 4.94-4.82 (m, 1H), 4.50-4.37 (m, 1H), 3.04-2.91 (m, 1H), 2.78 (br. d, J=16.4 Hz, 1H), 1.14 (d, J=6.8 Hz, 3H). MS(ESI) m/z: 422 [M+H$^+$].

Example 12

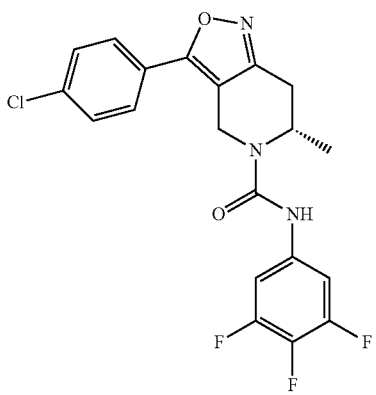 [SMILES: C[C@H]1Cc2noc(-c3ccc(Cl)cc3)c2CN1C(=O)Nc1cc(F)c(F)c(F)c1]

The preparation of Example 12 can be carried out with reference to the preparation procedures A to E of Example 1, except that 5-fluoropyridine-2-carboxylic acid was replaced with 4-chlorobenzoic acid. The crude product was separated by preparative SFC (SFC separation method: separation column: DAICEL CHIRALPAK AS-H (dimension: 250 mm×30 mm, particle size: 5 μm); mobile phase: [0.1% NH$_3$.H$_2$O, EtOH]; B %: 30%-30%, 8.3 min) to afford Example 12.
$^1$H NMR (400 MHz, CD$_3$OD) δ: 7.73-7.63 (m, 2H), 7.52-7.45 (m, 2H), 7.17 (dd, J=6.36, 10.27 Hz, 2H), 5.08 (d, J=16.14 Hz, 1H), 4.94-4.84 (m, 1H), 4.39 (d, J=16.02 Hz, 1H), 2.96 (dd, J=5.75, 16.38 Hz, 1H), 2.78 (dd, J=1.28, 16.32 Hz, 1H), 1.14 (d, J=6.97 Hz, 3H).
MS(ESI) m/z: 422 [M+H$^+$].

Example 13

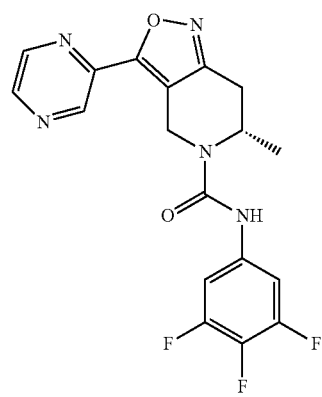 [SMILES: C[C@H]1Cc2noc(-c3cnccn3)c2CN1C(=O)Nc1cc(F)c(F)c(F)c1]

The preparation of Example 13 can be carried out with reference to the preparation procedures A to E of Example 1, except that 5-fluoropyridine-2-carboxylic acid was replaced with pyrazine-2-carboxylic acid. The crude product was separated by preparative SFC (SFC separation method: separation column: DAICEL CHIRALPAK AS-H (dimension: 250 mm×30 mm, particle size: 5 μm); mobile phase: [0.1% NH$_3$.H$_2$O, MeOH]; B %: 60%-60%, 4.5 min) to afford Example 13.
$^1$HNMR (400 MHz, CD$_3$OD) δ: 9.17 (d, J=1.5 Hz, 1H), 8.81 (dd, J=1.6, 2.4 Hz, 1H), 8.67 (d, J 20=2.5 Hz, 1H), 7.32-7.22 (m, 2H), 5.37 (d, J=17.6 Hz, 1H), 5.03-4.96 (m, 1H), 4.57 (d, J=17.7 Hz, 1H), 3.12 (dd, J=5.8, 16.4 Hz, 1H), 2.94 (dd, J=1.4, 16.4 Hz, 1H), 1.26 (d, J=6.9 Hz, 3H).
MS(ESI) m/z: 390 [M+H$^+$].

Example 14

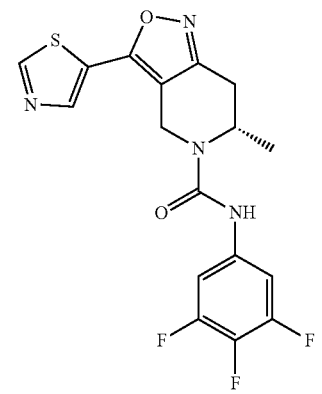 [SMILES: C[C@H]1Cc2noc(-c3cncs3)c2CN1C(=O)Nc1cc(F)c(F)c(F)c1]

The preparation of Example 14 can be carried out with reference to the preparation procedures A to E of Example 1, except that 5-fluoropyridine-2-carboxylic acid was replaced with thiazole-5-carboxylic acid. The crude product was separated by preparative SFC (SFC separation method: separation column: DAICEL CHIRALCEL OD (dimension: 250 mm×30 mm, particle size: 10 μm); mobile phase: [0.1% NH$_3$.H$_2$O, MeOH]; B %: 30%-30%, 2.3 min) to afford Example 14.

$^1$H NMR (400 MHz, CD$_3$OD) δ: 9.12 (s, 1H), 8.26 (s, 1H), 7.24-7.11 (m, 2H), 5.03 (d, J=16.38 Hz, 1H), 4.90 (t, J=6.72 Hz, 1H), 4.33 (d, J=16.38 Hz, 1H), 3.02-2.92 (m, 1H), 2.79 (dd, J=1.41, 16.44 Hz, 1H), 1.14 (d, J=6.85 Hz, 3H). MS(ESI) m/z: 395 [M+H$^+$].

Example 15

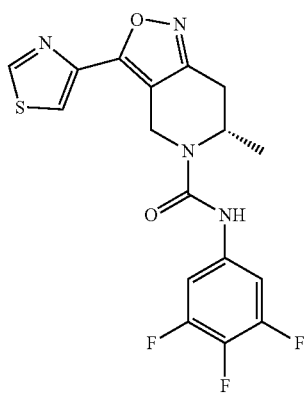 [SMILES: C[C@H]1Cc2noc(-c3cscn3)c2CN1C(=O)Nc1cc(F)c(F)c(F)c1]

The preparation of Example 15 can be carried out with reference to the preparation procedures A to E of Example 1, except that 5-fluoropyridine-2-carboxylic acid was replaced with thiazole-4-carboxylic acid. The crude product was separated by preparative SFC (SFC separation method: separation column: DAICEL CHIRALPAK AD (dimension: 250 mm×30 mm, particle size: 10 μm); mobile phase: [0.1% NH$_3$.H$_2$O, IPA]; B %: 30%-30%, 3.0 min) to afford Example 15.

$^1$H NMR (400 MHz, CD$_3$OD) δ: 9.20 (d, J=2.0 Hz, 1H), 8.18 (d, J=1.9 Hz, 1H), 7.37-7.21 (m, 2H), 5.30 (d, J=16.8 Hz, 1H), 5.05-4.95 (m, 1H), 4.52 (d, J=16.8 Hz, 1H), 3.09 (dd, J=5.7, 16.4 Hz, 1H), 2.90 (d, J=16.3 Hz, 1H), 1.26 (d, J=6.9 Hz, 3H). MS(ESI) m/z: 395 [M+H$^+$].

Example 16

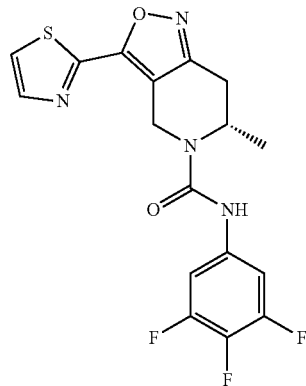 [SMILES: C[C@H]1Cc2noc(-c3nccs3)c2CN1C(=O)Nc1cc(F)c(F)c(F)c1]

The preparation of Example 16 can be carried out with reference to the preparation procedures A to E of Example 1, except that 5-fluoropyridine-2-carboxylic acid was replaced with thiazole-2-carboxylic acid. The crude product was separated by preparative SFC (SFC separation method: separation column: DAICEL CHIRALPAK AS-H (dimension: 250 mm×30 mm, particle size: 5 μm); mobile phase: [0.1% NH$_3$.H$_2$O, MeOH]; B %: 35%-35%, 6.3 min) to afford Example 16.

$^1$HNMR (400 MHz, CD$_3$OD) δ: 9.01 (s, 1H), 7.75 (d, J=4.8 Hz, 1H), 7.16 (dd, J=6.4, 10.3 Hz, 2H), 5.21 (d, J=17.2 Hz, 1H), 4.93-4.84 (m, 1H), 4.50-4.41 (m, 1H), 3.05-2.95 (m, 1H), 2.80 (d, j=16.5 Hz, 1H), 1.14 (d, J=6.8 Hz, 3H). MS(ESI) m/z: 395 [M+H$^+$].

Example 17

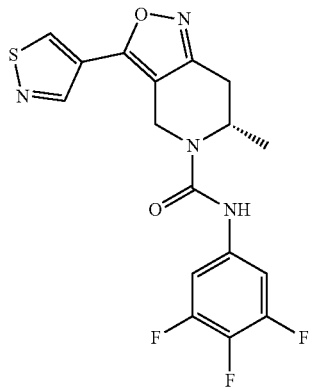 [SMILES: C[C@H]1Cc2noc(-c3cnsc3)c2CN1C(=O)Nc1cc(F)c(F)c(F)c1]

The preparation of Example 17 can be carried out with reference to the preparation procedures A to E of Example 1, except that 5-fluoropyridine-2-carboxylic acid was replaced with isothiazole-4-carboxylic acid. The crude product was separated by preparative SFC (SFC separation method: separation column: DAICEL CHIRALPAK AD (dimension: 250 mm×30 mm, particle size: 10 μm); mobile phase: [0.1% NH$_3$.H$_2$O, IPA]; B %: 30%-30%, 30 min) to afford Example 17.

$^1$HNMR (400 MHz, CD$_3$OD) δ: 9.40 (s, 1H), 9.00 (s, 1H), 7.33-7.27 (m, 2H), 5.18 (d, J=16.0 Hz, 1H), 5.08-5.00 (m,

1H), 4.50 (d, J=16.0 Hz, 1H), 3.08 (dd, J=5.7, 16.4 Hz, 1H), 2.94-2.88 (m, 1H), 1.25 (d, J=7.0 Hz, 3H). MS(ESI) m/z: 395 [M+H$^+$].

Example 18

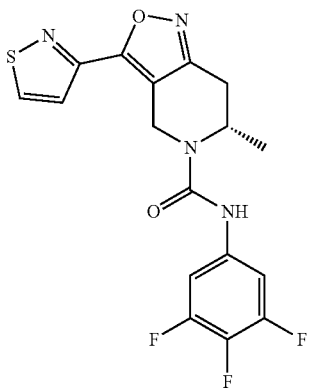 [SMILES: C[C@H]1Cc2noc(-c3ccsn3)c2CN1C(=O)Nc1cc(F)c(F)c(F)c1]

The preparation of Example 18 can be carried out with reference to the preparation procedures A to E of Example 1, except that 5-fluoropyridine-2-carboxylic acid was replaced with isothiazole-3-carboxylic acid. The crude product was separated by preparative SFC (SFC separation method: separation column: DAICEL CHIRALPAK AD-H (dimension: 250 mm×30 mm, particle size: 5 μm); mobile phase: [0.1% NH$_3$.H$_2$O, MeOH]; B %: 35%-35%, 2.1 min) to afford Example 18.

$^1$H NMR (400 MHz, CD$_3$OD) δ: 8.00 (d, J=3.2 Hz, 1H), 7.75 (d, J=3.2 Hz, 1H), 7.20-7.13 (m, 2H), 5.18 (d, J=17.2 Hz, 1H), 4.92-4.85 (m, 1H), 4.51-4.37 (m, 1H), 3.04-2.96 (m, 1H), 2.85-2.78 (m, 1H), 1.14 (d, J=7.0 Hz, 3H). MS(ESI) m/z: 395 [M+H$^+$].

Example 19

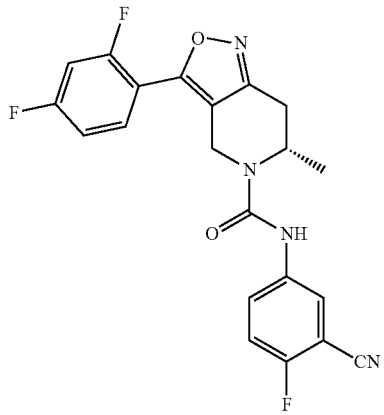 [SMILES: C[C@H]1Cc2noc(-c3ccc(F)cc3F)c2CN1C(=O)Nc1ccc(F)c(C#N)c1]

The preparation process of Example 19 can be carried out with reference to the preparation procedures A to E of Example 1, except that 5-fluoropyridine-2-carboxylic acid was replaced with 2,4-difluorobenzoic acid; and intermediate A-1 was replaced with intermediate A-2. The crude product was separated by preparative SEC (SEC separation method: separation column: DAICEL CHIRALCEL OJ (dimension: 250 mm×30 mm, particle size: 10 μm); mobile phase: [0.1% NH$_3$.H$_2$O, EtOH]; B %: 25%-25%, 2.4 min) to afford Example 19.

$^1$H NMR (400 MHz, CD$_3$OD) δ: 7.89-7.76 (m, 2H), 7.72-7.64 (m, 1H), 7.29-7.16 (m, 3H), 5.08 (d, J=16.4 Hz, 1H), 4.96 (quin, J=6.4 Hz, 1H), 4.36 (d, J=16.6 Hz, 1H), 3.08 (dd, J=5.8, 16.4 Hz, 1H), 2.93-2.85 (m, 1H), 1.27 (d, J=6.8 Hz, 3H). MS(ESI) m/z: 413 [M+H$^+$].

Example 20

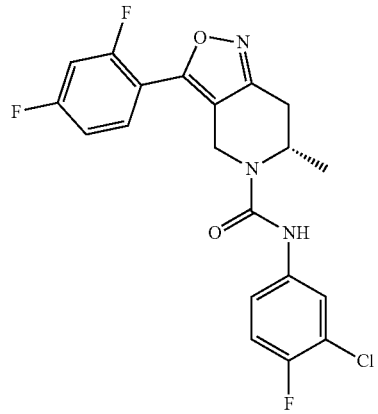 [SMILES: C[C@H]1Cc2noc(-c3ccc(F)cc3F)c2CN1C(=O)Nc1ccc(F)c(Cl)c1]

The preparation process of Example 20 can be carried out with reference to the preparation procedures A to E of Example 1, except that 5-fluoropyridine-2-carboxylic acid was replaced with 2,4-difluorobenzoic acid; and intermediate A-1 was replaced with intermediate A-3. The crude product was separated by preparative SEC (SEC separation method: separation column: DAICEL CHIRALPAK AS (dimension: 250 mm×50 mm, particle size: 10 μm); mobile phase: [0.1% NH$_3$.H$_2$O, MeOH]; B %: 40%-40%, 1.9 min) to afford Example 20.

$^1$H NMR (400 MHz, CD$_3$OD) δ: 7.85-7.79 (m, 1H), 7.59 (dd, J=2.6, 6.8 Hz, 1H), 7.36-7.08 (m, 4H), 5.09 (dd, 7=1.1, 16.6 Hz, 1H), 4.97-4.94 (m, 1H), 4.36 (dd, 7=1.5, 16.6 Hz, 1H), 3.10 (dd, J=5.9, 16.4 Hz, 1H), 2.90 (dd, J=1.3, 16.4 Hz, 1H), 1.28 (d, J=6.9 Hz, 3H).

MS(ESI) m/z: 422 [M+H$^+$].

Example 21

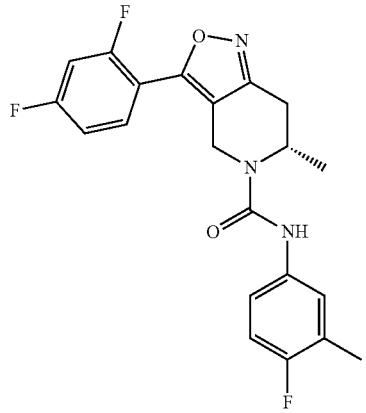 [SMILES: Cc1cc(NC(=O)N2Cc3c(noc3-c3ccc(F)cc3F)C[C@@H]2C)ccc1F]

The preparation of Example 21 can be carried out with reference to the preparation procedures A to E of Example 1, except that 5-fluoropyridine-2-carboxylic acid was replaced with 2,4-difluorobenzoic acid; and intermediate A-1 was replaced with intermediate A-4. The crude product was separated by preparative SEC (SEC separation method: separation column: DAICEL CHIRALPAK AD (dimension: 250 mm×30 mm, particle size: 10 μm); mobile phase: [0.1% NH$_3$.H$_2$O, EtOH]; B %: 20%-20%, 5.5 min) to afford Example 21.

$^1$H NMR (400 MHz, CD$_3$OD) δ: 7.87-7.83 (m, 1H), 7.30-7.10 (m, 4H), 6.96-6.94 (m, 1H), 5.09 (d, J=16.6 Hz, 1H), 5.02-4.94 (m, 1H), 4.35 (d, J=16.4 Hz, 1H), 3.16-3.06 (m, 1H), 2.89 (d, J=16.4 Hz, 1H), 2.24 (s, 3H), 1.28 (d, J=6.9 Hz, 3H). MS(ESI) m/z: 402 [M+H$^+$].

Example 22

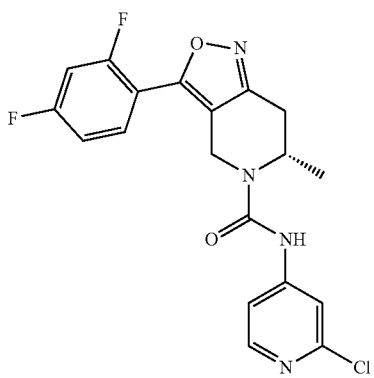 [SMILES: C[C@H]1Cc2noc(-c3ccc(F)cc3F)c2CN1C(=O)Nc1ccnc(Cl)c1]

The preparation of Example 22 can be carried out with reference to the preparation procedures A to E of Example 1, except that 5-fluoropyridine-2-carboxylic acid was replaced with 2,4-difluorobenzoic acid; and intermediate A-1 was replaced with intermediate A-5. The crude product was separated by preparative SEC (SEC separation method: separation column: DAICEL CHIRALPAK AD (dimension: 250 mm×50 mm, particle size: 10 μm); mobile phase: [0.1% NH$_3$.H$_2$O, MeOH]; B %: 30%-30%, 1.8 min) to afford Example 22.

$^1$H NMR (400 MHz, CD$_3$OD) δ: 8.00 (d, J=5.9 Hz, 1H), 7.77-7.69 (m, 1H), 7.53 (d, 7=1.7 Hz, 1H), 7.31 (dd, 7=1.8, 5.7 Hz, 1H), 7.16-7.06 (m, 2H), 4.99 (d, 7=16.5 Hz, 1H), 4.90-4.83 (m, 1H), 4.27 (d, 7=16.6 Hz, 1H), 2.99 (dd, 7=5.9, 16.5 Hz, 1H), 2.79 (d, 7=16.5 Hz, 1H), 1.17 (d, 7=6.8 Hz, 3H). MS(ESI) m/z: 405 [M+H$^+$].

Example 23

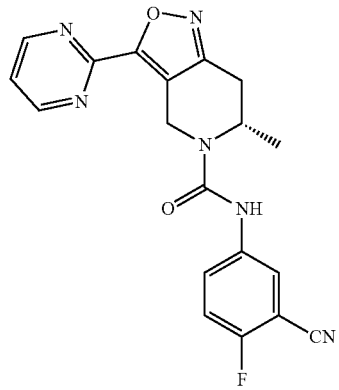 [SMILES: C[C@H]1Cc2noc(-c3ncccn3)c2CN1C(=O)Nc1ccc(F)c(C#N)c1]

Preparation of Example 23

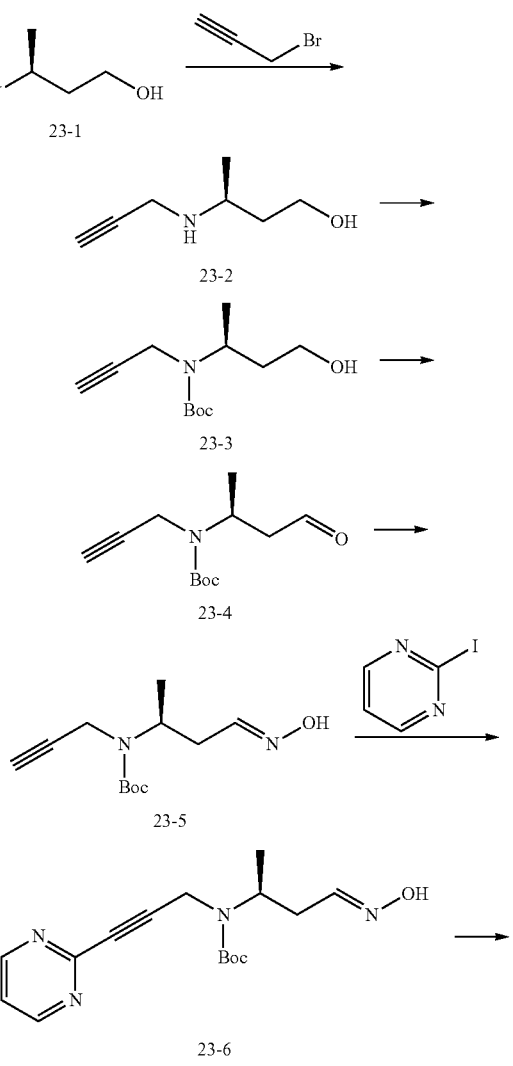

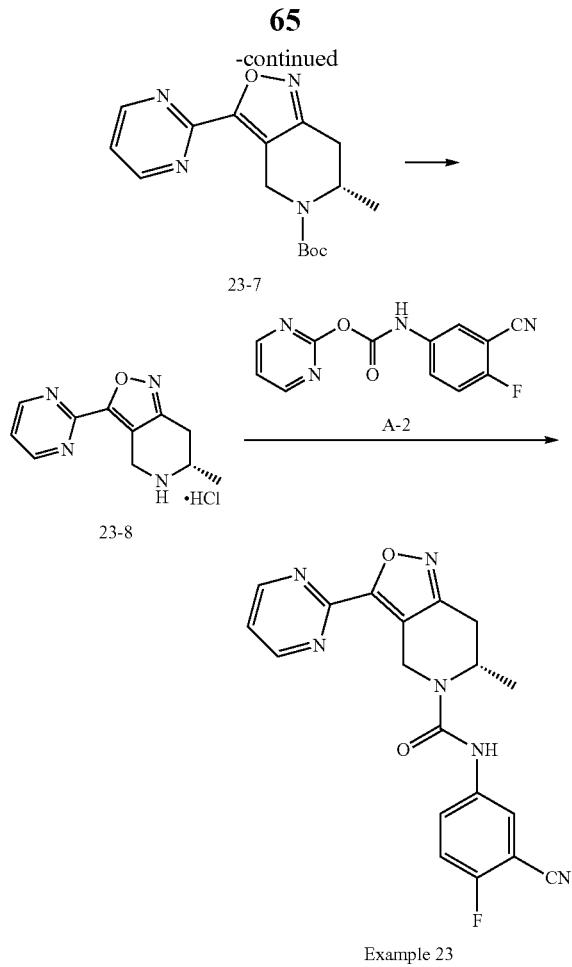

Example 23

Step A: Synthesis of Compound 23-2

To a solution of compound 23-1 (50.0 g) and potassium carbonate (77.53 g) in acetonitrile (500 mL) was added dropwise 3-bromopropyne (66.73 g) at 0° C. The reaction mixture was naturally warmed to room temperature, and continuously stirred for 12 hours. Then the resulting mixture was concentrated under reduced pressure to give a residue. The residue was diluted with water and extracted with ethyl acetate. The combined organic phase was washed with a saturated saline solution, dried over anhydrous sodium sulfate, and filtered. The filtrate was concentrated under reduced pressure to afford a crude product of compound 23-2. MS(ESI) m/z: 128 [M+H$^+$].

Step B: Synthesis of Compound 23-3

To a solution of compound 23-2 (52.0 g) in tetrahydrofuran (500 mL) were added potassium carbonate (26.56 g) and Boc$_2$O (41.94 g) at room temperature. The reaction mixture was stirred at 18° C. for 12 hours, and then filtered to remove the solid. The filtrate was collected and concentrated under reduced pressure. The obtained residue was dissolved in ethyl acetate (800 mL), and the organic phase was washed sequentially with water, a saturated citric acid solution and a saturated sodium bicarbonate solution, dried over anhydrous sodium sulfate, and filtered. The filtrate was concentrated under reduced pressure to obtain a crude product of compound 23-3. MS(ESI) m/z: 228 [M+H$^+$].

Step C: Synthesis of Compound 23-4

To a solution of compound 23-3 (40.0 g) in dichloromethane (400 mL) was added in batches Dess-Martin reagent (82.10 g) at 0° C. The reaction mixture was naturally warmed to room temperature and stirred for 2 hours. Then the mixture was washed twice with a saturated sodium bicarbonate solution and a saturated sodium thiosulfate solution in a volume ratio of 1:1. The organic phase was washed sequentially with a saturated sodium bicarbonate solution and a saturated saline solution, dried over anhydrous sodium sulfate and filtered. The filtrate was concentrated under reduced pressure to afford a crude product of compound 23-4. MS(ESI) m/z: 226 [M+H$^+$].

Step D: Synthesis of Compound 23-5

To a mixture solution of compound 23-4 (42.0 g) in ethanol (400 mL) and water (40 mL) was added sodium acetate (22.94 g) and hydroxylamine hydrochloride (16.84 g) at room temperature. The reaction mixture was stirred at room temperature for 12 hours, and then concentrated under reduced pressure to remove the ethanol, thereby obtaining a residue. The residue was dissolved in ethyl acetate, and then the resulting mixture was washed sequentially with water and a saturated saline solution, dried over anhydrous sodium sulfate, and filtered. The filtrate was concentrated under reduced pressure to afford a crude product of compound 23-5. MS(ESI) m/z: 241 [M+H$^+$].

Step E: Synthesis of Compound 23-6

To a solution of compound 23-5 (300 mg) and 2-iodopyrimidine (257.16 mg) in N,N-dimethylformamide (8 mL) were added copper iodide (11.89 mg), triethylamine (252.66 mg) and bis-triphenylphosphine palladium dichloride (43.81 mg) at room temperature. The reaction mixture was stirred at 12° C. for 12 hours under nitrogen gas protection. The resulting reaction solution was diluted with ethyl acetate, and then filtered. The filtrate was concentrated under reduced pressure, and the residue was separated by preparative TLC plates to afford compound 23-6. MS(ESI) m/z: 319 [M+H$^+$].

Step F: Synthesis of Compound 23-7

To a mixture solution of compound 23-6 (180 mg) in methanol (4 mL) and water (0.8 mL) was added in batches bis(trifluoroacetoxy)iodobenzene (291.76 mg) at room temperature. The reaction mixture was stirred at 10-20° C. for 0.5 h, diluted with 20 mL of water, and then extracted with ethyl acetate. The organic phase was dried over anhydrous sodium sulfate and filtered. The filtrate was concentrated under reduced pressure, and the residue was separated by preparative TLC plate to afford compound 23-7. MS(ESI) m/z: 317 [M+H$^+$].

Step G: Synthesis of Compound 23-8

Compound 23-7 (90 mg) was dissolved in a solution of hydrochloric acid in dioxane (4 mol/L, 4 mL). The reaction mixture was stirred at 20° C. for 0.5 hour, and then concentrated under reduced pressure to afford a crude product of compound 23-8. MS(ESI) m/z: 217 [M+H$^+$].

Step H: Synthesis of Example 23

To a solution of compound 23-8 (61.52 mg) in N,N-dimethylformamide (2 mL) were added A,TV-diisopropyl ethylamine (110.31 mg) and intermediate A-2 (72.90 mg) at room temperature. The reaction mixture was stirred at 70° C. for 1 hour. The resulting reaction solution was diluted with 20 mL of water, and then extracted with ethyl acetate. The organic phase was dried over anhydrous sodium sulfate and filtered. The filtrate was concentrated under reduced pressure, and the residue was purified by preparative high performance liquid chromatography (separation column: Phenomenex Synergi C18, 150×30 mm×4 μm, mobile phase: [water (0.225% trifluoroacetic acid)-acetonitrile]; B %: 35%-65%, 10 min) to afford Example 23.

$^1$H NMR (400 MHz, CD$_3$OD) δ: 8.97 (d, J=5.0 Hz, 2H), 7.83 (dd, J=2.8, 5.6 Hz, 1H), 7.75-7.71 (m, 1H), 7.52 (t,

J=5.0 Hz, 1H), 7.30 (t, J=9.0 Hz, 1H), 5.42 (d, J=17.9 Hz, 1H), 5.01 (quin, J=6.4 Hz, 1H), 4.59 (d, J=17.7 Hz, 1H), 3.14 (dd, J=5.7, 16.4 Hz, 1H), 2.95 (dd, j=1.2, 16.4 Hz, 1H), 1.27 (d, J=6.8 Hz, 3H). MS(ESI) m/z: 379 [M+H$^+$].

Example 24

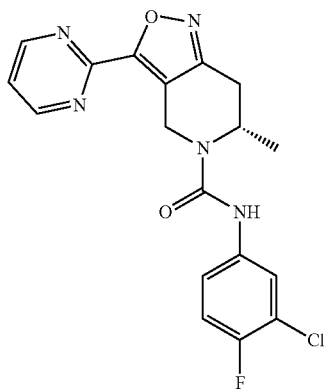 [SMILES: C[C@H]1Cc2noc(-c3ncccn3)c2CN1C(=O)Nc1ccc(F)c(Cl)c1]

The preparation of Example 24 can be carried out with reference to the preparation procedures A to H of Example 23, except that intermediate A-2 was replaced with intermediate A-3.

$^1$H NMR (400 MHz, DMSO-d$_6$) δ: 9.04 (d, J=4.9 Hz, 2H), 9.01 (s, 1H), 7.74 (dd, J=2.4, 6.8 Hz, 1H), 7.60 (t, J=4.9 Hz, 1H), 7.44-7.40 (m, 1H), 7.35-7.27 (m, 1H), 5.36 (d, J=18.0 Hz, 1H), 4.98-4.83 (m, 1H), 4.36 (d, J=18.0 Hz, 1H), 3.12-2.99 (m, 1H), 2.94-2.83 (m, 1H), 1.16 (d, J=6.8 Hz, 3H). MS(ESI) m/z: 388 [M+H$^+$].

Example 25

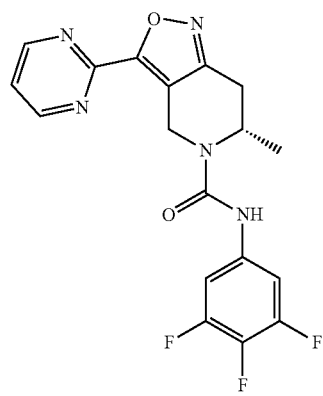 [SMILES: C[C@H]1Cc2noc(-c3ncccn3)c2CN1C(=O)Nc1cc(F)c(F)c(F)c1]

The preparation of Example 25 can be carried out with reference to the preparation procedures A to H of Example 23, except that intermediate A-2 was replaced with intermediate A-1.

$^1$H NMR (400 MHz, CDCl$_3$) δ: 8.86 (d, J=4.89 Hz, 2H), 7.29 (t, J=4.89 Hz, 1H), 7.08 (dd, J=6.05, 9.48 Hz, 2H), 6.45 (s, 1H), 5.07 (d, J=16.75 Hz, 1H), 5.05-4.94 (m, 1H), 4.55 (d, J=16.87 Hz, 1H), 3.10-3.00 (m, 1H), 2.94-2.85 (m, 1H), 1.17 (d, J=6.97 Hz, 3H). MS(ESI) m/z: 390 [M+H$^+$].

Example 26

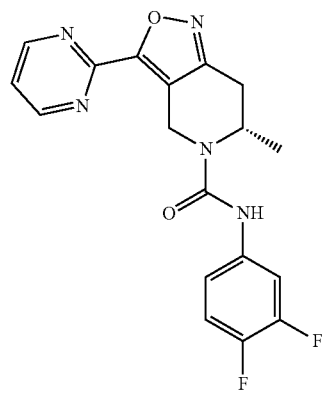 [SMILES: C[C@H]1Cc2noc(-c3ncccn3)c2CN1C(=O)Nc1ccc(F)c(F)c1]

The preparation of Example 26 can be carried out with reference to the preparation procedures A to H of Example 23, except that intermediate A-2 was replaced with intermediate A-6.

$^1$H NMR (400 MHz, DMSO-d$_6$) δ: 9.03 (s, 3H), 7.60 (s, 2H), 7.43-7.09 (m, 2H), 5.36 (d, J=17.9 Hz, 1H), 4.90 (s, 1H), 4.36 (d, J=18.1 Hz, 1H), 3.06 (d, J=12.1 Hz, 1H), 2.89 (d, J=16.4 Hz, 1H), 1.15 (d, J=5.4 Hz, 3H). MS(ESI) m/z: 372 [M+H$^+$].

Activity Assay

1. In Vitro Anti-HBV Activity Assay 1) 100 μL of HepG2.2.15 cells were seeded at a number of 1.2×10$^5$ cells per well into a 96-well cell culture plate, and then the cells were cultured in a 37° C. incubator with 5% carbon dioxide (CO$_2$) overnight. On day 2, the compounds to be tested were diluted with DMSO in 3-fold gradient to eight concentrations in total. Then the compounds were diluted 100-fold with culture medium, and 100 μL of the diluted compounds were taken and added to the cell-containing plate in a final volume of 200 μL, and the final concentration of DMSO was 0.5%, and two duplicate wells were used. The cells were cultured in a 37° C. incubator with 5% CO$_2$ for 3 days. On day 5, the solutions in the cell culture plate were replaced with fresh culture medium containing the same concentrations of compounds. When culture was performed for 8 days, cell culture plate supernatant was collected for the extraction of HBV DNA.

2) Detection of HBV DNA by real-time quantitative PCR: the total DNA in the supernatant was extracted with QIAamp 96 DNA Blood Kit, and the content of HBV DNA was detected by quantitative PCR using HBV specific primers and probes. 20 μL PCR pre-mixed solution and 5 μL HBV DNA sample or HBV plasmid standard sample were added to a quantitative PCR plate for reaction. The HBV plasmid standard sample was diluted in 10-fold gradient to seven concentrations from 10$^7$ to 10 copies/μL. The quantitative PCR reaction procedure was as follows: pre-denaturation at 95° C. for 10 minutes; denaturation at 95° C. for 15 seconds, reaction at 60° C. for 1 minute, and this cycle was repeated 40 times. The inhibition rate of each well against HBV DNA was calculated according to the following equation, and the inhibition rate data of the compounds were subjected to a non-linear fitting analysis using GraphPad Prism software to obtain EC$_{50}$ values of the compounds.

HBV DNA inhibition rate %=(1−copy number of HBV DNA of the sample/copy number of HBV DNA of DMSO control)*100%

The assay results are shown in Table 1 below.

TABLE 1

| Example | HepG2.2.15 EC$_{50}$ (nM) | Examples | HepG2.2.15 EC$_{50}$ (nM) | Examples | HepG2.2.15 EC$_{50}$ (nM) |
|---|---|---|---|---|---|
| 1 | 5.3 | 12 | 68.8 | 21 | 5.58 |
| 2 | 29.3 | 13 | 58.9 | 22 | 35.18 |
| 3 | 9.0 | 15 | 6.7 | 23 | 25.35 |
| 5 | 24.7 | 16 | 24.57 | 24 | 15.57 |
| 6 | 4.9 | 18 | 12.15 | 25 | 14.92 |
| 8 | 37.3 | 19 | 10.37 | 26 | 19.08 |
| 9 | 10.5 | 20 | 8.66 | | |

2. Pharmacokinetic Study for Mouse

This experiment aims to evaluate the pharmacokinetic behavior of the compounds after a single intravenous or gavage administration in mice. As for the intravenous administration, the compounds were formulated into 0.5 mg/mL clear solutions, vehicle: 5% DMSO/5% 12-hydroxy stearate (solutol)/90% water; as for the gavage administration, the compounds were formulated into 2 mg/mL suspensions, vehicle: 0.5% sodium carboxymethylcellulose/0.2% Tween 80/99.3% water.

The concentrations of the compounds in plasma were determined by high-performance liquid chromatography-tandem mass spectrometry (LC-MS/MS). The retention time, chromatogram acquisition and integration of the chromatograms of the compounds and the internal standard (diclofenac) were processed using the software Analyst (Applied Biosystems), and data statistics were processed using the software Watson LIMS (Thermo Fisher Scientific) or Analyst (Applied Biosystems). The concentration unit of the analyte in the sample is ng/mL, 3 significant digits were retained, and all the values represented by percentages (e.g., % deviation and % coefficient of variation, etc.) have one decimal place. Each calibration curve contains at least 6 concentration levels. The calibration standard samples were formulated using stock solutions from different sources from the quality control samples. If the deviation between the calculated concentration of a calibration standard sample and the indicated value exceeds ±15.0% (the lower limit of quantitation exceeds ±20.0%), such standard sample should be excluded in regression analysis. The excluded calibration standard samples should be less than 25%, and each calibration curve contains at least 6 calibration standard samples that meet the acceptable standard. If the calibration standard samples at the lower and upper limits of quantification need to be excluded, the upper and lower limits of quantification of this batch of analytes will be increased and decreased accordingly.

Plasma concentrations were processed using a non-compartmental model of the WinNonlin™ Version 6.3 (Pharsight, Mountain View, Calif.) pharmacokinetic software, and pharmacokinetic parameters were calculated using the linear logarithmic trapezoidal method. The pharmacokinetic parameters to be calculated include, but are not limited to (if the data is not allowed), $T_{1/2}$, Vdss, CL, AUC$_{0-24h}$ of the intravenous group; $C_{max}$, $T_{max}$, AUC$_{0-24h}$ and bioavailability (F %) of the oral gavage group.

The relevant pharmacokinetic parameters of the examples of the present invention in mice are shown in Table 2 below.

TABLE 2

| | Intravenous injection | | | | | Oral gavage | | | | |
|---|---|---|---|---|---|---|---|---|---|---|
| Example | dose (mg/Kg) | $T_{1/2}$ (h) | Vd$_{ss}$ (L/Kg) | CL (mL/mm/Kg) | AUC$_{0-24h}$ (nM·h) | dose (mg/Kg) | $C_{max}$ (nM) | $T_{max}$ (h) | AUC$_{0-24h}$ (nM·h) | F (%) |
| 1 | 1 | 5.62 | 2.77 | 5.80 | 6709 | 10 | 4260 | 1.00 | 47167 | 76.1 |
| 6 | 1 | 9.31 | 2.33 | 2.84 | 11421 | 10 | 4935 | 0.50 | 66683 | 58.4 |
| 23 | 1 | 3.03 | 1.09 | 4.36 | 10047 | 3 | 3395 | 0.50 | 16737 | 55.3 |

3. In Vivo Activity Assay of HBV DNA in Mouse Plasmid Model of Tail Vein High-Pressure Injection with Water The purpose of this study was to test the inhibitory effect of the compound (Example 6) against HBV in mice through a mouse model of high-pressure tail vein injection. In this experiment, female BABL/c mice were used, and the mice were 6-7 weeks old. The HBV plasmid DNA was extracted by using pAAV2-HBV 1.3 mer with Qiagen EndoFree Plasmid Giga kit at a concentration of 1000 ng/μL. The resulting solution was diluted with normal saline before use and stored at 4° C. until use.

3.1 Grouping of Animals

The grouping of experimental animals is shown in Table 3 below:

TABLE 3

| | | Time to start grouping |
|---|---|---|
| Group | Number of animals per group | Time to start dosing is defined as day 0 of the experiment Dosing and handling of each group |
| 1 | 5 | Solvent 0.5% sodium carboxymethylcellulose/0.2% Tween 80/99.3% water, gavage, twice a day (8 hr/16 hr), from day 1 to day 7 * |
| 2 | 5 | Example 6, 30 mg/Kg, gavage, twice a day (8 hr/16 hr), from day 1 to day 7 * |

*: dosing only once on day 7.

3.2 Pharmaceutical Formulation

The Pharmaceutical Formulation is shown in Table 4 below:

TABLE 4

| Test compound | Pharmaceutical formulation and vehicle used (administration volume is 10 mL/Kg) |
|---|---|
| Control: solvent (0.5% sodium carboxymethylcellulose/ 0.2% Tween 80/ 99.3% water) | An appropriate amount of sodium carboxymethylcellulose powder was weighed, and dissolved in pure water to formulate a solution at a concentration of 0.5%, and then thereto was added Tween 80 in a ratio of v:v = 99.8:0.2, and mixed uniformly; it was formulated before the first administration and then stored at 4° C. until use. |
| Example 6 | An appropriate amount of Example 6 powder was weighed and dissolved in the administration vehicle to formulate a solution at a concentration of 3 mg/mL. The solution was sonicated and stirred uniformly. It is formulated every afternoon for the second administration of the same day and the first administration of the next day. After formulation, it should be stored in the dark at 4° C., and vortex-agitated before administration to make it as dispersed as possible. |

3.3 Administration Schedule

TABLE 5

| Group | Test compound | Dosing regimen (dose/administration mode/ frequency/total duration) |
|---|---|---|
| 1 | Solvent control group | 10 mL/Kg, gavage, twice a day (8 hr/16 hr), from day 1 to day 7 * |
| 2 | Example 6 | 30 mg/Kg, gavage, twice a day (8 hr/16 hr), from day 1 to day 7 * |

*: dosing only once on day 7.

3.4 Non-Endpoint Blood Collection and Transport

100 μL of whole blood was taken from each mouse approximately 4 hours after the first administration On days 1, 3, and 5, and the whole blood was collected into a tube containing sodium heparin, centrifuged at 4° C. at 7000 rpm for 10 minutes, and the supernatant was taken to obtain plasma. The plasma was stored in a refrigerator at −80° C. and transported to an analytical laboratory for testing under dry ice freezing condition.

3.5 Quantitative PCR Detection of HBV DNA Content in Mouse Plasma

1) DNA in plasma was extracted, and the experimental procedure was carried out with reference to the instruction for QIAamp 96 DNA Blood Kit.

2) Quantitative PCR detection of HBV DNA content in mouse plasma

A qPCR reaction mixture was formulated (see Table 6). The qPCR reaction mixture, sample and standard sample were added to a 96-well reaction plate. The standard sample was plasmid DNA containing the full-length sequence of type D HBV. The standard sample was diluted from $10^7$ copies/μL in 10-fold gradient to successively obtain $10^6$~$10^1$ copies/μL of DNA standard samples. PCR reaction: 95° C., 10 min; 95° C., 15 seconds; 60° C., 1 minute; 40 cycles.

TABLE 6

| qPCR Reaction composition table | |
|---|---|
| components of PCR reaction solution | volume required for one reaction system |
| FastStart Universal Probe Master | 12.5 μL |
| Forward primer (10 μM) | 1 μL |
| Reverse primer (10 μM) | 1 μL |
| Probe (10 μM) | 0.5 μL |
| Water | 5 μL |

HBV DNA content = DNA content detected by HBV primer − DNA content detected by pAAV2 primer.

3.6 Quantitative PCR Detection of HBV DNA in Mouse Liver

1) Extraction of Total Liver DNA

Liver tissue was taken and homogenized with a tissue grinder. After centrifugation, the supernatant was transferred to a new centrifuge tube and digested with proteinase K digestion solution for 3 hours. The resulting mixture was cooled, and then RNAse A was added thereto to incubate for 30 minutes. The RNase A-treated mixture was extracted twice with an equal volume of phenol chloroform isoamyl alcohol to remove residual protein. The supernatant was transferred to a new centrifuge tube, and isopropanol was added thereto to precipitate the DNA. The DNA precipitation was washed twice with 70% ethanol. The precipitation was then air-dried and TE (10 mM Tris-HCl, pH 8.0, 1 mM EDTA) was added thereto to dissolve the DNA.

2) Quantitative PCR Detection of HBV DNA in Mouse Liver

The DNA concentrations were measured with Nanodrop and adjusted to 10 ng/μL for all the samples. 5 μL samples were added to the quantitative PCR reaction system for quantitative PCR.

HBV DNA content=DNA content detected by HBV primer-DNA content detected by pAAV2 primer.

3.7 Assay Results

1) Blood samples were taken from mice of each test group on days 1, 3, 5, and 7 after administration, and the measured values of HBV DNA concentration (Log HBV DNA) are shown in Table 7 below:

TABLE 7

| Blood sampling time | Log HBV DNA mean value (copy number/μL) | |
|---|---|---|
| | Solvent control group | Example 6 |
| Day 1 | 2.22 | 2.23 |
| Day 3 | 4.51 | 1.74 |
| Day 5 | 5.01 | 2.02 |
| Day 7 | 3.30 | 1.85 |

LLOQ = 40 copies/μL, Log(LLOQ) = 1.60 (LLOQ denotes the lowest detection limit)

This result is shown in FIG. 1.

2) After 7 days of administration, the measured values of HBV DNA concentration (Log HBV DNA) in the liver tissues of the animals in each test group are shown in Table 8 below:

TABLE 8

| Log HBV DNA mean value (copy number/μL) | |
| --- | --- |
| Solvent control group | Example 6 |
| 5.67 | 3.09 |

Figure 2:
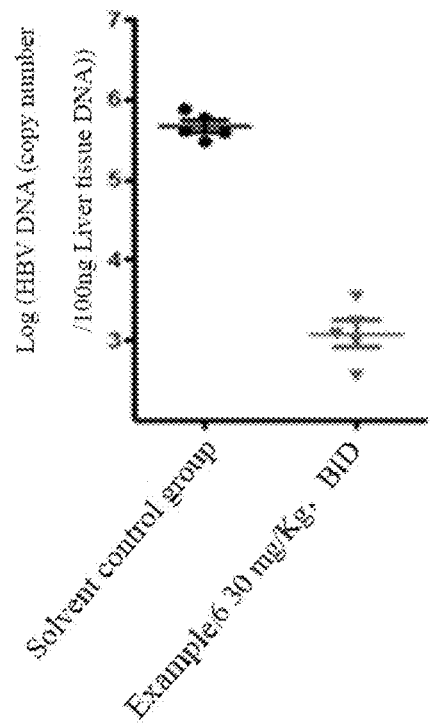
FIG. 2 shows the level of Log (HBV DNA copy number) per unit weight of liver tissue from mice in each test group on day 7 after administration with the compound of Example 6.

This result is shown in FIG. 2.

4. In Vivo Activity Assay of HBV DNA in Mouse Plasmid Model of Tail Vein High-Pressure Injection with Water The purpose of this study was to test the inhibitory effect of the compound (Example 23) against HBV in mice through a mouse model of high-pressure tail vein injection. In this experiment, female BABL/c mice were used, and the mice were 6-7 weeks old. The HBV plasmid DNA was extracted by using pAAV2-HBV 1.3 mer with Qiagen EndoFree Plasmid Giga kit at a concentration of 1000 ng/μL. The resulting solution was diluted with normal saline before use and stored at 4° C. until use.

4.1 Grouping of Animals

The grouping of experimental animals is shown in Table 9 below:

TABLE 9

| | | Time to start grouping |
| --- | --- | --- |
| Group | Number of animals per group | Time to start dosing is defined as day 0 of the experiment Dosing and handling of each group |
| 1 | 5 | Solvent 0.5% sodium carboxymethylcellulose/0.2% Tween 80/99.3% water, gavage, once a day, from day 1 to day 7 * |
| 2 | 5 | Example 23, 60 mg/Kg, gavage, once a day, from day 1 to day 7 * |
| 3 | 5 | Example 23, 60 mg/Kg, gavage, twice a day (8 hr/16 hr), from day 1 to day 7 * |

*: dosing only once on day 7.

4.2 Pharmaceutical Formulation

The Pharmaceutical Formulation is shown in Table 10 below:

TABLE 10

| Test compound | Pharmaceutical formulation and vehicle used |
| --- | --- |
| Solvent control: 10% solutol HS 15 | Solutol HS 15 and deionized water were mixed at a volume ratio of 1:9 and stored at 4° C. until use. It was formulated before the first administration and used for 7 days of administration. |
| Example 23 | An appropriate amount of Example 23 was weighed, dissolved in 10% solutol HS 15, and sonicated to a uniform suspension. The formulations were respectively prepared into 6 mg/mL, and stored at 4° C. until use. They were formulated before the first administration and used for 7 days of administration, and sonicated again to a uniform suspension before each administration. |

4.3 Administration Schedule

TABLE 11

| Group | Test compound | Dosing regimen (dose/administration mode/ frequency/total duration) |
| --- | --- | --- |
| 1 | Solvent control group | 10 mL/Kg, gavage, once a day, from day 1 to day 7 * |
| 2 | Example 23 | 60 mg/Kg, gavage, once a day, from day 1 to day 7 * |
| 3 | Example 23 | 60 mg/Kg, gavage, twice a day (8 hr/16 hr), from day 1 to day 7 * |

*: dosing only once on day 7.

4.4 Assay Results

1) Blood samples were taken from mice of each test group on days 1, 3, 5, and 7 after administration, and the measured values of HBV DNA concentration (Log HBV DNA) are shown in Table 12 below:

TABLE 12

| Blood sampling time | Log HBV DNA mean value (copy number/μL) | | |
| --- | --- | --- | --- |
| | Solvent control group | Example 23 (60 mg/Kg, QD) | Example 23 (60 mg/Kg, BID) |
| Day 1 | 2.03 | 2.10 | 1.94 |
| Day 3 | 4.47 | 3.15 | 3.02 |
| Day 5 | 4.76 | 3.92 | 2.94 |
| Day 7 | 3.53 | 3.19 | 2.14 |

Figure 3:
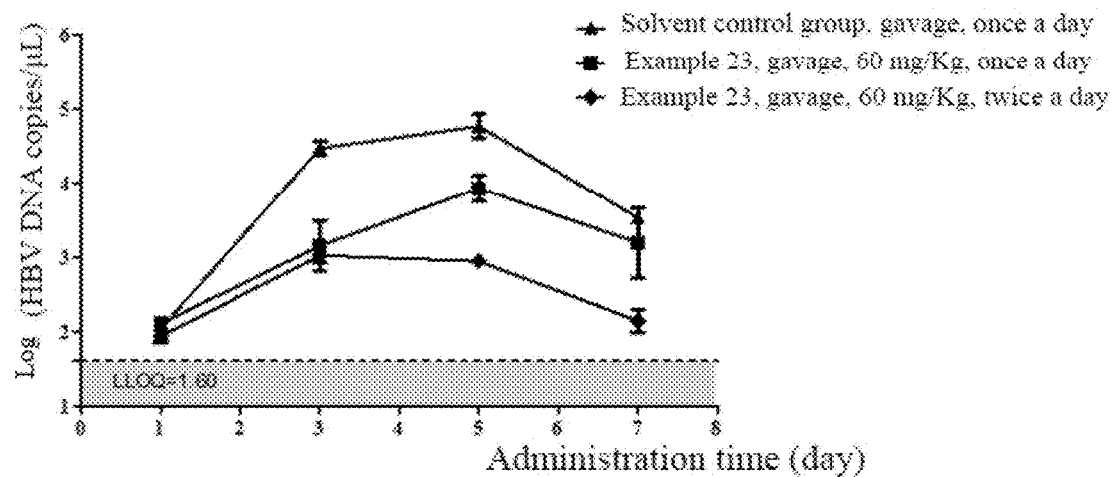
FIG. 3 is a graph showing changes in Log (HBV DNA copy number) per unit volume of plasma from mice in each test group after administration with the compound of Example 23 for 1 to 7 days.

This result is shown in FIG. 3.

2) After 7 days of administration, the measured values of HBV DNA concentration (Log HBV DNA) in the liver tissues of the animals in each test group are shown in Table 13 below:

TABLE 13

| Log HBV DNA mean value (copy number/μL) | | |
| --- | --- | --- |
| Solvent control group | Example 23 (60 mg/Kg, QD) | Example 23 (60 mg/Kg, BID) |
| 6.01 | 5.18 | 4.50 |

Figure 4:
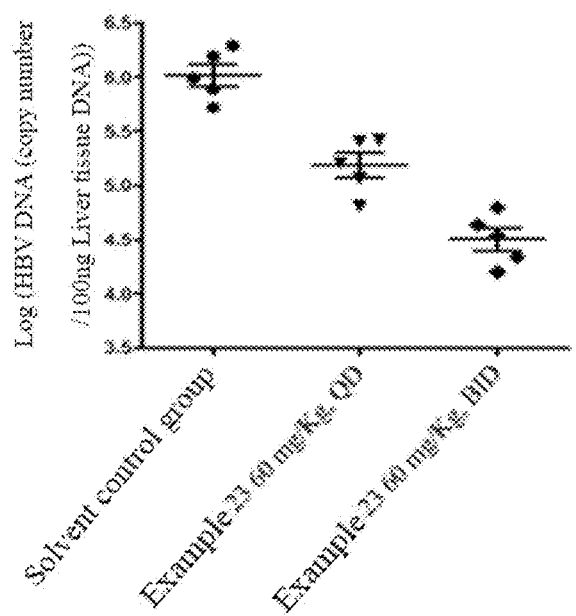
FIG. 4 shows the level of Log (HBV DNA copy number) per unit weight of liver tissue mice in each test group on day 7 after administration with the compound of Example 23.

This result is shown in FIG. 4.

What is claimed is:

1. A compound of Formula (I), a pharmaceutically acceptable salt or an isomer thereof,

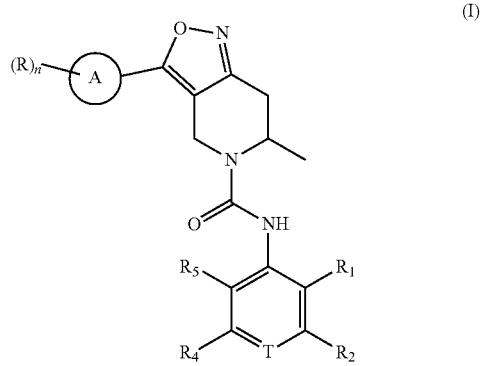

wherein ring A is 6- to 12-membered aryl or 5- to 6-membered heteroaryl;

each R is independently F; Cl; Br; I; —CN; —OH; —NR$^a$R$^b$; —S(=O)$_2$NR$^a$R$^b$; —S(=O)$_2$R$^c$; —C(=O)OR$^d$; C$_{1-6}$ alkoxy; or C$_{1-6}$ alkyl optionally substituted with 1, 2 or 3 substituents independently selected from the group consisting of F, Cl, Br, I, —OH, —NH$_2$ and —CN;

n is 0, 1, 2 or 3;

T is N or CR$_3$;

R$_1$ and R$_5$ are each independently H; F; Cl; Br; I; —CN; —OH; —NR$^a$R$^b$; C$_{1-3}$ alkoxy; or C$_{1-3}$ alkyl optionally substituted with 1, 2 or 3 substituents independently selected from the group consisting of F, Cl, Br, I, —OH, —NH$_2$, —CN and —NO$_2$;

R$_2$ and R$_4$ are each independently H; F; Cl; Br; I; —CN; —OH; —NR$^a$R$^b$; C$_{1-6}$ alkoxy; or C$_{1-6}$ alkyl optionally substituted with 1, 2 or 3 substituents independently selected from the group consisting of F, Cl, Br, I, —OH, —NH$_2$, —CN and —NO$_2$;

R$_3$ is F, Br or —CN;

R$^a$, R$^b$, R$^c$ and R$^d$ are each independently H or C$_{1-6}$ alkyl;

the 5- to 6-membered heteroaryl contains 1, 2 or 3 heteroatoms or heteroatom groups independently selected from the group consisting of —O—, —S—, N and —NH—.

2. The compound or a pharmaceutically acceptable salt or an isomer thereof according to claim 1, wherein, said ring A is phenyl or 5- to 6-membered heteroaryl; or said ring A is phenyl, thiazolyl, isothiazolyl, pyrazolyl, pyrrolyl, pyrazinyl, pyrimidinyl, or pyridyl.

3. The compound or a pharmaceutically acceptable salt or an isomer thereof according to claim 1, wherein, said R$^a$, R$^b$, R$^c$ and R$^d$ are each independently H, —CH$_3$, —CH$_2$CH$_3$, —CH$_2$CH$_2$CH$_3$ or —CH$_2$(CH$_3$)$_2$.

4. The compound or a pharmaceutically acceptable salt or an isomer thereof according to claim 1, wherein, said each R is independently F, Cl, Br, I, —CN, —OH, —OCH$_3$, —OCH$_2$CH$_3$, —NH$_2$, —N(CH$_3$)$_2$, —S(=O)$_2$NH$_2$, —S(=O)$_2$CH$_3$, —C(=O)OCH$_3$, —C(=O)OCH$_2$CH$_3$, —CH$_3$, —CH$_2$CH$_3$, CF$_3$ or —CH$_2$OH.

5. The compound or a pharmaceutically acceptable salt or an isomer thereof according to claim 1, wherein, said R$_1$ and R$_5$ are each independently H, F, Cl, Br, I, —CN, —OH, —OCH$_3$, —NH$_2$, —CH$_3$, —CH$_2$F, —CHF$_2$ or —CF$_3$.

6. The compound or a pharmaceutically acceptable salt or an isomer thereof according to claim 1, wherein, said R$_2$ and R$_4$ are each independently H, F, Cl, Br, I, —CN, —OH, —OCH$_3$, —OCH$_2$CH$_3$, —NH$_2$, —CH$_3$, —CH$_2$CH$_3$, —CH$_2$F, —CHF$_2$ or —CF$_3$.

7. The compound or a pharmaceutically acceptable salt or an isomer thereof according to claim 1, wherein, said structural unit

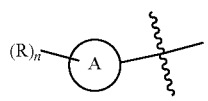

is

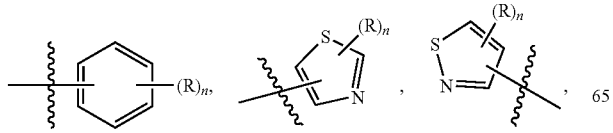

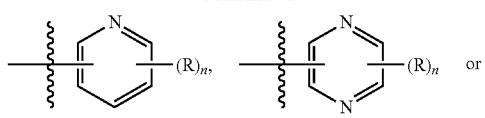

or said structural unit

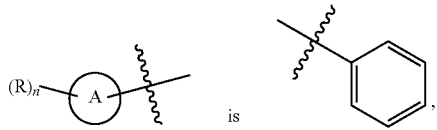

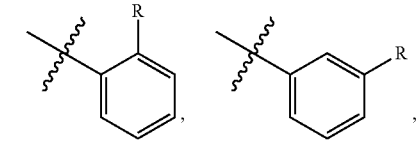

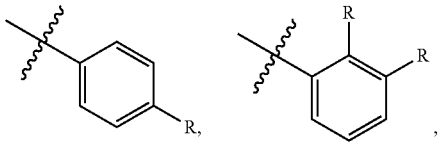

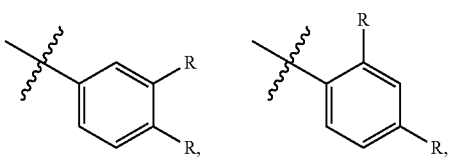

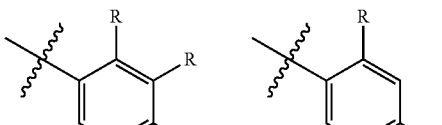

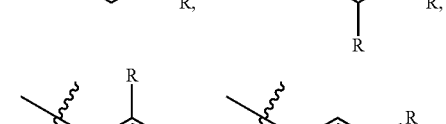

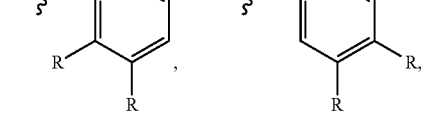

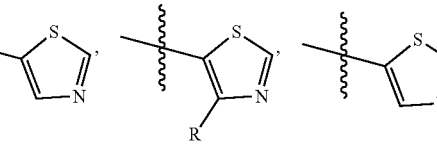

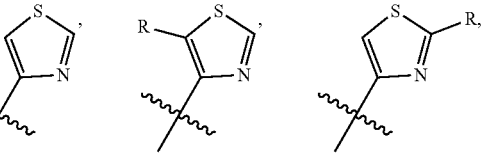

-continued
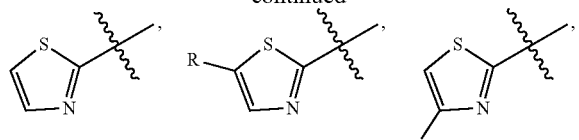
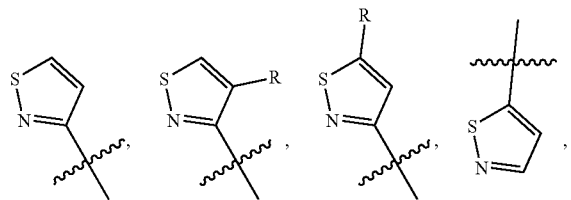
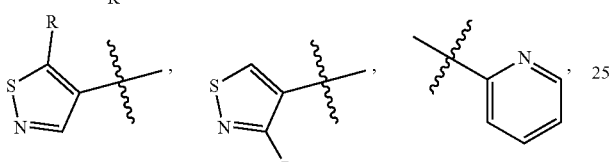
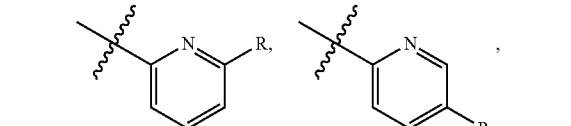
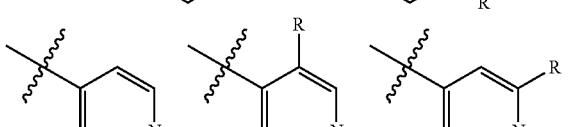
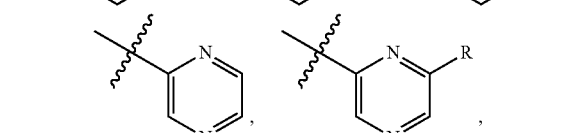
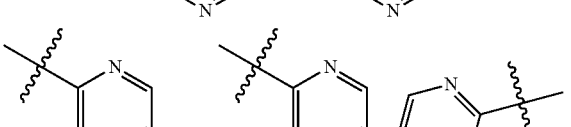
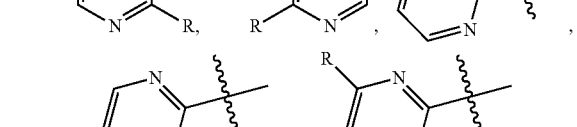
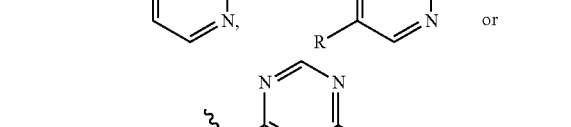
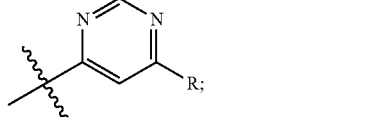
or
said structural unit is
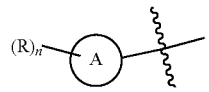
is
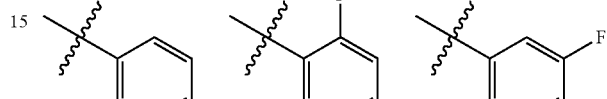
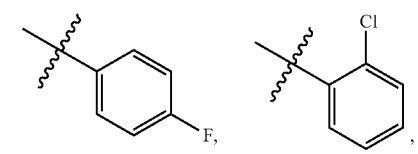
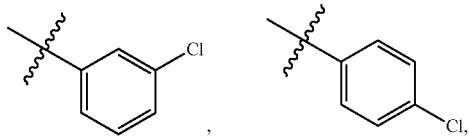
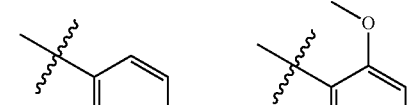
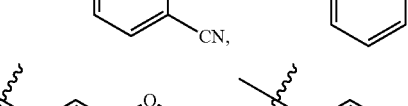
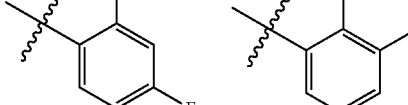
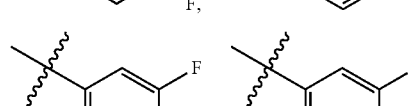
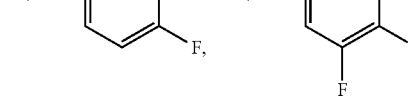
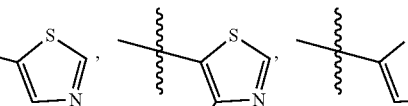
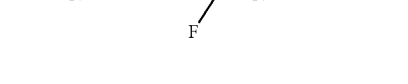

-continued
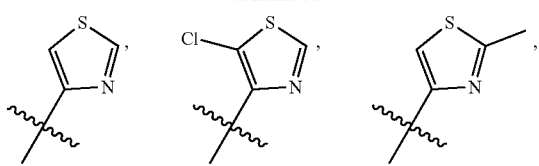
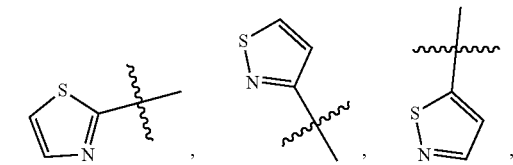
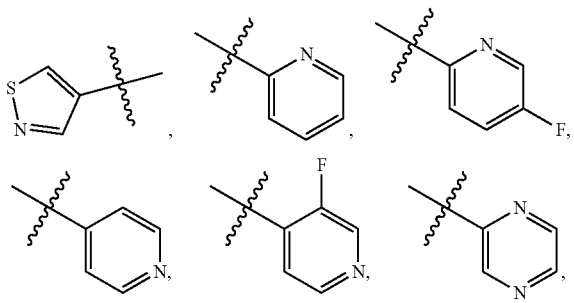
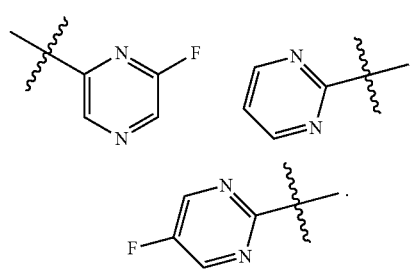
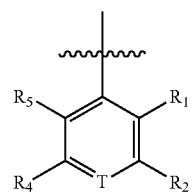
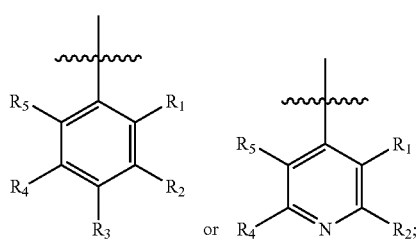
8. The compound or a pharmaceutically acceptable salt or an isomer thereof according to claim 1, wherein, said structural unit
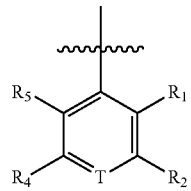
is
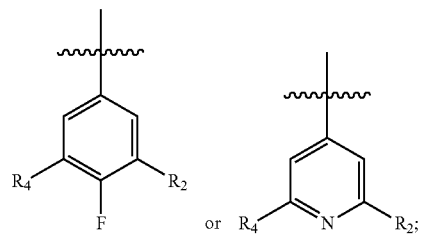
or said structural unit
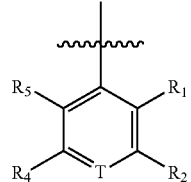
is
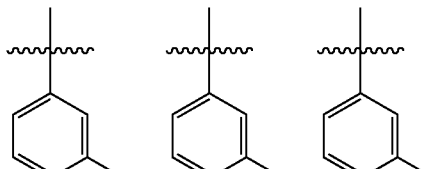
or said structural unit is
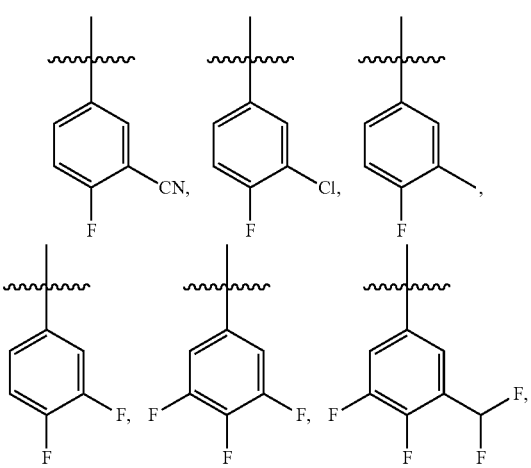
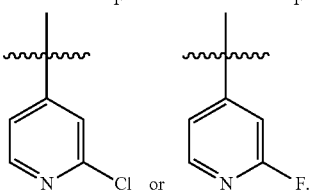

9. The compound or a pharmaceutically acceptable salt or an isomer thereof according to claim 1, having a structure represented by Formula (II-a) or (III-a):

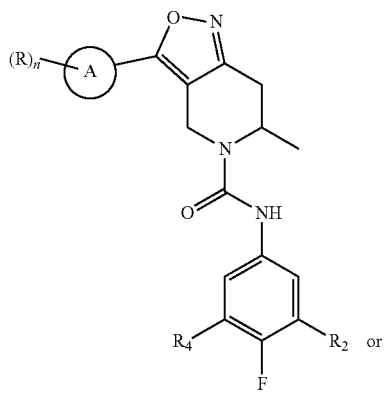
(II-a)

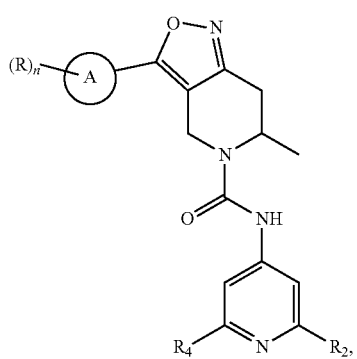
(III-a)

wherein, ring A, $R_2$, $R_4$, R and n are as defined in claim 1.

10. The compound or a pharmaceutically acceptable salt or an isomer thereof according to claim 7, having a structure represented by Formula (II-a-1) or (III-a-1):

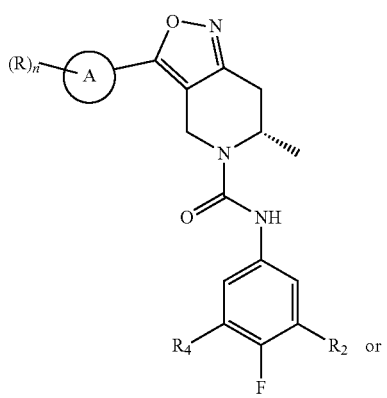
(II-a-1)

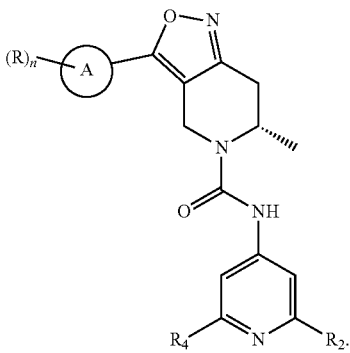
(III-a-1)

11. The compound or a pharmaceutically acceptable salt or an isomer thereof according to claim 1, having a structure represented by Formula (II-b), (II-c), (III-b) or (III-c):

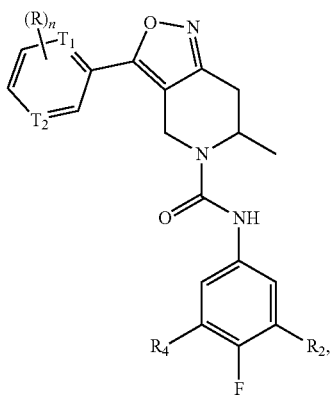
(II-b)

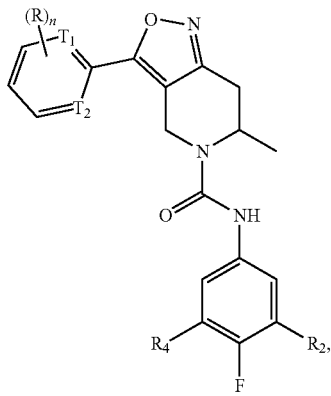
(II-c)

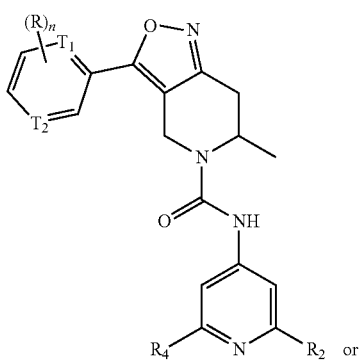
(III-b)

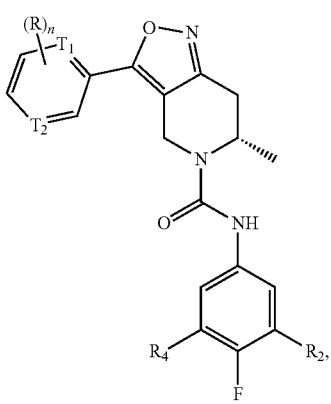
(II-b-1)

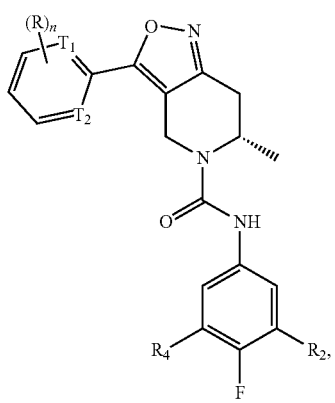
(III-c)

wherein, T$_1$ and T$_2$ are each independently N or CH;

R$_2$, R$_4$, R and n are as defined in claim 1.

12. The compound or a pharmaceutically acceptable salt or an isomer thereof according to claim 8, having a structure represented by Formula (II-b-1), (II-c-1), (III-b-1) or (III-c-1):

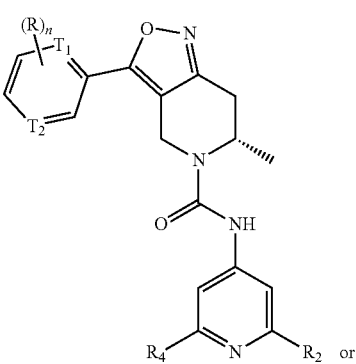
(II-c-1)

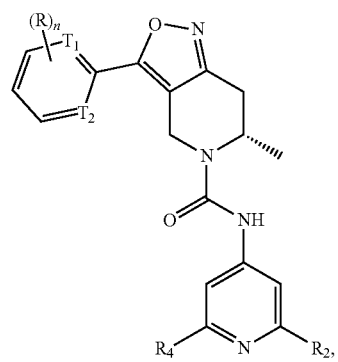
(III-b-1)

(III-c-1)

wherein, T$_1$ and T$_2$ are each independently N or CH.

13. The compound or a pharmaceutically acceptable salt or an isomer thereof according to claim 1, wherein the compound has a structure represented by Formula (II-d), (II-e), (II-f), (II-k), (III-d), (III-e), (III-f) or (III-k):

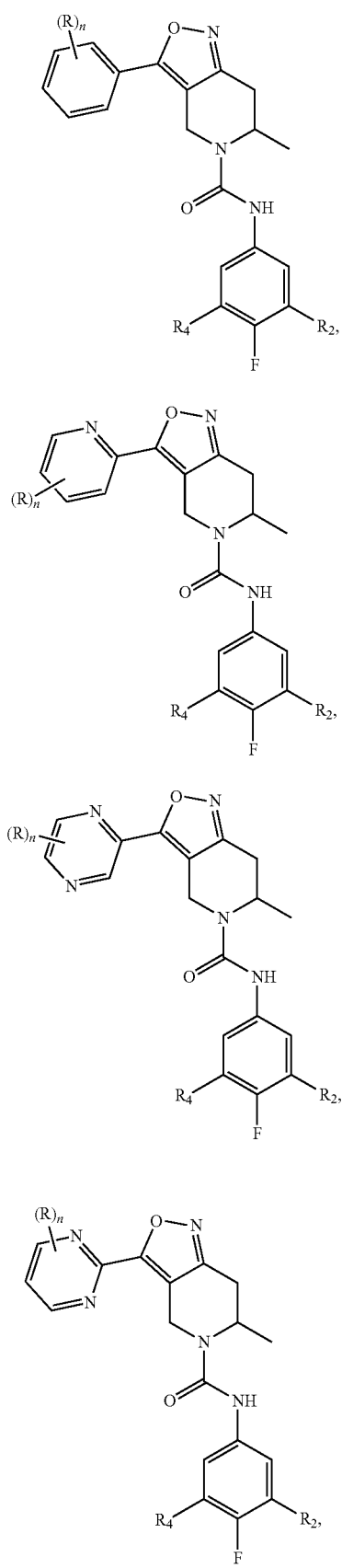
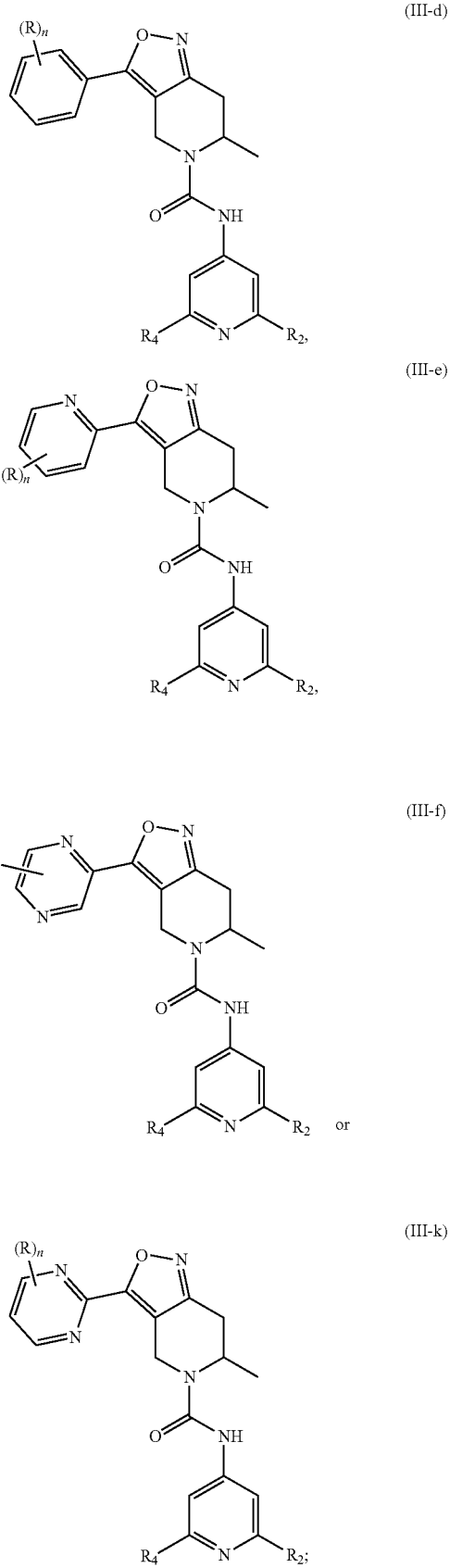

or the compound has a structure represented by Formulae (II-g) to (II-i) or Formulae (III-g) to (III-i):
(II-g)
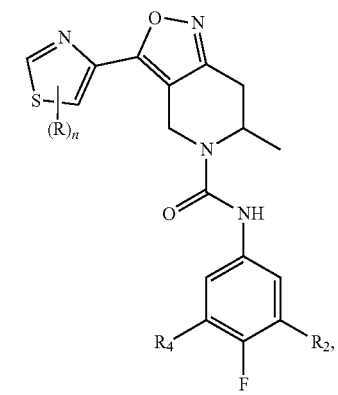
(II-h)
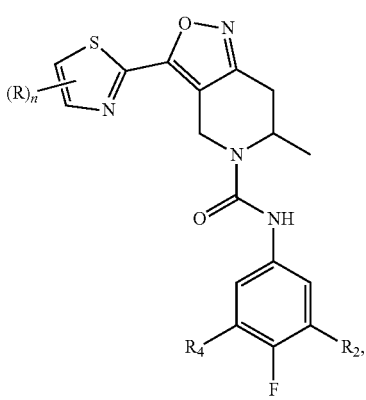
(II-i)
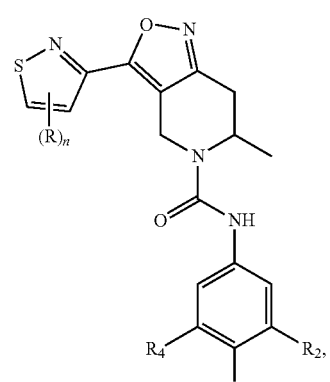
(III-g)
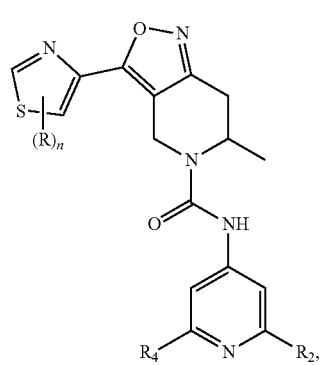
(III-h)
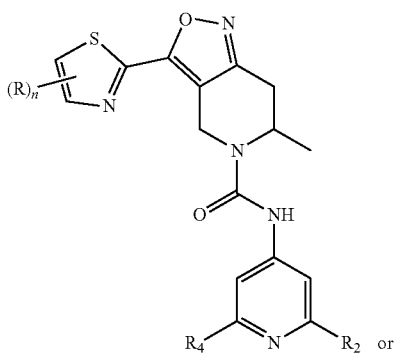
(III-i)
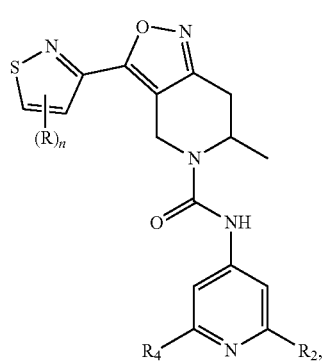
wherein, $R_2$ and $R_4$, R and n are as defined in claim 1.
14. The compound or a pharmaceutically acceptable salt or an isomer thereof according to claim 13, wherein the compound has a structure represented by Formula (II-d-1), (II-e-1), (II-f-1), (II-k-1), (III-d-1), (III-e-1), (III-f-1) or (III-k-1):
(II-d-1)
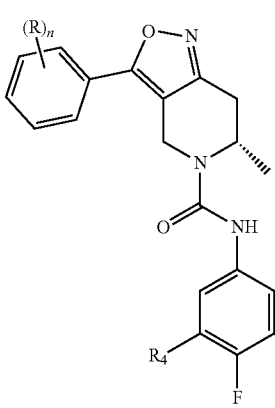

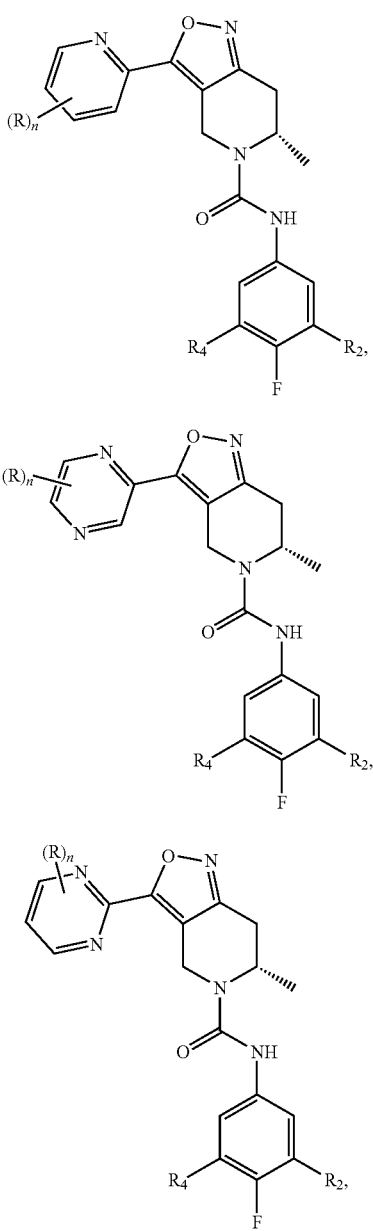
(II-e-1)
(II-f-1)
(II-k-1)
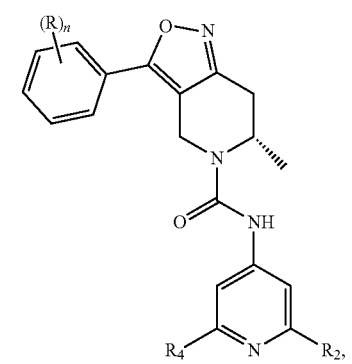
(III-d-1)
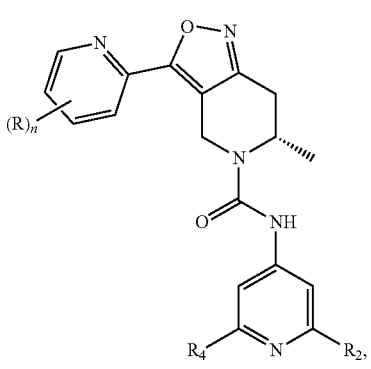
(III-e-1)
(III-f-1)
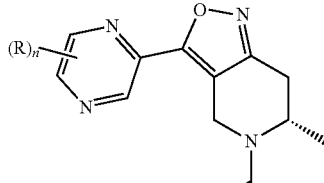
or
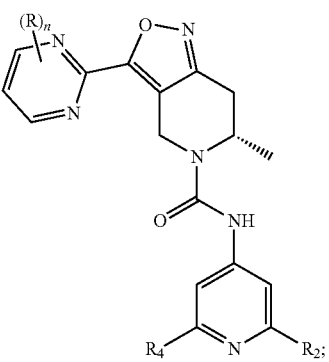
(III-k-1)
or the compound has a structure represented by Formulae (II-g-1) to (II-i-1) or Formulae (III-g-1) to (III-i-1):
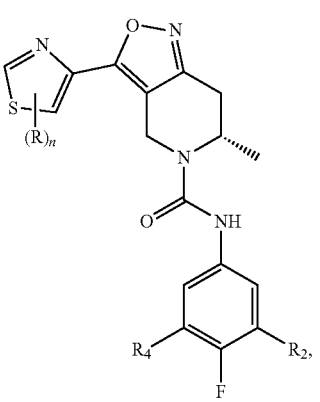
(II-g-1)

15. The compound or a pharmaceutically acceptable salt or an isomer thereof according to claim 13, having a structure represented by Formula (II-m) or (III-m):

16. The compound or a pharmaceutically acceptable salt or an isomer thereof according to claim 15, having a structure represented by Formula (II-m-1) or (III-m-1):

(II-m-1)
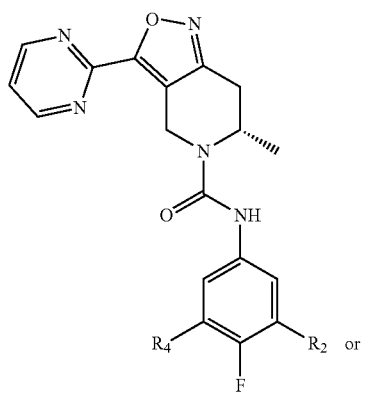
or
(III-m-1)
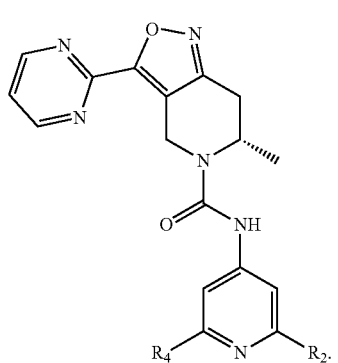
17. A compound or a pharmaceutically acceptable salt or an isomer thereof as follows:
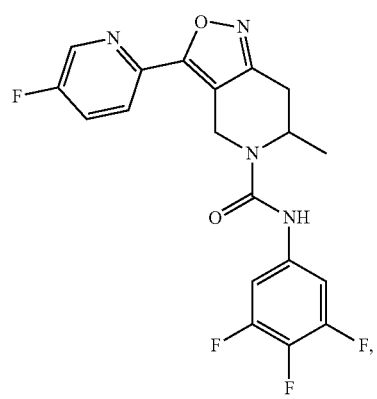
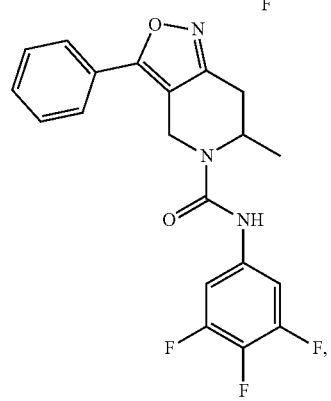
-continued
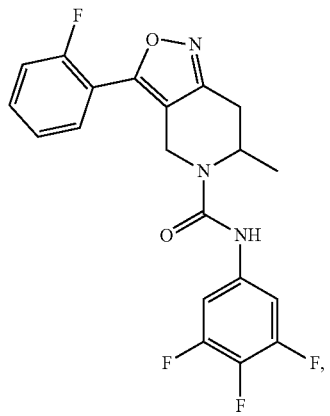
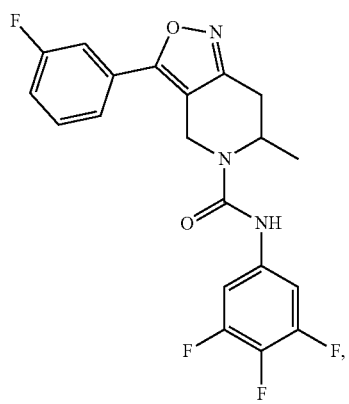
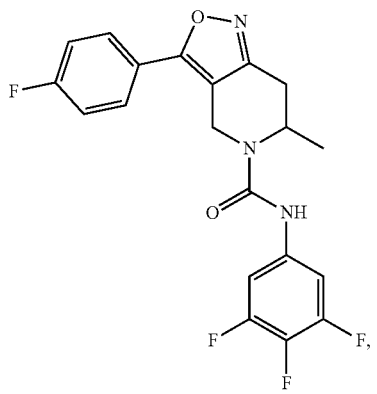
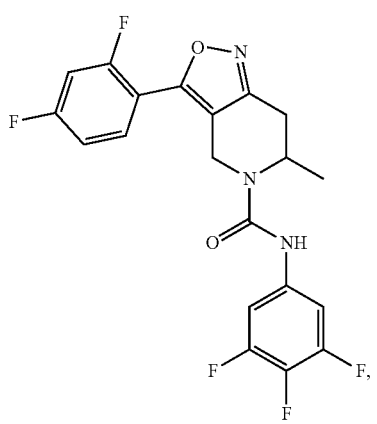

95
-continued
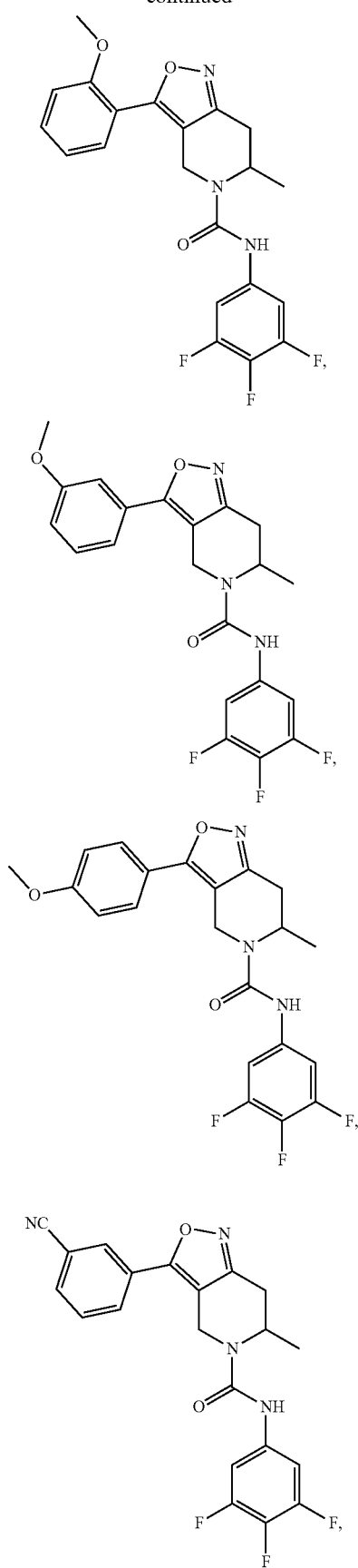
96
-continued
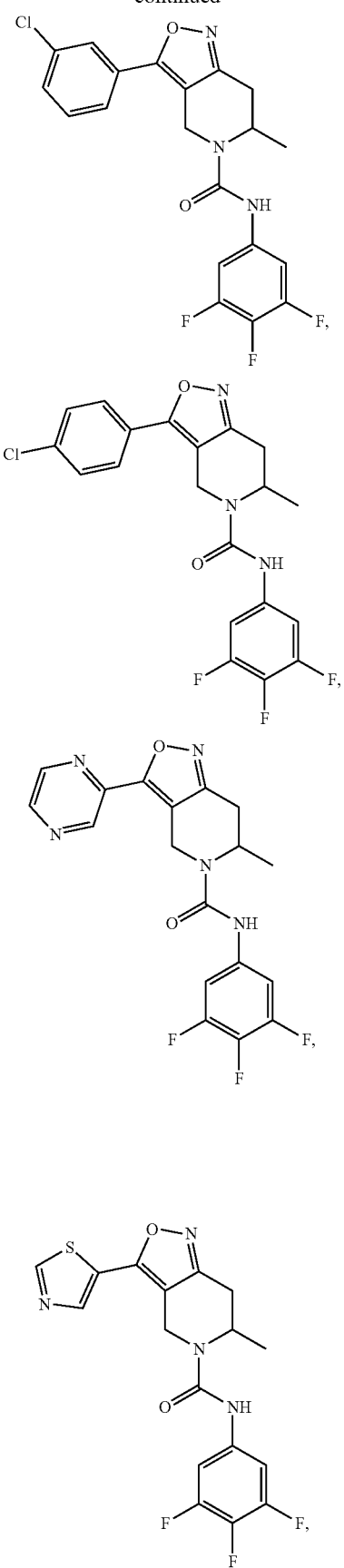

97
-continued
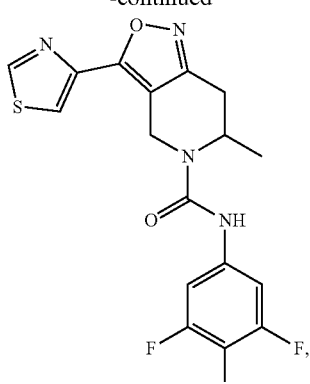
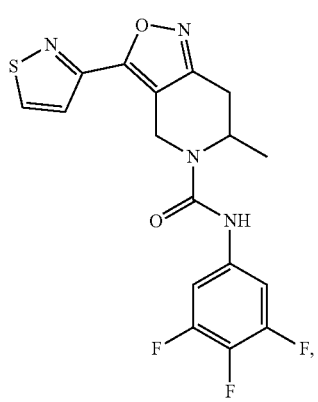
98
-continued
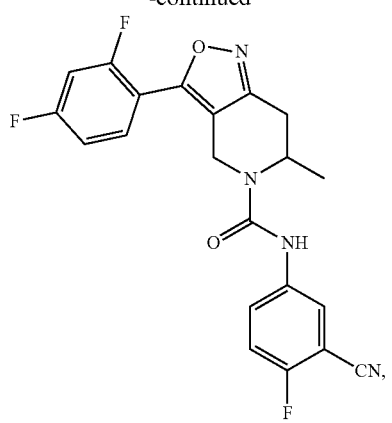
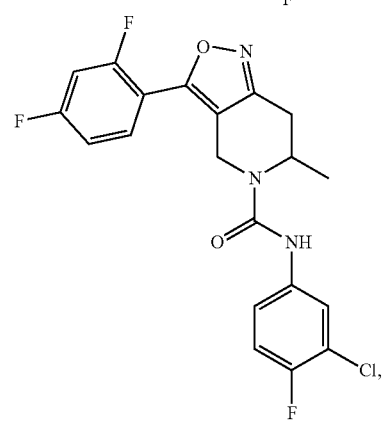
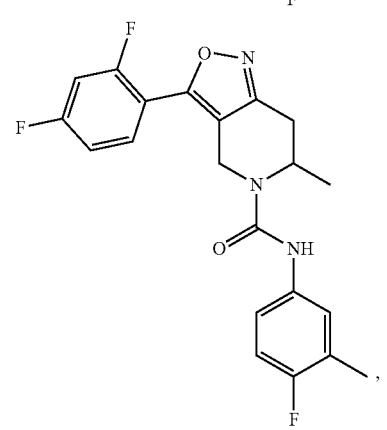
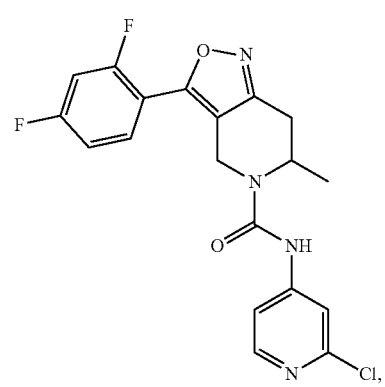

99
-continued
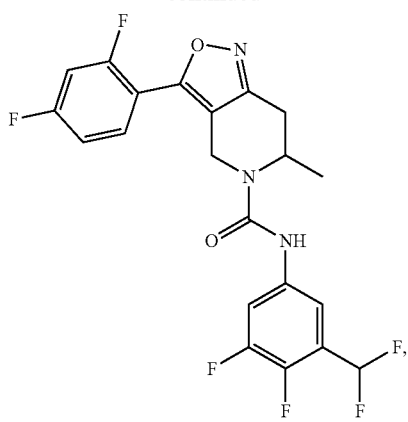
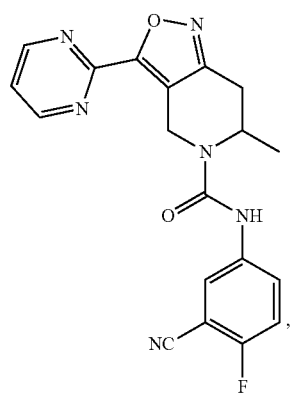
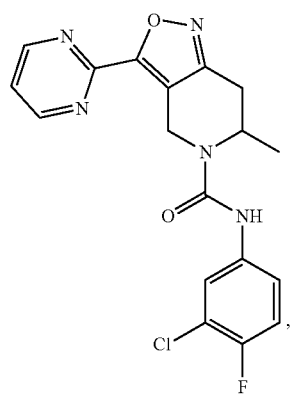
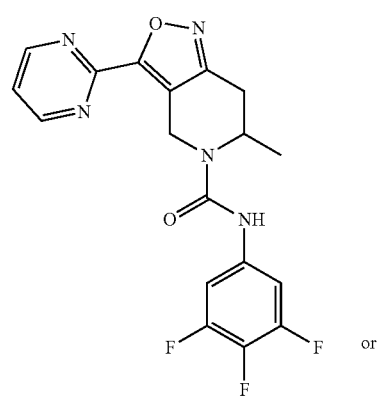
or
100
-continued
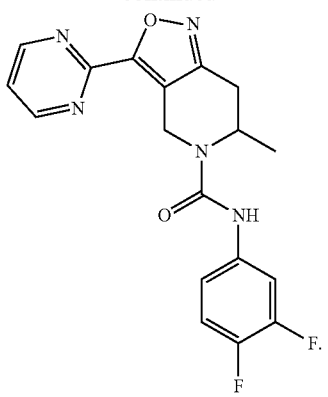
18. A compound or a pharmaceutically acceptable salt or an isomer thereof as follows:
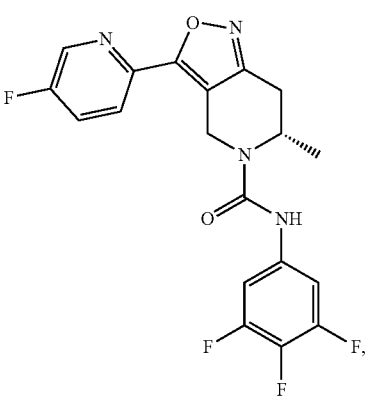
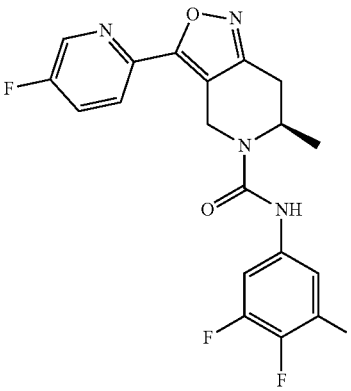
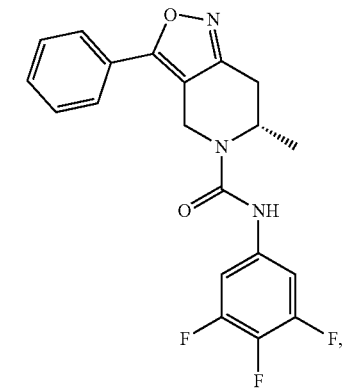

101
-continued
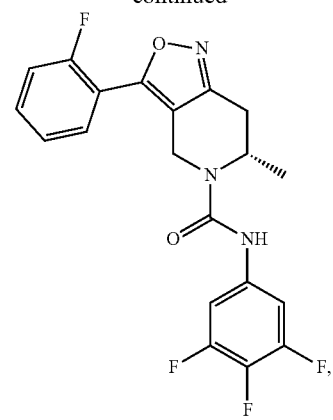
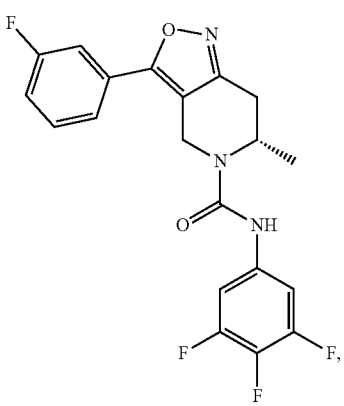
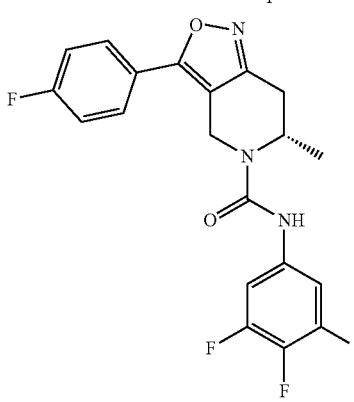
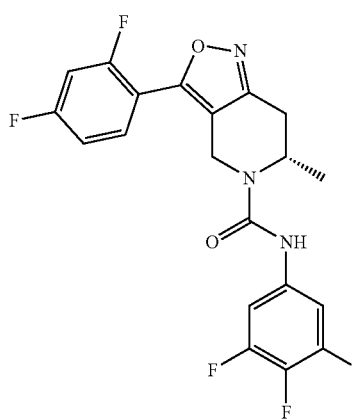
102
-continued
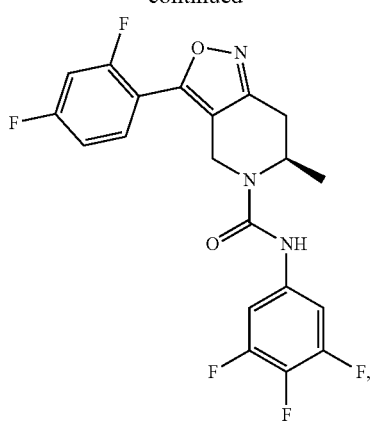
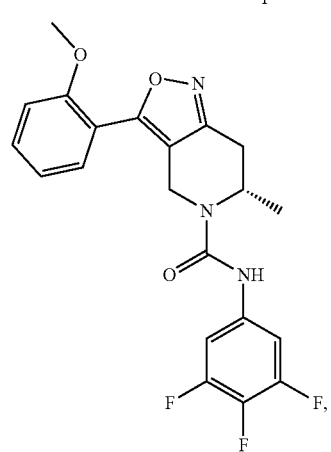
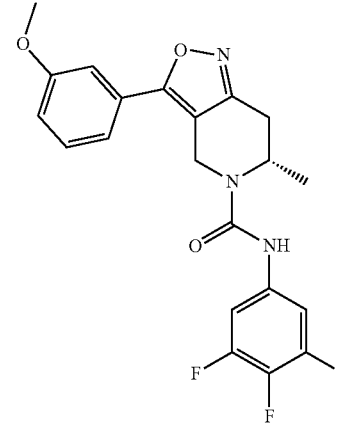
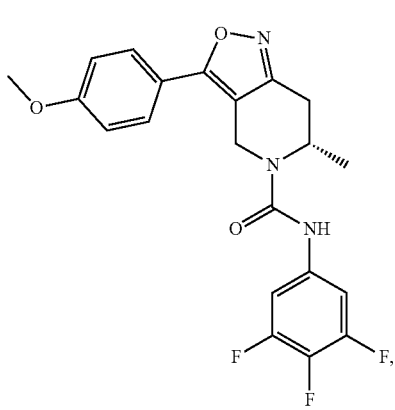

103
-continued
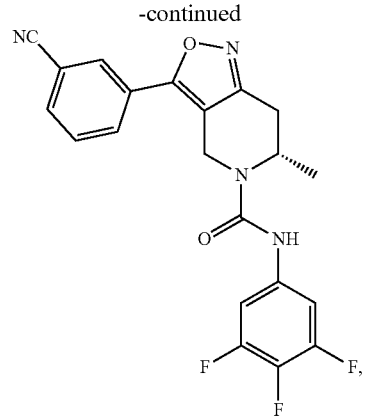
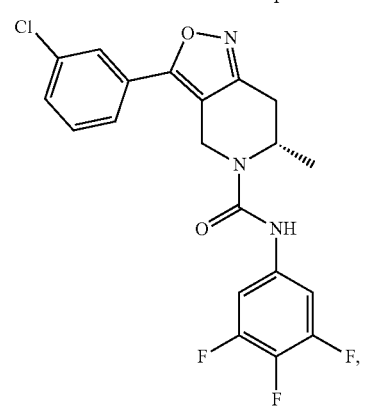
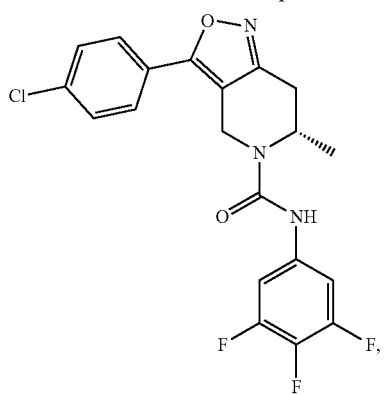
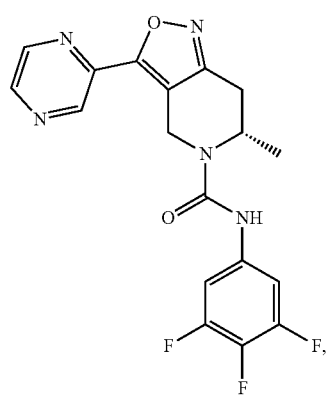
104
-continued
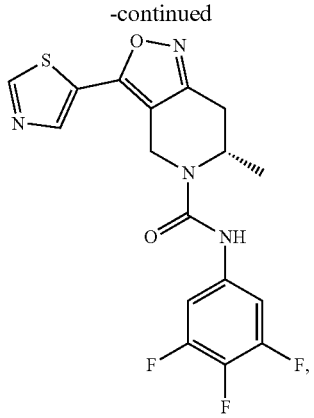
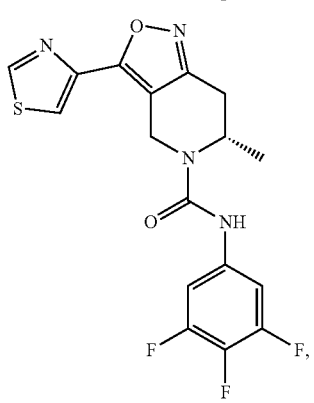
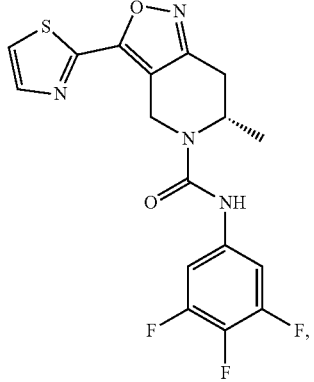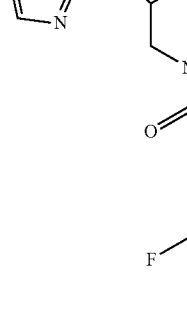
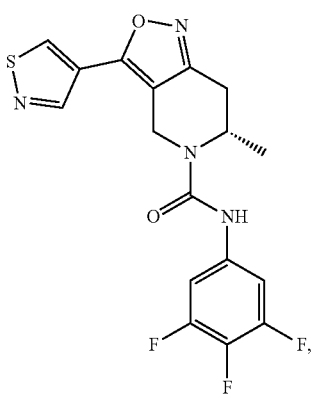

-continued

107
-continued
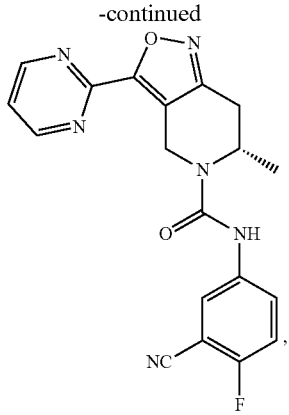
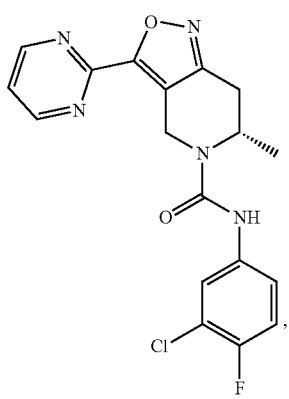
108
-continued
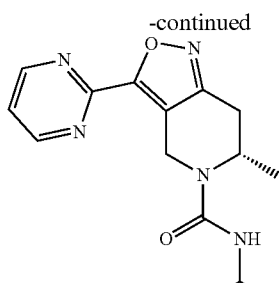
or
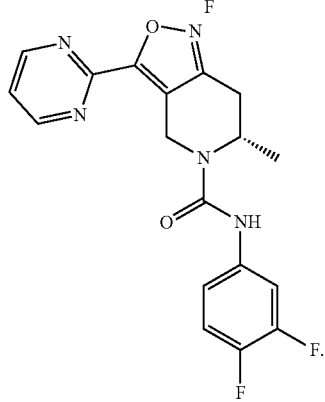
19. A pharmaceutical composition comprising a therapeutically effective amount of a compound, a pharmaceutically acceptable salt or an isomer thereof according to claim 1 as an active ingredient, and a pharmaceutically acceptable carrier.
* * * * *